(12) United States Patent
Hermon-Taylor et al.

(10) Patent No.: US 7,541,181 B2
(45) Date of Patent: Jun. 2, 2009

(54) VECTOR CARRYING A POLYNUCLEOTIDE WHICH ENCODES A GSD POLYPEPTIDE FROM MYCOBACTERIUM PARATUBERCULOSIS

(75) Inventors: John Hermon-Taylor, St. George's Hospital Medical School. Dept. Of Surgery, Cranmer Terrace, London (GB); Tim Doran, Whillington (AU); Douglas Millar, North Ryde (AU); Mark Tizard, London (GB); Mark Loughlin, London (GB); Nazira Sumar, London (GB); John Ford, London (GB)

(73) Assignee: John Hermon-Taylor, London (GB)

( * ) Notice: Subject to any disclaimer, the term of this patent is extended or adjusted under 35 U.S.C. 154(b) by 357 days.

(21) Appl. No.: 11/435,142

(22) Filed: May 17, 2006

(65) Prior Publication Data

US 2006/0204521 A1 Sep. 14, 2006

Related U.S. Application Data

(60) Continuation of application No. 10/805,311, filed on Mar. 22, 2004, now abandoned, which is a division of application No. 09/705,911, filed on Nov. 6, 2000, now abandoned, which is a division of application No. 09/091,538, filed as application No. PCT/GB96/03221 on Dec. 23, 1996, now Pat. No. 6,156,322.

(30) Foreign Application Priority Data

Dec. 21, 1995  (GB) ................................. 9526178.0

(51) Int. Cl.
| | |
|---|---|
| *C12N 15/00* | (2006.01) |
| *C12N 1/21* | (2006.01) |
| *C12N 15/86* | (2006.01) |
| *C12N 15/74* | (2006.01) |
| *C07H 21/04* | (2006.01) |
| *C07H 21/02* | (2006.01) |

(52) U.S. Cl. ................. 435/320.1; 435/252.3; 435/456; 435/471; 536/23.1; 424/200.1
(58) Field of Classification Search ...................... None
See application file for complete search history.

(56) References Cited

U.S. PATENT DOCUMENTS

| | | |
|---|---|---|
| 5,082,767 A | 1/1992 | Hatfield et al. |
| 6,156,322 A | 12/2000 | Hermon-Taylor et al. |

FOREIGN PATENT DOCUMENTS

| | | | |
|---|---|---|---|
| EP | 0 288 306 A | 10/1998 | |
| FR | 2 682 967 A | 4/1993 | |
| WO | WO 94 26312 A | 11/1994 | |
| WO | WO 95 01441 A | 1/1995 | |

OTHER PUBLICATIONS

Database EMBL, Entry MT024, Accession No. U00024, Jan. 5, 1995 nt.15203-15934 100% homology with SeqID:36 nt.14306-15133 100% homology with SeqID:38 XP002033471 cited in the application.

Database EMBL, Entry MTCY277, Accession No. Z79701, Sep. 18, 1996 nt.34705-36493 100% homology with SeqID:30 nt.31972-32994 100% homology with SeqID:32 nt.33956-34687 100% homology with SeqID:34 XP002033472 cited in the application.

Database EMBL, Entry MTAD1, Accession No. AD000001, Dec. 15, 1996 nt.6775-7562 100% homology with Seq.ID:30 nt.9273-10295 100% homology with Seq.ID:32 nt.7580-8311 100% homology with Seq.ID:34 XP002033473.

Database EMBL, Entry MTCY349, Accession No. Z83018, Nov. 26, 1996 nt.34695-35426 100% homology with SeqID:36 nt.33797-34624 100% homology with SeqID:38 XP002033474.

Database EMBL, Entry MTAD9, Accession No. AD000009, Dec. 15, 1996 nt.15203-15934 100% homology with SeqID:36 nt.14306-15133 100% homology with SeqID:38 XP002033475.

Vaccine, vol. 12, No. 16, 1994, pp. 1537-1540, XP002026338 Lowrie D B et al: "Towards a DNA Vaccine Against Tuberculosis" see p. 1537-p. 1538.

Nature, vol. 351, No. 6326, Jun. 6, 1991, pp. 456-460, XP000605495 Stover C K et al: "New Use of BCG for Recombinant Vaccines" see p. 456-p. 457.

Belisle, J. T. et al, "Isolation and Expression of a Gene Cluster Responsible for Biosynthesis of the Glycopeptidolipid Antigens of *Mycobacterium avium*." J. Bacteriol. 1991, 173; 6991-6997.

Belisle, J. T. et al, "Rough Morphological Variants of *Mycobacterium avium*. Characterisation of Genomic Deletions Resulting in the loss of Glycopeptidolipid Expression", J. Biological Chem. 1993, 268; 10517-10523.

Mills, J.A. et al, "Loci of *Mycobacterium avium ser2* Gene Cluster and their Functions", J. Bacteriol. 1994, 176:; 4803-4808.

Chemical Abstracts, vol. 74, No. 5, Feb. 1, 1971 Columbus Ohio, US; abstract No. 20614, Khachaturyan, A.A. et al: "Formation of acylases by hydrocarbon-oxidizing microorganisms" XP002190388 abstract & Biol. ZH. Arm. (1990), 23(7), 40-7.

Greenspan et al., Nature of Biotechnoogy 7:936-937, 1999.
Bowie et al, Science, 1990, 257:1306-1310.
Lehninger, Biochemistry, 1970, Worth Publishers, NY, NY.

*Primary Examiner*—Robert A Zeman
(74) *Attorney, Agent, or Firm*—Nixon & Vanderhye P.C.

(57) ABSTRACT

The invention provides a nucleotide sequence representing a pathogenicity island found in species of pathogenic mycobacteria. The islands are shown as SEQ ID NOS: 3 and 4 and comprises several open reading frames encoding polypeptides. These polypeptides and their use in diagnosis and therapy form a further aspect of the invention.

14 Claims, 1 Drawing Sheet

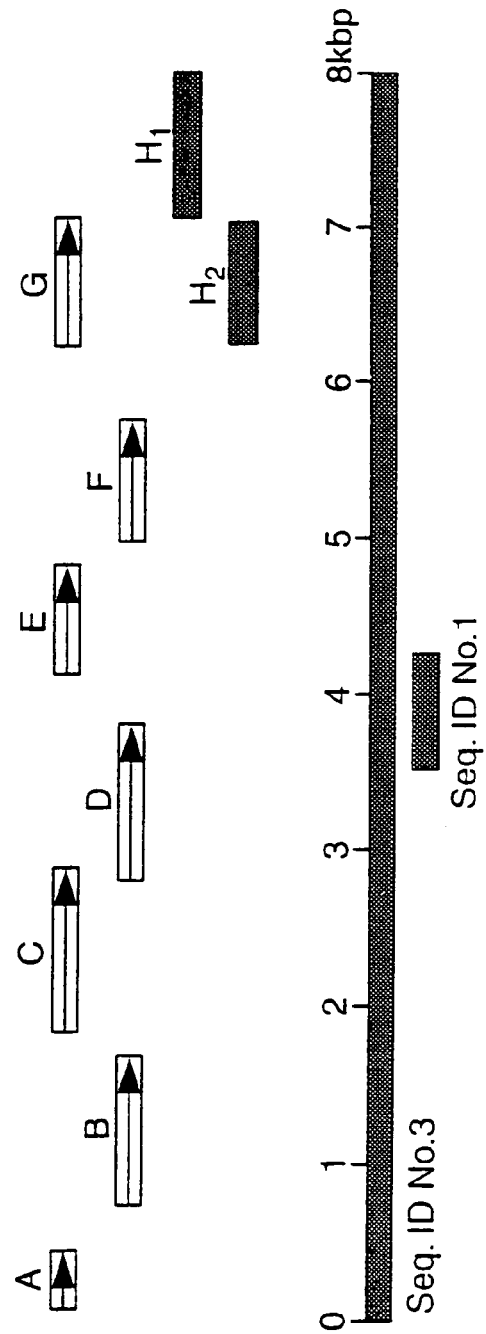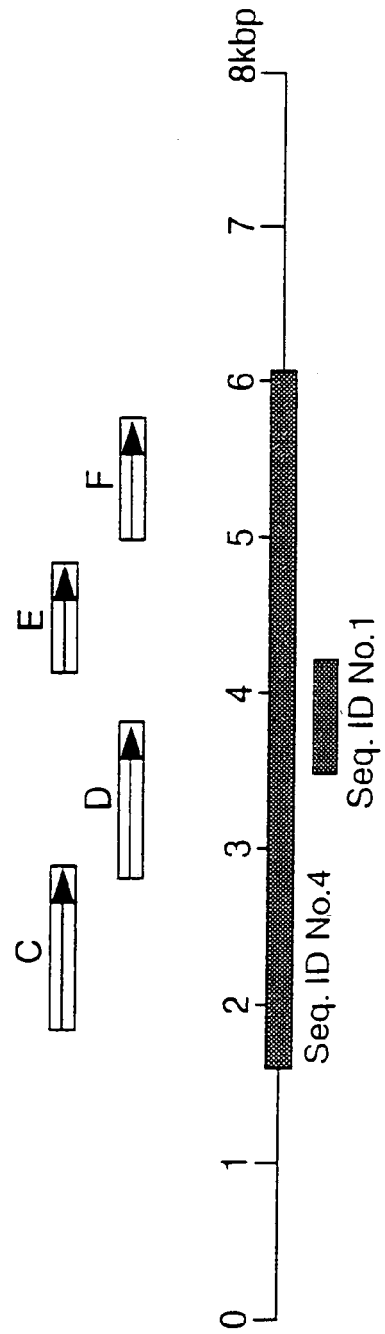

SEQUENCE LISTING

```
<160> NUMBER OF SEQ ID NOS: 41

<210> SEQ ID NO 1
<211> LENGTH: 674
<212> TYPE: DNA
<213> ORGANISM: Mycobacterium

<400> SEQUENCE: 1
gatccaacta aacccgatgg aaccccgcgc aaactattgg acgtctccgc gctacgcagt      60
tgggttggcg cccgcgaatc gcactgaaag agggcatcga tgcaacggtg tcgtggtacc     120
gcacaaatgc cgatgccgtg aggaggtaaa gctgcgggcc ggccgatgtt atccctccgg     180
ccggacgggt agggcgacct gccatcgagt ggtacggcag tcgcctggcc ggcgaggcgc     240
atggcctatg tgagtatccc atagcctggc ttggctcgcc cctacgcatt atcagttgac     300
```

```
cgctttcgcg ccacgtcgca ggcttgcggc agcatcccgt tcaggtctcc tcatggtccg    360
gtgtggcacg accacgcaag ctcgaaccga ctcgtttccc aatttcgcat gctaatatcg    420
ctcgatggat tttttgcgca acgccggctt gatggctcgt aacgttagca ccgagatgct    480
gcgccactcc gaacgaaagc gcctattagt aaaccaagtc gaagcatacg gagtcaacgt    540
tgttattgat gtcggtgcta actccggcca gttcggtagc gctttgcgtc gtgcaggatt    600
caagagccgt atcgtttcct ttgaacctct ttcggggcca tttgcgcaac taacgcgcaa    660
gtcggcatcg gatc                                                      674

<210> SEQ ID NO 2
<211> LENGTH: 674
<212> TYPE: DNA
<213> ORGANISM: Mycobacterium

<400> SEQUENCE: 2
gatccgatgc cgacttgcgc gttagttgcg caaatggccc cgaaagaggt tcaaaggaaa     60
cgatacggct cttgaatcct gcacgacgca aagcgctacc gaactggccg gagttagcac    120
cgacatcaat aacaacgttg actccgtatg cttcgacttg gtttactaat aggcgctttc    180
gttcggagtg gcgcagcatc tcggtgctaa cgttacgagc catcaagccg gcgttgcgca    240
aaaaatccat cgagcgatat tagcatgcga aattgggaaa cgagtcggtt cgagcttgcg    300
tggtcgtgcc acaccggacc atgaggagac ctgaacggga tgctgccgca agcctgcgac    360
gtggcgcgaa agcggtcaac tgataatgcg taggggcgag ccaagccagg ctatgggata    420
ctcacatagg ccatgcgcct cgccggccag gcgactgccg taccactcga tggcaggtcg    480
ccctacccgt ccggccggag ggataacatc ggcggcccg cagctttacc tcctcacggc    540
atcggcattt gtgcggtacc acgacaccgt tgcatcgatg ccctctttca gtgcgattcg    600
cgggcgccaa cccaactgcg tagcgcggag acgtccaata gtttgcgcgg ggttccatcg    660
ggtttagttg gatc                                                      674

<210> SEQ ID NO 3
<211> LENGTH: 7995
<212> TYPE: DNA
<213> ORGANISM: Mycobacterium

<400> SEQUENCE: 3
gaattctggg ttggagacga cgtcgaactc ctggtcggtc ttgcttcgaa tgatcgctgt     60
gatctggtcg gcggtgccga caggaaccgt cgacttgtcg acgatcacct tgtaccggtc    120
gatgtatgac ccaatgtcgt ccgcaaccga gaagacgtac gtcaggtccg ccgccccgct    180
ttcacccatg ggcgtcggga cggcgatgaa atgacgtcc gcgtgctcga ttccgcgttg    240
ccggtcggtg gtgaagtcaa tcagcccgtt ctcacggttc ctcgcaatca actcccaacc    300
cgggctcgaa aatcgggaca ctgcctgcga ggagcaaatc gatcttggcc tgatcgatat    360
cgacacagac gacatcgttg ccgctatccg cgagacaggc gcccgtgacg aggcctacat    420
agcctgatcc gaccaccgaa attttcaaga tgacccttc aagtcccga tcggtcgacg    480 accatactgc cgcaactctg taccctccgt gggtaattcg catgtcgcgt tcgtaaggag    540
cagccagcga gtcgggacg ttcggtgaga gagtcgcagg actacgaggt tgccggtgcg    600
atacatcaca gtgttgcgtc tgtcggcaac gatgcagcaa gaacccacgg ggcagccctg    660
aactgcgcgc atgaccggtc cttgtcctgg caccttgat cggccaccgc ttccatgcga    720
acatgaccgg aatccatagc gcgtggtcaa gcagcgggga ggtagacgtc ggtgtcatct    780
```

```
gctccaaccg tgtcggtgat aacgatttcg ctgaacgatc tcgagggatt gaaaagcacc      840
gtggagagcg ttcgcgcgca gcgctatggg gggcgaatcg agcacatcgt catcgacggt      900
ggatcgggcg acgccgtcgt ggagtatctg tccggcgatc ctggctttgc atattggcaa      960
tctcagcccg acaacgggag atatgacgcg atgaatcagg gcattgccca ttcgtcgggc     1020
gacctgttgt ggtttatgca ctccacggat cgtttctccg atccagatgc agtcgcttcc     1080
gtggtggagg cgctctcggg gcatggacca gtacgtgatt tgtggggtta cgggaaaaac     1140
aaccttgtcg gactcgacgg caaaccactt ttccctcggc cgtacggcta tatgccgttt     1200
aagatgcgga aatttctgct cggcgcgacg gttgcgcatc aggcgacatt cttcggcgcg     1260
tcgctggtag ccaagttggg cggttacgat cttgattttg gactcgaggc ggaccagctg     1320
ttcatctacc gtgccgcact aatacggcct cccgtcacga tcgaccgcgt ggtttgcgac     1380
ttcgatgtca cggggacctgg ttcaacccag cccatccgtg agcactatcg accctgcgg     1440 cggctctggg acctgcatgg cgactacccg ctgggtgggc gcagagtgtc gtgggcttac     1500
ttgcgtgtga aggagtactt gattcgggcc gacctggccg cattcaacgc ggtaaagttc     1560
ttgcgagcga agttcgccag agcttcgcgg aagcaaaatt catagaaacc aacttctact     1620
gcctgacctg agcagcgccg aggcgcgcag cgcgatcagt gcgacctgaa cggccaggtg     1680
gaaagcgcca ccgatcccgg caccgagtgc ctgacgcttc ggatcccttg caccacaacg     1740
agagtgagag cgccatgatg aggaaatatc ggctgggcgg agtcaacgcc ggagtgacaa     1800
aagtgagaac ccggtgaagc gagcgcttat aacaggatc acggggcagg atggttccta     1860
cctcgccgag ctactactga gcaagggata cgaggttcac gggctcgttc gtcgagcttc     1920
gacgtttaac acgtcgcgga tcgatcacct ctacgttgac ccacaccaac cgggcgcgcg     1980
cttgttcttg cactatgcag acctcactga cggcacccgg ttggtgaccc tgctcagcag     2040
tatcgacccg gatgaggtct acaacctcgc agcgcagtcc catgtgcgcg tcagctttga     2100
cgagccagtg cataccggag acaccaccgg catgggatcg atccgacttc tggaagcagt     2160 ccgccttttct cgggtggact gccggttcta tcaggcttcc tcgtcggaga tgttcggcgc     2220
atctccgcca ccgcagaacg aatcgacgcc gttctatccc cgttcgccat acggcgcggc     2280
caaggtcttc tcgtactgga cgactcgcaa ctatcgagag cgtacggat tattcgcagt      2340 gaatggcatc ttgttcaacc atgagtcccc ccggcgcggc gagactttcg tgacccgaaa     2400
gatcacgcgt gccgtggcgc gcatccgagc tggcgtccaa tcgaggtct atatgggcaa      2460 cctcgatgcg atccgcgact ggggctacgc gcccgaatat gtcgagggga tgtggaggat     2520
gttgcaagcg cctgaacctg atgactacgt cctggcgaca gggcgtggtt acaccgtacg     2580
tgagttcgct caagctgctt ttgaccatgt cgggctcgac tggcaaaagc gcgtcaagtt     2640
tgacgaccgc tatttgcgtc ccaccgaggt cgattcgcta gtaggagatg ccgacaaggc     2700
ggcccagtca ctcggctgga agcttcggt tcatactggt gaactcgcgc gcatcatggt     2760
ggacgcggac atcgccgcgt tggagtgcga tggcacacca tggatcgaca cgccgatgtt     2820
gcctggttgg ggcagagtaa gttgacgact acacctgggc ctctggaccg cgcaacgccc     2880
gtgtatatcg ccggtcatcg ggggctggtc ggctcagcgc tcgtacgtag atttgaggcc     2940
gaggggttca ccaatctcat tgtgcgatca cgcgatgaga ttgatctgac ggaccgagcc     3000
gcaacgtttg attttgtgtc tgagacaaga ccacaggtga tcatcgatgc ggccgcacgg     3060
gtcggcggca tcatggcgaa taacacctat cccgcggact tcttgtccga aaacctccga     3120
```

```
atccagacca atttgctcga cgcagctgtc gccgtgcgtg tgccgcggct ccttttcctc    3180
ggttcgtcat gcatctaccc gaagtacgct ccgcaaccta tccacgagag tgctttattg    3240
actggcccct tggagcccac caacgacgcg tatgcgatcg ccaagatcgc cggtatcctg    3300
caagttcagg cggttaggcg ccaatatggg ctggcgtgga tctctgcgat gccgactaac    3360
ctctacggac ccggcgacaa cttctccccg tccgggtcgc atctcttgcc ggcgctcatc    3420
cgtcgatatg aggaagccaa agctggtggt gcagaagagg tgacgaattg ggggaccggt    3480
actccgcggc gcgaacttct gcatgtcgac gatctggcga gcgcatgcct gttccttttg    3540
gaacatttcg atggtccgaa ccacgtcaac gtgggcaccg cgtcgatca cagcattagc     3600 gagatcgcag acatggtcgc tacagcggtg ggctacatcg gcgaaacacg ttgggatcca    3660
actaaacccg atgaaccccc gcgcaaacta ttggacgtct ccgcgctacg cgagttgggt    3720
tggcgcccgc gaatcgcact gaaagacggc atcgatgcaa cggtgtcgtg gtaccgcaca    3780
aatgccgatg ccgtgaggag gtaaagctgc gggtcggccg atgttatccc tccgccgga    3840 cgggtggggc gacctgccgt cgagtggtac ggcagtcgcc tggccggcga ggcgcgtggc    3900
ctatgggagt atccaatagc ctggcttggc tcgcccctac gcattatcag ttgaccgctt    3960
tcgcgccagc tcgcaggctt gcggcagcat cccgttcagg tctcctcatg gtccggtgtg    4020
gcacgaccac gcaagctcga accgactcgt ttcccaattt cgcatgctaa tatcgctcga    4080 tggattttt gcgcaacgcc ggcttgatgg ctcgtaacgt tagtaccgag atgctgcgcc     4140
acttcgaacg aaagcgccta ttagtaaacc aattcaaagc atacggagtc aacgttgtta    4200
ttgatgtcgg tgctaactcc ggccagttcg gtagcgcttt gcgtcgtgca ggattcaaga    4260
gccgtatcgt ttcctttgaa cctctttcgg ggccatttgc gcaactaacg cgcaagtcgg    4320
catcggatcc actatgggag tgtcaccagt atgccctagg cgacgccgat gagacgatta    4380
ccatcaatgt ggcaggcaat gcggggggcaa gtagttccgt gctgccgatg cttaaaagtc    4440
atcaagatgc ctttcctccc gcgaattata ttggcaccga agacgttgca atacaccgcc    4500
ttgattcggt tgcatcagaa tttctgaacc ctaccgatgt tactttcctg aagatcgacg    4560
tacagggttt cgagaagcag gttatcacgg gcagtaagtc aacgcttaac gaaagctgcg    4620
tcggcatgca actcgaactt tctttttattc cgttgtacga aggtgacatg ctgattcatg    4680
aagcgcttga acttgtctat tccctaggtt tcagactgac gggtttgttg cccggcttta    4740
cggatccgcg caatggtcga atgcttcaag ctgacggcat tttcttccgt ggggacgatt    4800
gacataaatg ctccgtcggc accctgccgg tatccaaacg ggcgatctgg tgagccggcc    4860
tcccgggcac ctaatcgact atctaaattg aggcggccgc gacgtgcggc acgaacaggt    4920
ggccggctgc tagcgttaca cacgtcatga ctgcgccagt gttctcgata attatcccta    4980
ccttcaatgc agcggtgacg ctgcaagcct gcctcggaag catcgtcggg cagacctacc    5040
gggaagtgga agtggtcctt gtcgacgcg gttcgaccga tcggaccctc gacatcgcga     5100
acagtttccg cccggaactc ggctcgcgac tggtcgttca cagcgggccc gatgatggcc    5160
cctacgacgc catgaaccgc ggcgtcgcg tggccacagg cgaatgggta ctttttttag     5220
gcgccgacga caccctctac gaaccaacca cgttgcccca ggtagccgct tttctcggcg    5280 accatgcgg aagccatctt gtctatgcg atgttgtgat cgttcgacg aaaagcggc       5340 atgccggacc tttcgacctc gaccgcctcc tatttgagac gaatttgtgc caccaatcga    5400
tcttttaccg ccgtgagctt ttcgacggca tcggccctta caacctgcgc taccgagtct    5460
gggcggactg ggacttcaat attcgctgct tctccaaccc ggcgctgatt accgctaca     5520
```

```
tggacgtcgt gatttccgaa tacaacgaca tgaccggctt cagcatgagg caggggactg    5580
ataaagagtt cagaaaacgg ctgccaatgt acttctgggt tgcagggtgg gagacttgca    5640
ggcgcatgct ggcgtttttg aaagacaagg agaatcgccg tctggccttg cgtacgcggt    5700
tgataagggt taaggccgtc tccaaagaac gaagcgcaga accgtagtcg cggatccaca    5760
ttggacttct ttaacgcgtt tgcgtcctga tccacctttc aagcccgttc cgcgtaacgc    5820
ggcgcgcaga gagtggtcgc atatcgcatc actgttctcg tgccagtgct tggaaagcgt    5880
cgagcactct ggttcgcgtt cttgacgttc gcgcccgctc ctagaggtag cgtgtcacgt    5940
gactgaagcc aatgagtgca actcggcgtc gcgaaaggtt tcagtcgcgg ttgagcaaga    6000
caccgcaaga ctactggagt gcgtgcacaa gcgcctccag ctcgcggctg aaagcggatg    6060
caaagggatt cgaagcttga gcaacatgcg aaggggagaa cggcctatga ggctgggaca    6120
ggttttcgat ccgcgcgcga atgcactgtc aatggccaag tagaagtccc cgctggtggc    6180
cagcagaagt ccccactccg ctgcgggtgg ttggctaatt cttggcggct cccttcttgt    6240
ggtcggcgtg gcgcatccgg taggactcgc cggaggtgac gacgatgctg gcgtggtgca    6300
gcagccgatc gaggatgctg gcggcggtgg tgtgctcggg caggaatcgc ccccattgtt    6360
cgaagggcca atgcgaggcg atggccaggg agcggcgctc gtagccggca gccacgagcc    6420
ggaacaacag ttgagtcccg tgtcgtcga gcggggcgaa gccgatctcg tccaagatga    6480
ccagatccgc gcggagcagg gtgtcgatga tcttgccgac ggtgttgtcg gccaggccgc    6540
ggtagaggac ctcgatcagg tcggcggcgg tgaagtagcg gactttgaat ccggcgtgga    6600
cggcagcgtg cccgcagccg atgagcaggt gacttttgcc cgtaccaggt gggccaatga    6660
ccgccaggtt ctgttgtgcc cgaatccatt ccaggctcga caggtagtcg aacgtggctg    6720
cggtgatcga cgatccggtg acgtcgaacc cgtcgagggt cttggtgacc gggaaggctg    6780
cggccttgag acgttggcg gtgttggagg catcgcgggc agcgatctcg gcctcaacca    6840
acgtccgcag gatctcctcc ggtgtccagc gttgcgtctt ggcgacttgc aacacctcgg    6900
cggcgttgcg gcgcaccgtg gccagcttca accgccgcag cgccgcgtca aggtcagcag    6960
ccagcggtgc cgccgaggac ggtgccaccg gcttggcagc ggtggtcatg aggccgtccc    7020
gtcggtggtg ttgatcttgt aggcctccaa cgagcgggtc tcgacggtgg gcagatcgag    7080
cacgagtgcg tcgccggcgg ggcggggttg tggggtgccg gcgccggcgg ccaggatcga    7140
gcgcacgtcg gcagcgcgga accggcgaaa cgcaaccgcc cggcgcagcg cgtcaatcaa    7200
agcctgttcg ccgtgggcgg cgccaaggcc gagcagaatg tcgagttcgg atttcagtcg    7260
ggtgttgccg atcgcagcag caccgacgag gaactgctgc gcttcggttc ccaatgcgca    7320
gaatcgtttc tctgcttggg ttttcgggcg aggaccacgc gagggtgcgg gtctgggtcc    7380
gtcgtagtgt tcatcgagga tggacacctc acctgggctg acgagctcgt gctcggccac    7440
gatcacaccg gtcgcaggtt ccaacaggat cagggcgcca tgatcgacca ccaccgccac    7500
ggtggcaccg acgagccgct gaggcaccga gtaacgagct gagccgtaac ggatgcacga    7560
gaggccgtcg accttacggc gcaccgaccc cgagccgatc gtcggccgca gcgagggcag    7620
ctccctcaag acggtgcgct cgtcaaccaa gcgatcgttg ggcacggcgc agatctccga    7680
gtggaccgtg gcattgacct cggcgcacca tagttgcgcc tgggcgttga gggcacgtag    7740
gtcgacctgc tcaccggcta acgcagcttc ggtcagcagc ggcaccgcaa ggtcgtcctg    7800
agcgtagcca cagaggttct ccacgatgcc cttcgattgc ggatccgcac cgtggcagaa    7860
```

-continued

```
gtccggaacg aagccatagt gggacgcgaa tcgcacataa tccggtgttg gaacaacaac    7920
attggcgacg acaccacctt tgaggcagcc catccggtcg gccaggatct tggccggaac    7980
cccaccgatc gcctc                                                     7995

<210> SEQ ID NO 4
<211> LENGTH: 4435
<212> TYPE: DNA
<213> ORGANISM: Mycobacterium

<400> SEQUENCE: 4
ttctactgcc tgacctgagc agcgccgagg cgcgcagcgc gatcactgcg acctgaatgg      60
ccaggtggaa agcgccaccg atcccggcac cgagtgcctg acgattcgga tcccttgcac     120
cacaacgaga gtgagaccgc catgatgacg aaatatcggc tgggcggagt caacgccgga     180
gtgacaaaag tgagaacccg gtgaagcgag cgcttataac agggatcacg gggcaggatg     240
gttcctacct cgccgagcta ctactgagca agggatacga ggttcacggg ctcgttcgtc     300
gagcttcgac gtttaacacg tcgcggatcg atcacctcta cgttgaccca caccaaccgg     360
gcgcgcgctt gttcttgcac tatgcagacc tcactgacgg cacccggttg gtgaccctgc     420
tcagcagtat cgacccggat gaggtctaca acctcgcagc gcagtcccat gtgcgcgtca     480
gctttgacga gccagtgcat accggagaca ccaccggcat gggatcgatc cgacttctgg     540
aagcagtccg cctttctcgg gtggactgcc ggttctatca ggcttcctcg tcggagatgt     600
tcggcgcatc tccgccaccg cagaacgaat cgacgccgtt ctatccccgt cgccatacg     660 gcgcggccaa ggtcttctcg tactggacga ctcgcaacta tcgagaggcg tacggattat     720
tcgcagtgaa tggcatcttg ttcaaccatg agtcccccg gcgcggcgag actttcgtga     780
cccgaaagat cacgcgtgcc gtggcgcgca tccgagctgg ctgccaatcg gaggtctata     840
tgggcaacct cgatgcgatc cgcgactggg gctacgcgcc cgaatatgtc gaggggatgt     900
ggaggatgtt gcaagcgcct gaacctgatg actacgtcct ggcgacaggg cgtggttaca     960
ccgtacgtga gttcgctcaa gctgcttttg accacgtcgg gctcgactgg caaaagcacg    1020
tcaagtttga cgaccgctat ttgcgccca ccgaggtcga ttcgctagta ggagatgccg    1080
acagggcggc ccagtcactc ggctggaaag cttcggttca tactggtgaa ctcgcgcgca    1140
tcatggtgga cgcggacatc gccgcgtcgg agtgcgatgg cacaccatgg atcgacacgc    1200
cgatgttgcc tggttgggc ggagtaagtt gacgactaca cctgggcctc tggaccgcgc    1260
aacgcccgtg tatatcgccg gtcatcgggg gctggtcggc tcagcgctcg tacgtagatt    1320
tgaggccgag gggttcacca atctcattgt gcgatcacgc gatgagattg atctgacgga    1380
ccgagccgca acgtttgatt ttgtgtctga dacaagacca caggtgatca tcgatgcggc    1440
cgcacgggtc ggcggcatca tggcgaataa cacctatccc gcggacttct tgtccgaaaa    1500
cctccgaatc cagaccaatt tgctcgacgc agctgtcgcc gtgcgtgtgc gcggctcct     1560 tttcctcggt tcgtcatgca tctacccgaa gtacgctccg caacctatcc acgagagtgc    1620
tttattgact ggcccctttgg agcccaccaa cgacgcgtat gcgatcgcca agatcgccgg    1680
tatcctgcaa gttcaggcgg ttaggcgcca atatgggctg gcgtggatct ctgcgatgcc    1740
gactaacctc tacggaccc gcgacaactt ctccccgtcc gggtcgcatc tcttgccggc    1800
gctcatccgt cgatatgagg aagccaaagc tggtggtgca gaagaggtga cgaattgggg    1860
gaccggtact ccgcggcgcg aacttctgca tgtcgacgat ctggcgagcg catgcctgtt    1920 cctttttggaa catttcgatg gtccgaacca cgtcaacgtg ggcaccggcg tcgatcacag    1980
```

```
cattagcgag atcgcagaca tggtcgctac ggcggtgggc tacatcggcg aaacacgttg   2040
ggatccaact aaacccgatg gaaccccgcg caaactattg gacgtctccg cgctacgcga   2100
gttgggttgg cgcccgcgaa tcgcactgaa agacggcatc gatgcaacgg tgtcgtggta   2160
ccgcacaaat gccgatgccg tgaggaggta aagctgcggg ccggccgatg ttatccctcc   2220
ggccggacgg gtagggcgac ctgccatcga gtggtacggc agtcgcctgg ccggcgaggc   2280
gcatggccta tgggagtatc ccatagcctg gcttggctcg cccctacgca ttatcagttg   2340
accgctttcg cgccagctcg caggctcgcg gcagcatccc gttcaggtct cctcatggtc   2400
cggtgtggca cgaccacgca agctcgaacc gactcgtttc ccaatttcgc atgctaatat   2460
cgctcgatgg attttttgcg caacgccggc ttgatggctc gtaacgttag caccgagatg   2520
ctgcgccact tcgaacgaaa gcgcctatta gtaaaccaat tcaaagcata cggagtcaac   2580
gttgttattg atgtcggtgc taactccggc cagttcggta gcgctttgcg tcgtgcagga   2640
ttcaagagcc gtatcgtttc cttttgaacct cttcgggggc catttgcgca actaacgcgc   2700
gagtcggcat cggatccact atgggagtgt caccagtatg ccctaggcga cgccgatgag   2760
acgattacca tcaatgtggc aggcaatgcg ggggcaagta gttccgtgct gccgatgctt   2820
aaaagtcatc aagatgcctt tcctcccgcg aattatattg gcaccgaaga cgttgcaata   2880
caccgccttg attcggttgc atcagaattt ctgaaccccta ccgatgttac tttcctgaag   2940
atcgacgtac agggtttcga gaagcaggtt atcgcgggca gtaagtcaac gcttaacgaa   3000
agctgcgtcg gcatgcaact cgaactttct tttattccgt tgtacgaagg tgacatgctg   3060
attcatgaag cgcttgaact tgtctattcc ctaggtttca gactgacggg tttgttgccc   3120
ggatttacgg atccgcgcaa tggtcgaatg cttcaagctg acggcatttt cttccgtggg   3180
gacgattgac ataaatgctt gcgtcggcac cctgccggta tccaaacggg cgatctggtg   3240
agccggcctc ccgggcacct aatcgactat ctaaattgag gcggccgcga cgtgcggcac   3300
gaacaggtgg ccggctgcta gcgttacaca cgtcatgact gcgccagtgt tctcgataat   3360
tatccctacc ttcaatgcag cggtgacgct gcaagcctgc ctcggaagca tcgtcgggca   3420
gacctaccgg gaagtggaag tggtccttgt cgacggcggt tcgaccgatc ggaccctcga   3480
catcgcgaac agtttccgcc cggaactcgg ctcgcgactg gtcgttcaca gcgggcccga   3540
tgatggcccc tacgacgcca tgaaccgcgg cgtcggcgta gccacaggcg aatgggtact   3600
ttttttaggc gccgacgaca ccctctacga accaaccacg ttgggcccagg tagccgcttt   3660 tctcggcgac catgcggcaa gccatcttgt ctatggcgat gttgtgatgc gttcgacgaa   3720
aagccggcat gccggacctt tcgacctcga ccgcctccta tttgagacga atttgtgcca   3780
ccaatcgatc ttttaccgcc gtgagctttt cgacggcatc ggcccttaca acctgcgcta   3840
ccgagtctgg gcggactggg acttcaatat tcgctgcttc tccaacccgg cgctgattac   3900
ccgctacatg gacgtcgtga tttccgaata caacgacatg accggcttca gcatgaggca   3960
ggggactgat aaaagagttca gaaaacggct gccaatgtac ttctgggttg cagggtggga   4020
gacttgcagg cgcatgctgg cgttttttgaa agacaaggag aatcgccgtc tggccttgcg   4080
tacgcggttg ataagggtta aggccgtctc caaagaacga agcgcagaac cgtagtcgcg   4140
gatccacatt ggacttcttt aacgcgtttg cgtcctgatc cacctttcaa ccccgttccg   4200
cgtgacgcgg cgcgcagaga gtggtcgcat atcgcgtcac tgttctcgtg ccagtgcttg   4260
gaaagcgtcg agcactctgg ttcgcgttct tgacgttcgc gcccgcccct agaggtagcg   4320
```

```
tgtcacgtga ctgaagccaa tgagtgcaac tcggcgtcgc gaaaggtttc agtcgcggtt    4380
gagcaagaca ccgcaagact actggagtgc gtgcacaagc gcctccagct cacgg         4435

<210> SEQ ID NO 5
<211> LENGTH: 378
<212> TYPE: DNA
<213> ORGANISM: Mycobacterium
<220> FEATURE:
<221> NAME/KEY: CDS
<222> LOCATION: (1)..(375)

<400> SEQUENCE: 5 atg atc gct gtg atc tgg tcg gcg gtg ccg aca gga acc gtc gac ttg      48
Met Ile Ala Val Ile Trp Ser Ala Val Pro Thr Gly Thr Val Asp Leu
 1               5                  10                  15 tcg acg atc acc ttg tac cgg tcg atg tat gac cca atg tcg tcc gca      96
Ser Thr Ile Thr Leu Tyr Arg Ser Met Tyr Asp Pro Met Ser Ser Ala
                20                  25                  30 acc gag aag acg tac gtc agg tcc gcc gcc ccg ctt tca ccc atg ggc     144
Thr Glu Lys Thr Tyr Val Arg Ser Ala Ala Pro Leu Ser Pro Met Gly
            35                  40                  45 gtc ggg acg gcg atg aaa atg acg tcc gcg tgc tcg att ccg cgt tgc     192
Val Gly Thr Ala Met Lys Met Thr Ser Ala Cys Ser Ile Pro Arg Cys
        50                  55                  60 cgg tcg gtg gtg aag tca atc agc ccg ttc tca cgg ttc ctc gca atc     240
Arg Ser Val Val Lys Ser Ile Ser Pro Phe Ser Arg Phe Leu Ala Ile
 65                 70                  75                  80 aac tcc caa ccc ggg ctc gaa aat cgg gac act gcc tgc gag gag caa     288
Asn Ser Gln Pro Gly Leu Glu Asn Arg Asp Thr Ala Cys Glu Glu Gln
                85                  90                  95 atc gat ctt ggc ctg atc gat atc gac aca gac gac atc gtt gcc gct     336
Ile Asp Leu Gly Leu Ile Asp Ile Asp Thr Asp Asp Ile Val Ala Ala
            100                 105                 110 atc cgc gag aca ggc gcc cgt gac gag gcc tac ata gcc tga             378
Ile Arg Glu Thr Gly Ala Arg Asp Glu Ala Tyr Ile Ala
        115                 120                 125

<210> SEQ ID NO 6
<211> LENGTH: 125
<212> TYPE: PRT
<213> ORGANISM: Mycobacterium

<400> SEQUENCE: 6

Met Ile Ala Val Ile Trp Ser Ala Val Pro Thr Gly Thr Val Asp Leu
 1               5                  10                  15

Ser Thr Ile Thr Leu Tyr Arg Ser Met Tyr Asp Pro Met Ser Ser Ala
                20                  25                  30

Thr Glu Lys Thr Tyr Val Arg Ser Ala Ala Pro Leu Ser Pro Met Gly
            35                  40                  45

Val Gly Thr Ala Met Lys Met Thr Ser Ala Cys Ser Ile Pro Arg Cys
        50                  55                  60

Arg Ser Val Val Lys Ser Ile Ser Pro Phe Ser Arg Phe Leu Ala Ile
 65                 70                  75                  80

Asn Ser Gln Pro Gly Leu Glu Asn Arg Asp Thr Ala Cys Glu Glu Gln
                85                  90                  95

Ile Asp Leu Gly Leu Ile Asp Ile Asp Thr Asp Asp Ile Val Ala Ala
            100                 105                 110

Ile Arg Glu Thr Gly Ala Arg Asp Glu Ala Tyr Ile Ala
        115                 120                 125
```

```
<210> SEQ ID NO 7
<211> LENGTH: 834
<212> TYPE: DNA
<213> ORGANISM: Mycobacterium
<220> FEATURE:
<221> NAME/KEY: CDS
<222> LOCATION: (1)..(831)

<400> SEQUENCE: 7 gtg tca tct gct cca acc gtg tcg gtg ata acg att tcg ctg aac gat        48
Val Ser Ser Ala Pro Thr Val Ser Val Ile Thr Ile Ser Leu Asn Asp
  1               5                  10                  15 ctc gag gga ttg aaa agc acc gtg gag agc gtt cgc gcg cag cgc tat        96
Leu Glu Gly Leu Lys Ser Thr Val Glu Ser Val Arg Ala Gln Arg Tyr
             20                  25                  30 ggg ggg cga atc gag cac atc gtc atc gac ggt gga tcg ggc gac gcc       144
Gly Gly Arg Ile Glu His Ile Val Ile Asp Gly Gly Ser Gly Asp Ala
         35                  40                  45 gtc gtg gag tat ctg tcc ggc gat cct ggc ttt gca tat tgg caa tct       192
Val Val Glu Tyr Leu Ser Gly Asp Pro Gly Phe Ala Tyr Trp Gln Ser
     50                  55                  60 cag ccc gac aac ggg aga tat gac gcg atg aat cag ggc att gcc cat       240
Gln Pro Asp Asn Gly Arg Tyr Asp Ala Met Asn Gln Gly Ile Ala His
 65                  70                  75                  80 tcg tcg ggc gac ctg ttg tgg ttt atg cac tcc acg gat cgt ttc tcc       288
Ser Ser Gly Asp Leu Leu Trp Phe Met His Ser Thr Asp Arg Phe Ser
                 85                  90                  95 gat cca gat gca gtc gct tcc gtg gtg gag gcg ctc tcg ggg cat gga       336
Asp Pro Asp Ala Val Ala Ser Val Val Glu Ala Leu Ser Gly His Gly
            100                 105                 110 cca gta cgt gat ttg tgg ggt tac ggg aaa aac aac ctt gtc gga ctc       384
Pro Val Arg Asp Leu Trp Gly Tyr Gly Lys Asn Asn Leu Val Gly Leu
        115                 120                 125 gac ggc aaa cca ctt ttc cct cgg ccg tac ggc tat atg ccg ttt aag       432
Asp Gly Lys Pro Leu Phe Pro Arg Pro Tyr Gly Tyr Met Pro Phe Lys
    130                 135                 140 atg cgg aaa ttt ctg ctc ggc gcg acg gtt gcg cat cag gcg aca ttc       480
Met Arg Lys Phe Leu Leu Gly Ala Thr Val Ala His Gln Ala Thr Phe
145                 150                 155                 160 ttc ggc gcg tcg ctg gta gcc aag ttg ggc ggt tac gat ctt gat ttt       528
Phe Gly Ala Ser Leu Val Ala Lys Leu Gly Gly Tyr Asp Leu Asp Phe
                165                 170                 175 gga ctc gag gcg gac cag ctg ttc atc tac cgt gcc gca cta ata cgg       576
Gly Leu Glu Ala Asp Gln Leu Phe Ile Tyr Arg Ala Ala Leu Ile Arg
            180                 185                 190 cct ccc gtc acg atc gac cgc gtg gtt tgc gac ttc gat gtc acg gga       624
Pro Pro Val Thr Ile Asp Arg Val Val Cys Asp Phe Asp Val Thr Gly
        195                 200                 205 cct ggt tca acc cag ccc atc cgt gag cac tat cgg acc ctg cgg cgg       672
Pro Gly Ser Thr Gln Pro Ile Arg Glu His Tyr Arg Thr Leu Arg Arg
    210                 215                 220 ctc tgg gac ctg cat ggc gac tac ccg ctg ggt ggg cgc aga gtg tcg       720
Leu Trp Asp Leu His Gly Asp Tyr Pro Leu Gly Gly Arg Arg Val Ser
225                 230                 235                 240 tgg gct tac ttg cgt gtg aag gag tac ttg att cgg gcc gac ctg gcc       768
Trp Ala Tyr Leu Arg Val Lys Glu Tyr Leu Ile Arg Ala Asp Leu Ala
                245                 250                 255 gca ttc aac gcg gta aag ttc ttg cga gcg aag ttc gcc aga gct tcg       816
Ala Phe Asn Ala Val Lys Phe Leu Arg Ala Lys Phe Ala Arg Ala Ser
            260                 265                 270
```

```
cgg aag caa aat tca tag                                              834
Arg Lys Gln Asn Ser
        275

<210> SEQ ID NO 8
<211> LENGTH: 277
<212> TYPE: PRT
<213> ORGANISM: Mycobacterium

<400> SEQUENCE: 8

Val Ser Ser Ala Pro Thr Val Ser Val Ile Thr Ile Ser Leu Asn Asp
  1               5                  10                  15

Leu Glu Gly Leu Lys Ser Thr Val Glu Ser Val Arg Ala Gln Arg Tyr
                 20                  25                  30

Gly Gly Arg Ile Glu His Ile Val Ile Asp Gly Gly Ser Gly Asp Ala
             35                  40                  45

Val Val Glu Tyr Leu Ser Gly Asp Pro Gly Phe Ala Tyr Trp Gln Ser
         50                  55                  60

Gln Pro Asp Asn Gly Arg Tyr Asp Ala Met Asn Gln Gly Ile Ala His
 65                  70                  75                  80

Ser Ser Gly Asp Leu Leu Trp Phe Met His Ser Thr Asp Arg Phe Ser
                 85                  90                  95

Asp Pro Asp Ala Val Ala Ser Val Val Glu Ala Leu Ser Gly His Gly
                100                 105                 110

Pro Val Arg Asp Leu Trp Gly Tyr Gly Lys Asn Asn Leu Val Gly Leu
            115                 120                 125

Asp Gly Lys Pro Leu Phe Pro Arg Pro Tyr Gly Tyr Met Pro Phe Lys
130                 135                 140

Met Arg Lys Phe Leu Leu Gly Ala Thr Val Ala His Gln Ala Thr Phe
145                 150                 155                 160

Phe Gly Ala Ser Leu Val Ala Lys Leu Gly Gly Tyr Asp Leu Asp Phe
                165                 170                 175

Gly Leu Glu Ala Asp Gln Leu Phe Ile Tyr Arg Ala Ala Leu Ile Arg
            180                 185                 190

Pro Pro Val Thr Ile Asp Arg Val Cys Asp Phe Asp Val Thr Gly
        195                 200                 205

Pro Gly Ser Thr Gln Pro Ile Arg Glu His Tyr Arg Thr Leu Arg Arg
    210                 215                 220

Leu Trp Asp Leu His Gly Asp Tyr Pro Leu Gly Gly Arg Arg Val Ser
225                 230                 235                 240

Trp Ala Tyr Leu Arg Val Lys Glu Tyr Leu Ile Arg Ala Asp Leu Ala
                245                 250                 255

Ala Phe Asn Ala Val Lys Phe Leu Arg Ala Lys Phe Ala Arg Ala Ser
            260                 265                 270

Arg Lys Gln Asn Ser
        275

<210> SEQ ID NO 9
<211> LENGTH: 1032
<212> TYPE: DNA
<213> ORGANISM: Mycobacterium
<220> FEATURE:
<221> NAME/KEY: CDS
<222> LOCATION: (1)..(1029)

<400> SEQUENCE: 9 gtg aag cga gcg ctt ata aca ggg atc acg ggg cag gat ggt tcc tac   48
Val Lys Arg Ala Leu Ile Thr Gly Ile Thr Gly Gln Asp Gly Ser Tyr
```

-continued

```
           1               5              10              15
ctc gcc gag cta cta ctg agc aag gga tac gag gtt cac ggg ctc gtt      96
Leu Ala Glu Leu Leu Leu Ser Lys Gly Tyr Glu Val His Gly Leu Val
                    20              25              30 cgt cga gct tcg acg ttt aac acg tcg cgg atc gat cac ctc tac gtt     144
Arg Arg Ala Ser Thr Phe Asn Thr Ser Arg Ile Asp His Leu Tyr Val
                35              40              45 gac cca cac caa ccg ggc gcg cgc ttg ttc ttg cac tat gca gac ctc     192
Asp Pro His Gln Pro Gly Ala Arg Leu Phe Leu His Tyr Ala Asp Leu
            50              55              60 act gac ggc acc cgg ttg gtg acc ctg ctc agc agt atc gac ccg gat     240
Thr Asp Gly Thr Arg Leu Val Thr Leu Leu Ser Ser Ile Asp Pro Asp
65              70              75              80 gag gtc tac aac ctc gca gcg cag tcc cat gtg cgc gtc agc ttt gac     288
Glu Val Tyr Asn Leu Ala Ala Gln Ser His Val Arg Val Ser Phe Asp
                85              90              95 gag cca gtg cat acc gga gac acc acc ggc atg gga tcg atc cga ctt     336
Glu Pro Val His Thr Gly Asp Thr Thr Gly Met Gly Ser Ile Arg Leu
            100             105             110 ctg gaa gca gtc cgc ctt tct cgg gtg gac tgc cgg ttc tat cag gct     384
Leu Glu Ala Val Arg Leu Ser Arg Val Asp Cys Arg Phe Tyr Gln Ala
                115             120             125 tcc tcg tcg gag atg ttc ggc gca tct ccg cca ccg cag aac gaa tcg     432
Ser Ser Ser Glu Met Phe Gly Ala Ser Pro Pro Pro Gln Asn Glu Ser
130             135             140 acg ccg ttc tat ccc cgt tcg cca tac ggc gcg gcc aag gtc ttc tcg     480
Thr Pro Phe Tyr Pro Arg Ser Pro Tyr Gly Ala Ala Lys Val Phe Ser
145             150             155             160 tac tgg acg act cgc aac tat cga gag gcg tac gga tta ttc gca gtg     528
Tyr Trp Thr Thr Arg Asn Tyr Arg Glu Ala Tyr Gly Leu Phe Ala Val
                165             170             175 aat ggc atc ttg ttc aac cat gag tcc ccc cgg cgc ggc gag act ttc     576
Asn Gly Ile Leu Phe Asn His Glu Ser Pro Arg Arg Gly Glu Thr Phe
            180             185             190 gtg acc cga aag atc acg cgt gcc gtg gcg cgc atc cga gct ggc gtc     624
Val Thr Arg Lys Ile Thr Arg Ala Val Ala Arg Ile Arg Ala Gly Val
                195             200             205 caa tcg gag gtc tat atg ggc aac ctc gat gcg atc cgc gac tgg ggc     672
Gln Ser Glu Val Tyr Met Gly Asn Leu Asp Ala Ile Arg Asp Trp Gly
210             215             220 tac gcg ccc gaa tat gtc gag ggg atg tgg agg atg ttg caa gcg cct     720
Tyr Ala Pro Glu Tyr Val Glu Gly Met Trp Arg Met Leu Gln Ala Pro
225             230             235             240 gaa cct gat gac tac gtc ctg gcg aca ggg cgt ggt tac acc gta cgt     768
Glu Pro Asp Asp Tyr Val Leu Ala Thr Gly Arg Gly Tyr Thr Val Arg
                245             250             255 gag ttc gct caa gct gct ttt gac cat gtc ggg ctc gac tgg caa aag     816
Glu Phe Ala Gln Ala Ala Phe Asp His Val Gly Leu Asp Trp Gln Lys
            260             265             270 cgc gtc aag ttt gac gac cgc tat ttg cgt ccc acc gag gtc gat tcg     864
Arg Val Lys Phe Asp Asp Arg Tyr Leu Arg Pro Thr Glu Val Asp Ser
                275             280             285 cta gta gga gat gcc gac aag gcg gcc cag tca ctc ggc tgg aaa gct     912
Leu Val Gly Asp Ala Asp Lys Ala Ala Gln Ser Leu Gly Trp Lys Ala
290             295             300 tcg gtt cat act ggt gaa ctc gcg cgc atc atg gtg gac gcg gac atc     960
Ser Val His Thr Gly Glu Leu Ala Arg Ile Met Val Asp Ala Asp Ile
305             310             315             320 gcc gcg ttg gag tgc gat ggc aca cca tgg atc gac acg ccg atg ttg    1008
```

Ala Ala Leu Glu Cys Asp Gly Thr Pro Trp Ile Asp Thr Pro Met Leu
            325                 330                 335 cct ggt tgg ggc aga gta agt tga                                    1032
Pro Gly Trp Gly Arg Val Ser
            340

<210> SEQ ID NO 10
<211> LENGTH: 343
<212> TYPE: PRT
<213> ORGANISM: Mycobacterium

<400> SEQUENCE: 10

Val Lys Arg Ala Leu Ile Thr Gly Ile Thr Gly Gln Asp Gly Ser Tyr
 1               5                  10                  15

Leu Ala Glu Leu Leu Ser Lys Gly Tyr Glu Val His Gly Leu Val
            20                  25                  30

Arg Arg Ala Ser Thr Phe Asn Thr Ser Arg Ile Asp His Leu Tyr Val
            35                  40                  45

Asp Pro His Gln Pro Gly Ala Arg Leu Phe Leu His Tyr Ala Asp Leu
        50                  55                  60

Thr Asp Gly Thr Arg Leu Val Thr Leu Leu Ser Ile Asp Pro Asp
 65                 70                  75                  80

Glu Val Tyr Asn Leu Ala Ala Gln Ser His Val Arg Val Ser Phe Asp
                85                  90                  95

Glu Pro Val His Thr Gly Asp Thr Thr Gly Met Gly Ser Ile Arg Leu
            100                 105                 110

Leu Glu Ala Val Arg Leu Ser Arg Val Asp Cys Arg Phe Tyr Gln Ala
        115                 120                 125

Ser Ser Ser Glu Met Phe Gly Ala Ser Pro Pro Gln Asn Glu Ser
130                 135                 140

Thr Pro Phe Tyr Pro Arg Ser Pro Tyr Gly Ala Ala Lys Val Phe Ser
145                 150                 155                 160

Tyr Trp Thr Thr Arg Asn Tyr Arg Glu Ala Tyr Gly Leu Phe Ala Val
                165                 170                 175

Asn Gly Ile Leu Phe Asn His Glu Ser Pro Arg Arg Gly Glu Thr Phe
            180                 185                 190

Val Thr Arg Lys Ile Thr Arg Ala Val Ala Arg Ile Arg Ala Gly Val
        195                 200                 205

Gln Ser Glu Val Tyr Met Gly Asn Leu Asp Ala Ile Arg Asp Trp Gly
210                 215                 220

Tyr Ala Pro Glu Tyr Val Glu Gly Met Trp Arg Met Leu Gln Ala Pro
225                 230                 235                 240

Glu Pro Asp Asp Tyr Val Leu Ala Thr Gly Arg Gly Tyr Thr Val Arg
                245                 250                 255

Glu Phe Ala Gln Ala Ala Phe Asp His Val Gly Leu Asp Trp Gln Lys
            260                 265                 270

Arg Val Lys Phe Asp Asp Arg Tyr Leu Arg Pro Thr Glu Val Asp Ser
        275                 280                 285

Leu Val Gly Asp Ala Asp Lys Ala Ala Gln Ser Leu Gly Trp Lys Ala
290                 295                 300

Ser Val His Thr Gly Glu Leu Ala Arg Ile Met Val Asp Ala Asp Ile
305                 310                 315                 320

Ala Ala Leu Glu Cys Asp Gly Thr Pro Trp Ile Asp Thr Pro Met Leu
                325                 330                 335

Pro Gly Trp Gly Arg Val Ser
            340

```
<210> SEQ ID NO 11
<211> LENGTH: 1032
<212> TYPE: DNA
<213> ORGANISM: Mycobacterium
<220> FEATURE:
<221> NAME/KEY: CDS
<222> LOCATION: (1)..(1029)

<400> SEQUENCE: 11 gtg aag cga gcg ctt ata aca ggg atc acg ggg cag gat ggt tcc tac      48
Val Lys Arg Ala Leu Ile Thr Gly Ile Thr Gly Gln Asp Gly Ser Tyr
 1               5                  10                  15 ctc gcc gag cta cta ctg agc aag gga tac gag gtt cac ggg ctc gtt      96
Leu Ala Glu Leu Leu Leu Ser Lys Gly Tyr Glu Val His Gly Leu Val
             20                  25                  30 cgt cga gct tcg acg ttt aac acg tcg cgg atc gat cac ctc tac gtt     144
Arg Arg Ala Ser Thr Phe Asn Thr Ser Arg Ile Asp His Leu Tyr Val
         35                  40                  45 gac cca cac caa ccg ggc gcg cgc ttg ttc ttg cac tat gca gac ctc     192
Asp Pro His Gln Pro Gly Ala Arg Leu Phe Leu His Tyr Ala Asp Leu
     50                  55                  60 act gac ggc acc cgg ttg gtg acc ctg ctc agc agt atc gac ccg gat     240
Thr Asp Gly Thr Arg Leu Val Thr Leu Leu Ser Ser Ile Asp Pro Asp
 65                  70                  75                  80 gag gtc tac aac ctc gca gcg cag tcc cat gtg cgc gtc agc ttt gac     288
Glu Val Tyr Asn Leu Ala Ala Gln Ser His Val Arg Val Ser Phe Asp
                 85                  90                  95 gag cca gtg cat acc gga gac acc acc ggc atg gga tcg atc cga ctt     336
Glu Pro Val His Thr Gly Asp Thr Thr Gly Met Gly Ser Ile Arg Leu
            100                 105                 110 ctg gaa gca gtc cgc ctt tct cgg gtg gac tgc cgg ttc tat cag gct     384
Leu Glu Ala Val Arg Leu Ser Arg Val Asp Cys Arg Phe Tyr Gln Ala
        115                 120                 125 tcc tcg tcg gag atg ttc ggc gca tct ccg cca ccg cag aac gaa tcg     432
Ser Ser Ser Glu Met Phe Gly Ala Ser Pro Pro Pro Gln Asn Glu Ser
    130                 135                 140 acg ccg ttc tat ccc cgt tcg cca tac ggc gcg gcc aag gtc ttc tcg     480
Thr Pro Phe Tyr Pro Arg Ser Pro Tyr Gly Ala Ala Lys Val Phe Ser
145                 150                 155                 160 tac tgg acg act cgc aac tat cga gag gcg tac gga tta ttc gca gtg     528
Tyr Trp Thr Thr Arg Asn Tyr Arg Glu Ala Tyr Gly Leu Phe Ala Val
                165                 170                 175 aat ggc atc ttg ttc aac cat gag tcc ccc cgg cgc ggc gag act ttc     576
Asn Gly Ile Leu Phe Asn His Glu Ser Pro Arg Arg Gly Glu Thr Phe
            180                 185                 190 gtg acc cga aag atc acg cgt gcc gtg gcg cgc atc cga gct ggc gtc     624
Val Thr Arg Lys Ile Thr Arg Ala Val Ala Arg Ile Arg Ala Gly Val
        195                 200                 205 caa tcg gag gtc tat atg ggc aac ctc gat gcg atc cgc gac tgg ggc     672
Gln Ser Glu Val Tyr Met Gly Asn Leu Asp Ala Ile Arg Asp Trp Gly
    210                 215                 220 tac gcg ccc gaa tat gtc gag ggg atg tgg agg atg ttg caa gcg cct     720
Tyr Ala Pro Glu Tyr Val Glu Gly Met Trp Arg Met Leu Gln Ala Pro
225                 230                 235                 240 gaa cct gat gac tac gtc ctg gcg aca ggg cgt ggt tac acc gta cgt     768
Glu Pro Asp Asp Tyr Val Leu Ala Thr Gly Arg Gly Tyr Thr Val Arg
                245                 250                 255 gag ttc gct caa gct gct ttt gac cac gtc ggg ctc gac tgg caa aag     816
Glu Phe Ala Gln Ala Ala Phe Asp His Val Gly Leu Asp Trp Gln Lys
```

```
                  260              265              270
cac gtc aag ttt gac gac cgc tat ttg cgc ccc acc gag gtc gat tcg      864
His Val Lys Phe Asp Asp Arg Tyr Leu Arg Pro Thr Glu Val Asp Ser
        275              280              285 cta gta gga gat gcc gac agg gcg gcc cag tca ctc ggc tgg aaa gct      912
Leu Val Gly Asp Ala Asp Arg Ala Ala Gln Ser Leu Gly Trp Lys Ala
290              295              300 tcg gtt cat act ggt gaa ctc gcg cgc atc atg gtg gac gcg gac atc      960
Ser Val His Thr Gly Glu Leu Ala Arg Ile Met Val Asp Ala Asp Ile
305              310              315              320 gcc gcg tcg gag tgc gat ggc aca cca tgg atc gac acg ccg atg ttg     1008
Ala Ala Ser Glu Cys Asp Gly Thr Pro Trp Ile Asp Thr Pro Met Leu
            325              330              335 cct ggt tgg ggc gga gta agt tga                                     1032
Pro Gly Trp Gly Gly Val Ser
            340
```

<210> SEQ ID NO 12
<211> LENGTH: 343
<212> TYPE: PRT
<213> ORGANISM: Mycobacterium

<400> SEQUENCE: 12

```
Val Lys Arg Ala Leu Ile Thr Gly Ile Thr Gly Gln Asp Gly Ser Tyr
 1               5                  10                  15

Leu Ala Glu Leu Leu Ser Lys Gly Tyr Glu Val His Gly Leu Val
            20                  25                  30

Arg Arg Ala Ser Thr Phe Asn Thr Ser Arg Ile Asp His Leu Tyr Val
        35                  40                  45

Asp Pro His Gln Pro Gly Ala Arg Leu Phe Leu His Tyr Ala Asp Leu
    50                  55                  60

Thr Asp Gly Thr Arg Leu Val Thr Leu Ser Ser Ile Asp Pro Asp
65                  70                  75                  80

Glu Val Tyr Asn Leu Ala Ala Gln Ser His Val Arg Val Ser Phe Asp
                85                  90                  95

Glu Pro Val His Thr Gly Asp Thr Thr Gly Met Gly Ser Ile Arg Leu
            100                 105                 110

Leu Glu Ala Val Arg Leu Ser Arg Val Asp Cys Arg Phe Tyr Gln Ala
        115                 120                 125

Ser Ser Ser Glu Met Phe Gly Ala Ser Pro Pro Gln Asn Glu Ser
    130                 135                 140

Thr Pro Phe Tyr Pro Arg Ser Pro Tyr Gly Ala Ala Lys Val Phe Ser
145                 150                 155                 160

Tyr Trp Thr Thr Arg Asn Tyr Arg Glu Ala Tyr Gly Leu Phe Ala Val
                165                 170                 175

Asn Gly Ile Leu Phe Asn His Glu Ser Pro Arg Arg Gly Glu Thr Phe
            180                 185                 190

Val Thr Arg Lys Ile Thr Arg Ala Val Ala Arg Ile Arg Ala Gly Val
        195                 200                 205

Gln Ser Glu Val Tyr Met Gly Asn Leu Asp Ala Ile Arg Asp Trp Gly
    210                 215                 220

Tyr Ala Pro Glu Tyr Val Glu Gly Met Trp Arg Met Leu Gln Ala Pro
225                 230                 235                 240

Glu Pro Asp Asp Tyr Val Leu Ala Thr Gly Arg Gly Tyr Thr Val Arg
                245                 250                 255

Glu Phe Ala Gln Ala Ala Phe Asp His Val Gly Leu Asp Trp Gln Lys
```

-continued

```
                260                 265                 270
His Val Lys Phe Asp Asp Arg Tyr Leu Arg Pro Thr Glu Val Asp Ser
            275                 280                 285

Leu Val Gly Asp Ala Asp Arg Ala Ala Gln Ser Leu Gly Trp Lys Ala
        290                 295                 300

Ser Val His Thr Gly Glu Leu Ala Arg Ile Met Val Asp Ala Asp Ile
305                 310                 315                 320

Ala Ala Ser Glu Cys Asp Gly Thr Pro Trp Ile Asp Thr Pro Met Leu
                325                 330                 335

Pro Gly Trp Gly Gly Val Ser
            340

<210> SEQ ID NO 13
<211> LENGTH: 1020
<212> TYPE: DNA
<213> ORGANISM: Mycobacterium
<220> FEATURE:
<221> NAME/KEY: CDS
<222> LOCATION: (1)..(1017)

<400> SEQUENCE: 13 gtg cga tgg cac acc atg gat cga cac gcc gat gtt gcc tgg ttg ggg      48
Val Arg Trp His Thr Met Asp Arg His Ala Asp Val Ala Trp Leu Gly
  1               5                  10                  15 cag agt aag ttg acg act aca cct ggg cct ctg gac cgc gca acg ccc      96
Gln Ser Lys Leu Thr Thr Thr Pro Gly Pro Leu Asp Arg Ala Thr Pro
             20                  25                  30 gtg tat atc gcc ggt cat cgg ggg ctg gtc ggc tca gcg ctc gta cgt     144
Val Tyr Ile Ala Gly His Arg Gly Leu Val Gly Ser Ala Leu Val Arg
         35                  40                  45 aga ttt gag gcc gag ggg ttc acc aat ctc att gtg cga tca cgc gat     192
Arg Phe Glu Ala Glu Gly Phe Thr Asn Leu Ile Val Arg Ser Arg Asp
     50                  55                  60 gag att gat ctg acg gac cga gcc gca acg ttt gat ttt gtg tct gag     240
Glu Ile Asp Leu Thr Asp Arg Ala Ala Thr Phe Asp Phe Val Ser Glu
 65                  70                  75                  80 aca aga cca cag gtg atc atc gat gcg gcc gca cgg gtc ggc ggc atc     288
Thr Arg Pro Gln Val Ile Ile Asp Ala Ala Ala Arg Val Gly Gly Ile
                 85                  90                  95 atg gcg aat aac acc tat ccc gcg gac ttc ttg tcc gaa aac ctc cga     336
Met Ala Asn Asn Thr Tyr Pro Ala Asp Phe Leu Ser Glu Asn Leu Arg
            100                 105                 110 atc cag acc aat ttg ctc gac gca gct gtc gcc gtg cgt gtg ccg cgg     384
Ile Gln Thr Asn Leu Leu Asp Ala Ala Val Ala Val Arg Val Pro Arg
        115                 120                 125 ctc ctt ttc ctc ggt tcg tca tgc atc tac ccg aag tac gct ccg caa     432
Leu Leu Phe Leu Gly Ser Ser Cys Ile Tyr Pro Lys Tyr Ala Pro Gln
    130                 135                 140 cct atc cac gag agt gct tta ttg act ggc cct ttg gag ccc acc aac     480
Pro Ile His Glu Ser Ala Leu Leu Thr Gly Pro Leu Glu Pro Thr Asn
145                 150                 155                 160 gac gcg tat gcg atc gcc aag atc gcc ggt atc ctg caa gtt cag gcg     528
Asp Ala Tyr Ala Ile Ala Lys Ile Ala Gly Ile Leu Gln Val Gln Ala
                165                 170                 175 gtt agg cgc caa tat ggg ctg gcg tgg atc tct gcg atg ccg act aac     576
Val Arg Arg Gln Tyr Gly Leu Ala Trp Ile Ser Ala Met Pro Thr Asn
            180                 185                 190 ctc tac gga ccc ggc gac aac ttc tcc ccg tcc ggg tcg cat ctc ttg     624
Leu Tyr Gly Pro Gly Asp Asn Phe Ser Pro Ser Gly Ser His Leu Leu
        195                 200                 205
```

```
ccg gcg ctc atc cgt cga tat gag gaa gcc aaa gct ggt ggt gca gaa    672
Pro Ala Leu Ile Arg Arg Tyr Glu Glu Ala Lys Ala Gly Gly Ala Glu
    210                 215                 220 gag gtg acg aat tgg ggg acc ggt act ccg cgg cgc gaa ctt ctg cat    720
Glu Val Thr Asn Trp Gly Thr Gly Thr Pro Arg Arg Glu Leu Leu His
225                 230                 235                 240 gtc gac gat ctg gcg agc gca tgc ctg ttc ctt ttg gaa cat ttc gat    768
Val Asp Asp Leu Ala Ser Ala Cys Leu Phe Leu Leu Glu His Phe Asp
                245                 250                 255 ggt ccg aac cac gtc aac gtg ggc acc ggc gtc gat cac agc att agc    816
Gly Pro Asn His Val Asn Val Gly Thr Gly Val Asp His Ser Ile Ser
            260                 265                 270 gag atc gca gac atg gtc gct aca gcg gtg ggc tac atc ggc gaa aca    864
Glu Ile Ala Asp Met Val Ala Thr Ala Val Gly Tyr Ile Gly Glu Thr
        275                 280                 285 cgt tgg gat cca act aaa ccc gat gga acc ccg cgc aaa cta ttg gac    912
Arg Trp Asp Pro Thr Lys Pro Asp Gly Thr Pro Arg Lys Leu Leu Asp
    290                 295                 300 gtc tcc gcg cta cgc gag ttg ggt tgg cgc ccg cga atc gca ctg aaa    960
Val Ser Ala Leu Arg Glu Leu Gly Trp Arg Pro Arg Ile Ala Leu Lys
305                 310                 315                 320 gac ggc atc gat gca acg gtg tcg tgg tac cgc aca aat gcc gat gcc   1008
Asp Gly Ile Asp Ala Thr Val Ser Trp Tyr Arg Thr Asn Ala Asp Ala
                325                 330                 335 gtg agg agg taa                                                   1020
Val Arg Arg <210> SEQ ID NO 14
<211> LENGTH: 339
<212> TYPE: PRT
<213> ORGANISM: Mycobacterium

<400> SEQUENCE: 14

Val Arg Trp His Thr Met Asp Arg His Ala Asp Val Ala Trp Leu Gly
1               5                   10                  15

Gln Ser Lys Leu Thr Thr Thr Pro Gly Pro Leu Asp Arg Ala Thr Pro
            20                  25                  30

Val Tyr Ile Ala Gly His Arg Gly Leu Val Gly Ser Ala Leu Val Arg
        35                  40                  45

Arg Phe Glu Ala Glu Gly Phe Thr Asn Leu Ile Val Arg Ser Arg Asp
    50                  55                  60

Glu Ile Asp Leu Thr Asp Arg Ala Ala Thr Phe Asp Phe Val Ser Glu
65                  70                  75                  80

Thr Arg Pro Gln Val Ile Ile Asp Ala Ala Arg Val Gly Gly Ile
            85                  90                  95

Met Ala Asn Asn Thr Tyr Pro Ala Asp Phe Leu Ser Glu Asn Leu Arg
            100                 105                 110

Ile Gln Thr Asn Leu Leu Asp Ala Val Ala Val Arg Val Pro Arg
        115                 120                 125

Leu Leu Phe Leu Gly Ser Ser Cys Ile Tyr Pro Lys Tyr Ala Pro Gln
    130                 135                 140

Pro Ile His Glu Ser Ala Leu Leu Thr Gly Pro Leu Glu Pro Thr Asn
145                 150                 155                 160

Asp Ala Tyr Ala Ile Ala Lys Ile Ala Gly Ile Leu Gln Val Gln Ala
                165                 170                 175

Val Arg Arg Gln Tyr Gly Leu Ala Trp Ile Ser Ala Met Pro Thr Asn
            180                 185                 190
```

```
Leu Tyr Gly Pro Gly Asp Asn Phe Ser Pro Ser Gly Ser His Leu Leu
            195                 200                 205

Pro Ala Leu Ile Arg Arg Tyr Glu Glu Ala Lys Ala Gly Gly Ala Glu
    210                 215                 220

Glu Val Thr Asn Trp Gly Thr Gly Thr Pro Arg Arg Glu Leu Leu His
225                 230                 235                 240

Val Asp Asp Leu Ala Ser Ala Cys Leu Phe Leu Leu Glu His Phe Asp
                245                 250                 255

Gly Pro Asn His Val Asn Val Gly Thr Gly Val Asp His Ser Ile Ser
            260                 265                 270

Glu Ile Ala Asp Met Val Ala Thr Ala Val Gly Tyr Ile Gly Glu Thr
        275                 280                 285

Arg Trp Asp Pro Thr Lys Pro Asp Gly Thr Pro Arg Lys Leu Leu Asp
    290                 295                 300

Val Ser Ala Leu Arg Glu Leu Gly Trp Arg Pro Arg Ile Ala Leu Lys
305                 310                 315                 320

Asp Gly Ile Asp Ala Thr Val Ser Trp Tyr Arg Thr Asn Ala Asp Ala
                325                 330                 335

Val Arg Arg

<210> SEQ ID NO 15
<211> LENGTH: 1020
<212> TYPE: DNA
<213> ORGANISM: Mycobacterium
<220> FEATURE:
<221> NAME/KEY: CDS
<222> LOCATION: (1)..(1017)

<400> SEQUENCE: 15 gtg cga tgg cac acc atg gat cga cac gcc gat gtt gcc tgg ttg ggg      48
Val Arg Trp His Thr Met Asp Arg His Ala Asp Val Ala Trp Leu Gly
 1               5                  10                  15 cgg agt aag ttg acg act aca cct ggg cct ctg gac cgc gca acg ccc      96
Arg Ser Lys Leu Thr Thr Thr Pro Gly Pro Leu Asp Arg Ala Thr Pro
             20                  25                  30 gtg tat atc gcc ggt cat cgg ggg ctg gtc ggc tca gcg ctc gta cgt     144
Val Tyr Ile Ala Gly His Arg Gly Leu Val Gly Ser Ala Leu Val Arg
         35                  40                  45 aga ttt gag gcc gag ggg ttc acc aat ctc att gtg cga tca cgc gat     192
Arg Phe Glu Ala Glu Gly Phe Thr Asn Leu Ile Val Arg Ser Arg Asp
     50                  55                  60 gag att gat ctg acg gac cga gcc gca acg ttt gat ttt gtg tct gag     240
Glu Ile Asp Leu Thr Asp Arg Ala Ala Thr Phe Asp Phe Val Ser Glu
 65                  70                  75                  80 aca aga cca cag gtg atc atc gat gcg gcc gca cgg gtc ggc ggc atc     288
Thr Arg Pro Gln Val Ile Ile Asp Ala Ala Ala Arg Val Gly Gly Ile
                 85                  90                  95 atg gcg aat aac acc tat ccc gcg gac ttc ttg tcc gaa aac ctc cga     336
Met Ala Asn Asn Thr Tyr Pro Ala Asp Phe Leu Ser Glu Asn Leu Arg
            100                 105                 110 atc cag acc aat ttg ctc gac gca gct gtc gcc gtg cgt gtg ccg cgg     384
Ile Gln Thr Asn Leu Leu Asp Ala Ala Val Ala Val Arg Val Pro Arg
        115                 120                 125 ctc ctt ttc ctc ggt tcg tca tgc atc tac ccg aag tac gct ccg caa     432
Leu Leu Phe Leu Gly Ser Ser Cys Ile Tyr Pro Lys Tyr Ala Pro Gln
    130                 135                 140 cct atc cac gag agt gct tta ttg act ggc cct ttg gag ccc acc aac     480
Pro Ile His Glu Ser Ala Leu Leu Thr Gly Pro Leu Glu Pro Thr Asn
```

```
                145                 150                 155                 160
gac gcg tat gcg atc gcc aag atc gcc ggt atc ctg caa gtt cag gcg        528
Asp Ala Tyr Ala Ile Ala Lys Ile Ala Gly Ile Leu Gln Val Gln Ala
                165                 170                 175 gtt agg cgc caa tat ggg ctg gcg tgg atc tct gcg atg ccg act aac        576
Val Arg Arg Gln Tyr Gly Leu Ala Trp Ile Ser Ala Met Pro Thr Asn
                180                 185                 190 ctc tac gga ccc ggc gac aac ttc tcc ccg tcc ggg tcg cat ctc ttg        624
Leu Tyr Gly Pro Gly Asp Asn Phe Ser Pro Ser Gly Ser His Leu Leu
                195                 200                 205 ccg gcg ctc atc cgt cga tat gag gaa gcc aaa gct ggt ggt gca gaa        672
Pro Ala Leu Ile Arg Arg Tyr Glu Glu Ala Lys Ala Gly Gly Ala Glu
                210                 215                 220 gag gtg acg aat tgg ggg acc ggt act ccg cgg cgc gaa ctt ctg cat        720
Glu Val Thr Asn Trp Gly Thr Gly Thr Pro Arg Arg Glu Leu Leu His
225                 230                 235                 240 gtc gac gat ctg gcg agc gca tgc ctg ttc ctt ttg gaa cat ttc gat        768
Val Asp Asp Leu Ala Ser Ala Cys Leu Phe Leu Leu Glu His Phe Asp
                245                 250                 255 ggt ccg aac cac gtc aac gtg ggc acc ggc gtc gat cac agc att agc        816
Gly Pro Asn His Val Asn Val Gly Thr Gly Val Asp His Ser Ile Ser
                260                 265                 270 gag atc gca gac atg gtc gct acg gcg gtg ggc tac atc ggc gaa aca        864
Glu Ile Ala Asp Met Val Ala Thr Ala Val Gly Tyr Ile Gly Glu Thr
                275                 280                 285 cgt tgg gat cca act aaa ccc gat gga acc ccg cgc aaa cta ttg gac        912
Arg Trp Asp Pro Thr Lys Pro Asp Gly Thr Pro Arg Lys Leu Leu Asp
                290                 295                 300 gtc tcc gcg cta cgc gag ttg ggt tgg cgc ccg cga atc gca ctg aaa        960
Val Ser Ala Leu Arg Glu Leu Gly Trp Arg Pro Arg Ile Ala Leu Lys
305                 310                 315                 320 gac ggc atc gat gca acg gtg tcg tgg tac cgc aca aat gcc gat gcc       1008
Asp Gly Ile Asp Ala Thr Val Ser Trp Tyr Arg Thr Asn Ala Asp Ala
                325                 330                 335 gtg agg agg taa                                                       1020
Val Arg Arg <210> SEQ ID NO 16
<211> LENGTH: 339
<212> TYPE: PRT
<213> ORGANISM: Mycobacterium

<400> SEQUENCE: 16

Val Arg Trp His Thr Met Asp Arg His Ala Asp Val Ala Trp Leu Gly
 1               5                  10                  15

Arg Ser Lys Leu Thr Thr Thr Pro Gly Pro Leu Asp Arg Ala Thr Pro
                20                  25                  30

Val Tyr Ile Ala Gly His Arg Gly Leu Val Gly Ser Ala Leu Val Arg
            35                  40                  45

Arg Phe Glu Ala Glu Gly Phe Thr Asn Leu Ile Val Arg Ser Arg Asp
        50                  55                  60

Glu Ile Asp Leu Thr Asp Arg Ala Ala Thr Phe Asp Phe Val Ser Glu
65                  70                  75                  80

Thr Arg Pro Gln Val Ile Ile Asp Ala Ala Arg Val Gly Gly Ile
                85                  90                  95

Met Ala Asn Asn Thr Tyr Pro Ala Asp Phe Leu Ser Glu Asn Leu Arg
            100                 105                 110

Ile Gln Thr Asn Leu Leu Asp Ala Ala Val Ala Val Arg Val Pro Arg
```

```
            115                 120                 125
Leu Leu Phe Leu Gly Ser Ser Cys Ile Tyr Pro Lys Tyr Ala Pro Gln
        130                 135                 140

Pro Ile His Glu Ser Ala Leu Leu Thr Gly Pro Leu Glu Pro Thr Asn
145                 150                 155                 160

Asp Ala Tyr Ala Ile Ala Lys Ile Ala Gly Ile Leu Gln Val Gln Ala
                165                 170                 175

Val Arg Arg Gln Tyr Gly Leu Ala Trp Ile Ser Ala Met Pro Thr Asn
            180                 185                 190

Leu Tyr Gly Pro Gly Asp Asn Phe Ser Pro Ser Gly Ser His Leu Leu
        195                 200                 205

Pro Ala Leu Ile Arg Arg Tyr Glu Glu Ala Lys Ala Gly Gly Ala Glu
    210                 215                 220

Glu Val Thr Asn Trp Gly Thr Gly Thr Pro Arg Arg Glu Leu Leu His
225                 230                 235                 240

Val Asp Asp Leu Ala Ser Ala Cys Leu Phe Leu Glu His Phe Asp
                245                 250                 255

Gly Pro Asn His Val Asn Val Gly Thr Gly Val Asp His Ser Ile Ser
            260                 265                 270

Glu Ile Ala Asp Met Val Ala Thr Ala Val Gly Tyr Ile Gly Glu Thr
        275                 280                 285

Arg Trp Asp Pro Thr Lys Pro Asp Gly Thr Pro Arg Lys Leu Leu Asp
    290                 295                 300

Val Ser Ala Leu Arg Glu Leu Gly Trp Arg Pro Arg Ile Ala Leu Lys
305                 310                 315                 320

Asp Gly Ile Asp Ala Thr Val Ser Trp Tyr Arg Thr Asn Ala Asp Ala
                325                 330                 335

Val Arg Arg

<210> SEQ ID NO 17
<211> LENGTH: 723
<212> TYPE: DNA
<213> ORGANISM: Mycobacterium
<220> FEATURE:
<221> NAME/KEY: CDS
<222> LOCATION: (1)..(720)

<400> SEQUENCE: 17 atg gat ttt ttg cgc aac gcc ggc ttg atg gct cgt aac gtt agt acc     48
Met Asp Phe Leu Arg Asn Ala Gly Leu Met Ala Arg Asn Val Ser Thr
  1               5                  10                  15 gag atg ctg cgc cac ttc gaa cga aag cgc cta tta gta aac caa ttc     96
Glu Met Leu Arg His Phe Glu Arg Lys Arg Leu Leu Val Asn Gln Phe
                 20                  25                  30 aaa gca tac gga gtc aac gtt gtt att gat gtc ggt gct aac tcc ggc    144
Lys Ala Tyr Gly Val Asn Val Val Ile Asp Val Gly Ala Asn Ser Gly
             35                  40                  45 cag ttc ggt agc gct ttg cgt cgt gca gga ttc aag agc cgt atc gtt    192
Gln Phe Gly Ser Ala Leu Arg Arg Ala Gly Phe Lys Ser Arg Ile Val
         50                  55                  60 tcc ttt gaa cct ctt tcg ggg cca ttt gcg caa cta acg cgc aag tcg    240
Ser Phe Glu Pro Leu Ser Gly Pro Phe Ala Gln Leu Thr Arg Lys Ser
 65                  70                  75                  80 gca tcg gat cca cta tgg gag tgt cac cag tat gcc cta ggc gac gcc    288
Ala Ser Asp Pro Leu Trp Glu Cys His Gln Tyr Ala Leu Gly Asp Ala
                 85                  90                  95 gat gag acg att acc atc aat gtg gca ggc aat gcg ggg gca agt agt    336
Asp Glu Thr Ile Thr Ile Asn Val Ala Gly Asn Ala Gly Ala Ser Ser
```

```
            Asp Glu Thr Ile Thr Ile Asn Val Ala Gly Asn Ala Gly Ala Ser Ser
                        100                 105                 110 tcc gtg ctg ccg atg ctt aaa agt cat caa gat gcc ttt cct ccc gcg        384
Ser Val Leu Pro Met Leu Lys Ser His Gln Asp Ala Phe Pro Pro Ala
            115                 120                 125 aat tat att ggc acc gaa gac gtt gca ata cac cgc ctt gat tcg gtt        432
Asn Tyr Ile Gly Thr Glu Asp Val Ala Ile His Arg Leu Asp Ser Val
            130                 135                 140 gca tca gaa ttt ctg aac cct acc gat gtt act ttc ctg aag atc gac        480
Ala Ser Glu Phe Leu Asn Pro Thr Asp Val Thr Phe Leu Lys Ile Asp
145                 150                 155                 160 gta cag ggt ttc gag aag cag gtt atc acg ggc agt aag tca acg ctt        528
Val Gln Gly Phe Glu Lys Gln Val Ile Thr Gly Ser Lys Ser Thr Leu
                165                 170                 175 aac gaa agc tgc gtc ggc atg caa ctc gaa ctt tct ttt att ccg ttg        576
Asn Glu Ser Cys Val Gly Met Gln Leu Glu Leu Ser Phe Ile Pro Leu
            180                 185                 190 tac gaa ggt gac atg ctg att cat gaa gcg ctt gaa ctt gtc tat tcc        624
Tyr Glu Gly Asp Met Leu Ile His Glu Ala Leu Glu Leu Val Tyr Ser
            195                 200                 205 cta ggt ttc aga ctg acg ggt ttg ttg ccc ggc ttt acg gat ccg cgc        672
Leu Gly Phe Arg Leu Thr Gly Leu Leu Pro Gly Phe Thr Asp Pro Arg
210                 215                 220 aat ggt cga atg ctt caa gct gac ggg att ttc ttc cgt ggg gac gat        720
Asn Gly Arg Met Leu Gln Ala Asp Gly Ile Phe Phe Arg Gly Asp Asp
225                 230                 235                 240 tga                                                                     723

<210> SEQ ID NO 18
<211> LENGTH: 240
<212> TYPE: PRT
<213> ORGANISM: Mycobacterium

<400> SEQUENCE: 18

Met Asp Phe Leu Arg Asn Ala Gly Leu Met Ala Arg Asn Val Ser Thr
 1               5                  10                  15

Glu Met Leu Arg His Phe Glu Arg Lys Arg Leu Leu Val Asn Gln Phe
            20                  25                  30

Lys Ala Tyr Gly Val Asn Val Val Ile Asp Val Gly Ala Asn Ser Gly
        35                  40                  45

Gln Phe Gly Ser Ala Leu Arg Arg Ala Gly Phe Lys Ser Arg Ile Val
    50                  55                  60

Ser Phe Glu Pro Leu Ser Gly Pro Phe Ala Gln Leu Thr Arg Lys Ser
65                  70                  75                  80

Ala Ser Asp Pro Leu Trp Glu Cys His Gln Tyr Ala Leu Gly Asp Ala
                85                  90                  95

Asp Glu Thr Ile Thr Ile Asn Val Ala Gly Asn Ala Gly Ala Ser Ser
            100                 105                 110

Ser Val Leu Pro Met Leu Lys Ser His Gln Asp Ala Phe Pro Pro Ala
        115                 120                 125

Asn Tyr Ile Gly Thr Glu Asp Val Ala Ile His Arg Leu Asp Ser Val
    130                 135                 140

Ala Ser Glu Phe Leu Asn Pro Thr Asp Val Thr Phe Leu Lys Ile Asp
145                 150                 155                 160

Val Gln Gly Phe Glu Lys Gln Val Ile Thr Gly Ser Lys Ser Thr Leu
                165                 170                 175

Asn Glu Ser Cys Val Gly Met Gln Leu Glu Leu Ser Phe Ile Pro Leu
```

```
                    180              185                 190
Tyr Glu Gly Asp Met Leu Ile His Glu Ala Leu Glu Leu Val Tyr Ser
            195                 200                 205

Leu Gly Phe Arg Leu Thr Gly Leu Leu Pro Gly Phe Thr Asp Pro Arg
        210                 215                 220

Asn Gly Arg Met Leu Gln Ala Asp Gly Ile Phe Phe Arg Gly Asp Asp
225                 230                 235                 240

<210> SEQ ID NO 19
<211> LENGTH: 723
<212> TYPE: DNA
<213> ORGANISM: Mycobacterium
<220> FEATURE:
<221> NAME/KEY: CDS
<222> LOCATION: (1)..(720)

<400> SEQUENCE: 19 atg gat ttt ttg cgc aac gcc ggc ttg atg gct cgt aac gtt agc acc    48
Met Asp Phe Leu Arg Asn Ala Gly Leu Met Ala Arg Asn Val Ser Thr
 1               5                  10                  15 gag atg ctg cgc cac ttc gaa cga aag cgc cta tta gta aac caa ttc    96
Glu Met Leu Arg His Phe Glu Arg Lys Arg Leu Leu Val Asn Gln Phe
            20                  25                  30 aaa gca tac gga gtc aac gtt gtt att gat gtc ggt gct aac tcc ggc   144
Lys Ala Tyr Gly Val Asn Val Val Ile Asp Val Gly Ala Asn Ser Gly
        35                  40                  45 cag ttc ggt agc gct ttg cgt cgt gca gga ttc aag agc cgt atc gtt   192
Gln Phe Gly Ser Ala Leu Arg Arg Ala Gly Phe Lys Ser Arg Ile Val
    50                  55                  60 tcc ttt gaa cct ctt tcg ggg cca ttt gcg caa cta acg cgc gag tcg   240
Ser Phe Glu Pro Leu Ser Gly Pro Phe Ala Gln Leu Thr Arg Glu Ser
65                  70                  75                  80 gca tcg gat cca cta tgg gag tgt cac cag tat gcc cta ggc gac gcc   288
Ala Ser Asp Pro Leu Trp Glu Cys His Gln Tyr Ala Leu Gly Asp Ala
                85                  90                  95 gat gag acg att acc atc aat gtg gca ggc aat gcg ggg gca agt agt   336
Asp Glu Thr Ile Thr Ile Asn Val Ala Gly Asn Ala Gly Ala Ser Ser
            100                 105                 110 tcc gtg ctg ccg atg ctt aaa agt cat caa gat gcc ttt cct ccc gcg   384
Ser Val Leu Pro Met Leu Lys Ser His Gln Asp Ala Phe Pro Pro Ala
        115                 120                 125 aat tat att ggc acc gaa gac gtt gca ata cac cgc ctt gat tcg gtt   432
Asn Tyr Ile Gly Thr Glu Asp Val Ala Ile His Arg Leu Asp Ser Val
    130                 135                 140 gca tca gaa ttt ctg aac cct acc gat gtt act ttc ctg aag atc gac   480
Ala Ser Glu Phe Leu Asn Pro Thr Asp Val Thr Phe Leu Lys Ile Asp
145                 150                 155                 160 gta cag ggt ttc gag aag cag gtt atc gcg ggc agt aag tca acg ctt   528
Val Gln Gly Phe Glu Lys Gln Val Ile Ala Gly Ser Lys Ser Thr Leu
                165                 170                 175 aac gaa agc tgc gtc ggc atg caa ctc gaa ctt tct ttt att ccg ttg   576
Asn Glu Ser Cys Val Gly Met Gln Leu Glu Leu Ser Phe Ile Pro Leu
            180                 185                 190 tac gaa ggt gac atg ctg att cat gaa gcg ctt gaa ctt gtc tat tcc   624
Tyr Glu Gly Asp Met Leu Ile His Glu Ala Leu Glu Leu Val Tyr Ser
        195                 200                 205 cta ggt ttc aga ctg acg ggt ttg ttg ccc gga ttt acg gat ccg cgc   672
Leu Gly Phe Arg Leu Thr Gly Leu Leu Pro Gly Phe Thr Asp Pro Arg
    210                 215                 220 aat ggt cga atg ctt caa gct gac ggc att ttc ttc cgt ggg gac gat   720
Asn Gly Arg Met Leu Gln Ala Asp Gly Ile Phe Phe Arg Gly Asp Asp
225                 230                 235                 240
```

```
Asn Gly Arg Met Leu Gln Ala Asp Gly Ile Phe Phe Arg Gly Asp Asp
225                 230                 235                 240 tga                                                                     723

<210> SEQ ID NO 20
<211> LENGTH: 240
<212> TYPE: PRT
<213> ORGANISM: Mycobacterium

<400> SEQUENCE: 20

Met Asp Phe Leu Arg Asn Ala Gly Leu Met Ala Arg Asn Val Ser Thr
 1               5                  10                  15

Glu Met Leu Arg His Phe Glu Arg Lys Arg Leu Leu Val Asn Gln Phe
             20                  25                  30

Lys Ala Tyr Gly Val Asn Val Ile Asp Val Gly Ala Asn Ser Gly
         35                  40                  45

Gln Phe Gly Ser Ala Leu Arg Arg Ala Gly Phe Lys Ser Arg Ile Val
     50                  55                  60

Ser Phe Glu Pro Leu Ser Gly Pro Phe Ala Gln Leu Thr Arg Glu Ser
 65                  70                  75                  80

Ala Ser Asp Pro Leu Trp Glu Cys His Gln Tyr Ala Leu Gly Asp Ala
                 85                  90                  95

Asp Glu Thr Ile Thr Ile Asn Val Ala Gly Asn Ala Gly Ala Ser Ser
            100                 105                 110

Ser Val Leu Pro Met Leu Lys Ser His Gln Asp Ala Phe Pro Pro Ala
        115                 120                 125

Asn Tyr Ile Gly Thr Glu Asp Val Ala Ile His Arg Leu Asp Ser Val
    130                 135                 140

Ala Ser Glu Phe Leu Asn Pro Thr Asp Val Thr Phe Leu Lys Ile Asp
145                 150                 155                 160

Val Gln Gly Phe Glu Lys Gln Val Ile Ala Gly Ser Lys Ser Thr Leu
                165                 170                 175

Asn Glu Ser Cys Val Gly Met Gln Leu Glu Leu Ser Phe Ile Pro Leu
            180                 185                 190

Tyr Glu Gly Asp Met Leu Ile His Glu Ala Leu Glu Leu Val Tyr Ser
        195                 200                 205

Leu Gly Phe Arg Leu Thr Gly Leu Leu Pro Gly Phe Thr Asp Pro Arg
    210                 215                 220

Asn Gly Arg Met Leu Gln Ala Asp Gly Ile Phe Phe Arg Gly Asp Asp
225                 230                 235                 240

<210> SEQ ID NO 21
<211> LENGTH: 801
<212> TYPE: DNA
<213> ORGANISM: Mycobacterium
<220> FEATURE:
<221> NAME/KEY: CDS
<222> LOCATION: (1)..(798)

<400> SEQUENCE: 21 atg act gcg cca gtg ttc tcg ata att atc cct acc ttc aat gca gcg    48
Met Thr Ala Pro Val Phe Ser Ile Ile Ile Pro Thr Phe Asn Ala Ala
 1               5                  10                  15 gtg acg ctg caa gcc tgc ctc gga agc atc gtc ggg cag acc tac cgg    96
Val Thr Leu Gln Ala Cys Leu Gly Ser Ile Val Gly Gln Thr Tyr Arg
             20                  25                  30 gaa gtg gaa gtg gtc ctt gtc gac ggc ggt tcg acc gat cgg acc ctc   144
Glu Val Glu Val Val Leu Val Asp Gly Gly Ser Thr Asp Arg Thr Leu
```

-continued

```
              35                  40                  45
gac atc gcg aac agt ttc cgc ccg gaa ctc ggc tcg cga ctg gtc gtt      192
Asp Ile Ala Asn Ser Phe Arg Pro Glu Leu Gly Ser Arg Leu Val Val
     50                  55                  60 cac agc ggg ccc gat gat ggc ccc tac gac gcc atg aac cgc ggc gtc      240
His Ser Gly Pro Asp Asp Gly Pro Tyr Asp Ala Met Asn Arg Gly Val
 65                  70                  75                  80 ggc gtg gcc aca ggc gaa tgg gta ctt ttt tta ggc gcc gac gac acc      288
Gly Val Ala Thr Gly Glu Trp Val Leu Phe Leu Gly Ala Asp Asp Thr
                 85                  90                  95 ctc tac gaa cca acc acg ttg gcc cag gta gcc gct ttt ctc ggc gac      336
Leu Tyr Glu Pro Thr Thr Leu Ala Gln Val Ala Ala Phe Leu Gly Asp
            100                 105                 110 cat gcg gca agc cat ctt gtc tat ggc gat gtt gtg atg cgt tcg acg      384
His Ala Ala Ser His Leu Val Tyr Gly Asp Val Val Met Arg Ser Thr
        115                 120                 125 aaa agc cgg cat gcc gga cct ttc gac ctc gac cgc ctc cta ttt gag      432
Lys Ser Arg His Ala Gly Pro Phe Asp Leu Asp Arg Leu Leu Phe Glu
    130                 135                 140 acg aat ttg tgc cac caa tcg atc ttt tac cgc gtg gag ctt ttc gac      480
Thr Asn Leu Cys His Gln Ser Ile Phe Tyr Arg Arg Glu Leu Phe Asp
145                 150                 155                 160 ggc atc ggc cct tac aac ctg cgc tac cga gtc tgg gcg gac tgg gac      528
Gly Ile Gly Pro Tyr Asn Leu Arg Tyr Arg Val Trp Ala Asp Trp Asp
                165                 170                 175 ttc aat att cgc tgc ttc tcc aac ccg gcg ctg att acc cgc tac atg      576
Phe Asn Ile Arg Cys Phe Ser Asn Pro Ala Leu Ile Thr Arg Tyr Met
            180                 185                 190 gac gtc gtg att tcc gaa tac aac gac atg acc ggc ttc agc atg agg      624
Asp Val Val Ile Ser Glu Tyr Asn Asp Met Thr Gly Phe Ser Met Arg
        195                 200                 205 cag ggg act gat aaa gag ttc aga aaa cgg ctg cca atg tac ttc tgg      672
Gln Gly Thr Asp Lys Glu Phe Arg Lys Arg Leu Pro Met Tyr Phe Trp
    210                 215                 220 gtt gca ggg tgg gag act tgc agg cgc atg ctg gcg ttt ttg aaa gac      720
Val Ala Gly Trp Glu Thr Cys Arg Arg Met Leu Ala Phe Leu Lys Asp
225                 230                 235                 240 aag gag aat cgc cgt ctg gcc ttg cgt acg cgg ttg ata agg gtt aag      768
Lys Glu Asn Arg Arg Leu Ala Leu Arg Thr Arg Leu Ile Arg Val Lys
                245                 250                 255 gcc gtc tcc aaa gaa cga agc gca gaa ccg tag                          801
Ala Val Ser Lys Glu Arg Ser Ala Glu Pro
            260                 265

<210> SEQ ID NO 22
<211> LENGTH: 266
<212> TYPE: PRT
<213> ORGANISM: Mycobacterium

<400> SEQUENCE: 22

Met Thr Ala Pro Val Phe Ser Ile Ile Pro Thr Phe Asn Ala Ala
  1               5                  10                  15

Val Thr Leu Gln Ala Cys Leu Gly Ser Ile Val Gly Gln Thr Tyr Arg
             20                  25                  30

Glu Val Glu Val Val Leu Val Asp Gly Gly Ser Thr Asp Arg Thr Leu
         35                  40                  45

Asp Ile Ala Asn Ser Phe Arg Pro Glu Leu Gly Ser Arg Leu Val Val
     50                  55                  60

His Ser Gly Pro Asp Asp Gly Pro Tyr Asp Ala Met Asn Arg Gly Val
```

```
                65                  70                  75                  80
Gly Val Ala Thr Gly Glu Trp Val Leu Phe Leu Gly Ala Asp Asp Thr
                    85                  90                  95

Leu Tyr Glu Pro Thr Thr Leu Ala Gln Val Ala Ala Phe Leu Gly Asp
                100                 105                 110

His Ala Ala Ser His Leu Val Tyr Gly Asp Val Val Met Arg Ser Thr
                115                 120                 125

Lys Ser Arg His Ala Gly Pro Phe Asp Leu Asp Arg Leu Leu Phe Glu
        130                 135                 140

Thr Asn Leu Cys His Gln Ser Ile Phe Tyr Arg Arg Glu Leu Phe Asp
145                 150                 155                 160

Gly Ile Gly Pro Tyr Asn Leu Arg Tyr Arg Val Trp Ala Asp Trp Asp
                165                 170                 175

Phe Asn Ile Arg Cys Phe Ser Asn Pro Ala Leu Ile Thr Arg Tyr Met
                180                 185                 190

Asp Val Val Ile Ser Glu Tyr Asn Asp Met Thr Gly Phe Ser Met Arg
                195                 200                 205

Gln Gly Thr Asp Lys Glu Phe Arg Lys Arg Leu Pro Met Tyr Phe Trp
        210                 215                 220

Val Ala Gly Trp Glu Thr Cys Arg Arg Met Leu Ala Phe Leu Lys Asp
225                 230                 235                 240

Lys Glu Asn Arg Arg Leu Ala Leu Arg Thr Arg Leu Ile Arg Val Lys
                245                 250                 255

Ala Val Ser Lys Glu Arg Ser Ala Glu Pro
                260                 265

<210> SEQ ID NO 23
<211> LENGTH: 801
<212> TYPE: DNA
<213> ORGANISM: Mycobacterium
<220> FEATURE:
<221> NAME/KEY: CDS
<222> LOCATION: (1)..(798)

<400> SEQUENCE: 23 atg act gcg cca gtg ttc tcg ata att atc cct acc ttc aat gca gcg      48
Met Thr Ala Pro Val Phe Ser Ile Ile Ile Pro Thr Phe Asn Ala Ala
 1               5                  10                  15 gtg acg ctg caa gcc tgc ctc gga agc atc gtc ggg cag acc tac cgg      96
Val Thr Leu Gln Ala Cys Leu Gly Ser Ile Val Gly Gln Thr Tyr Arg
                20                  25                  30 gaa gtg gaa gtg gtc ctt gtc gac ggc ggt tcg acc gat cgg acc ctc     144
Glu Val Glu Val Val Leu Val Asp Gly Gly Ser Thr Asp Arg Thr Leu
            35                  40                  45 gac atc gcg aac agt ttc cgc ccg gaa ctc ggc tcg cga ctg gtc gtt     192
Asp Ile Ala Asn Ser Phe Arg Pro Glu Leu Gly Ser Arg Leu Val Val
     50                  55                  60 cac agc ggg ccc gat gat ggc ccc tac gac gcc atg aac cgc ggc gtc     240
His Ser Gly Pro Asp Asp Gly Pro Tyr Asp Ala Met Asn Arg Gly Val
 65                  70                  75                  80 ggc gta gcc aca ggc gaa tgg gta ctt ttt tta ggc gcc gac gac acc     288
Gly Val Ala Thr Gly Glu Trp Val Leu Phe Leu Gly Ala Asp Asp Thr
                85                  90                  95 ctc tac gaa cca acc acg ttg gcc cag gta gcc gct ttt ctc ggc gac     336
Leu Tyr Glu Pro Thr Thr Leu Ala Gln Val Ala Ala Phe Leu Gly Asp
                100                 105                 110 cat gcg gca agc cat ctt gtc tat ggc gat gtt gtg atg cgt tcg acg     384
His Ala Ala Ser His Leu Val Tyr Gly Asp Val Val Met Arg Ser Thr
                115                 120                 125
```

```
aaa agc cgg cat gcc gga cct ttc gac ctc gac cgc ctc cta ttt gag       432
Lys Ser Arg His Ala Gly Pro Phe Asp Leu Asp Arg Leu Leu Phe Glu
    130                 135                 140 acg aat ttg tgc cac caa tcg atc ttt tac cgc cgt gag ctt ttc gac       480
Thr Asn Leu Cys His Gln Ser Ile Phe Tyr Arg Arg Glu Leu Phe Asp
145                 150                 155                 160 ggc atc ggc cct tac aac ctg cgc tac cga gtc tgg gcg gac tgg gac       528
Gly Ile Gly Pro Tyr Asn Leu Arg Tyr Arg Val Trp Ala Asp Trp Asp
                165                 170                 175 ttc aat att cgc tgc ttc tcc aac ccg gcg ctg att acc cgc tac atg       576
Phe Asn Ile Arg Cys Phe Ser Asn Pro Ala Leu Ile Thr Arg Tyr Met
            180                 185                 190 gac gtc gtg att tcc gaa tac aac gac atg acc ggc ttc agc atg agg       624
Asp Val Val Ile Ser Glu Tyr Asn Asp Met Thr Gly Phe Ser Met Arg
        195                 200                 205 cag ggg act gat aaa gag ttc aga aaa cgg ctg cca atg tac ttc tgg       672
Gln Gly Thr Asp Lys Glu Phe Arg Lys Arg Leu Pro Met Tyr Phe Trp
    210                 215                 220 gtt gca ggg tgg gag act tgc agg cgc atg ctg gcg ttt ttg aaa gac       720
Val Ala Gly Trp Glu Thr Cys Arg Arg Met Leu Ala Phe Leu Lys Asp
225                 230                 235                 240 aag gag aat cgc cgt ctg gcc ttg cgt acg cgg ttg ata agg gtt aag       768
Lys Glu Asn Arg Arg Leu Ala Leu Arg Thr Arg Leu Ile Arg Val Lys
                245                 250                 255 gcc gtc tcc aaa gaa cga agc gca gaa ccg tag                           801
Ala Val Ser Lys Glu Arg Ser Ala Glu Pro
            260                 265

<210> SEQ ID NO 24
<211> LENGTH: 266
<212> TYPE: PRT
<213> ORGANISM: Mycobacterium

<400> SEQUENCE: 24

Met Thr Ala Pro Val Phe Ser Ile Ile Pro Thr Phe Asn Ala Ala
 1               5                  10                  15

Val Thr Leu Gln Ala Cys Leu Gly Ser Ile Val Gly Gln Thr Tyr Arg
                20                  25                  30

Glu Val Glu Val Val Leu Val Asp Gly Gly Ser Thr Asp Arg Thr Leu
            35                  40                  45

Asp Ile Ala Asn Ser Phe Arg Pro Glu Leu Gly Ser Arg Leu Val Val
        50                  55                  60

His Ser Gly Pro Asp Gly Pro Tyr Asp Ala Met Asn Arg Gly Val
65                  70                  75                  80

Gly Val Ala Thr Gly Glu Trp Val Leu Phe Leu Gly Ala Asp Asp Thr
                85                  90                  95

Leu Tyr Glu Pro Thr Thr Leu Ala Gln Val Ala Ala Phe Leu Gly Asp
            100                 105                 110

His Ala Ala Ser His Leu Val Tyr Gly Asp Val Met Arg Ser Thr
        115                 120                 125

Lys Ser Arg His Ala Gly Pro Phe Asp Leu Asp Arg Leu Leu Phe Glu
    130                 135                 140

Thr Asn Leu Cys His Gln Ser Ile Phe Tyr Arg Arg Glu Leu Phe Asp
145                 150                 155                 160

Gly Ile Gly Pro Tyr Asn Leu Arg Tyr Arg Val Trp Ala Asp Trp Asp
                165                 170                 175
```

```
Phe Asn Ile Arg Cys Phe Ser Asn Pro Ala Leu Ile Thr Arg Tyr Met
            180                 185                 190

Asp Val Ile Ser Glu Tyr Asn Asp Met Thr Gly Phe Ser Met Arg
        195                 200                 205

Gln Gly Thr Asp Lys Glu Phe Arg Lys Arg Leu Pro Met Tyr Phe Trp
        210                 215                 220

Val Ala Gly Trp Glu Thr Cys Arg Arg Met Leu Ala Phe Leu Lys Asp
225                 230                 235                 240

Lys Glu Asn Arg Arg Leu Ala Leu Arg Thr Arg Leu Ile Arg Val Lys
                245                 250                 255

Ala Val Ser Lys Glu Arg Ser Ala Glu Pro
            260                 265
```

```
<210> SEQ ID NO 25
<211> LENGTH: 867
<212> TYPE: DNA
<213> ORGANISM: Mycobacterium
<220> FEATURE:
<221> NAME/KEY: CDS
<222> LOCATION: (1)..(864)

<400> SEQUENCE: 25
```

```
gtg gcc agc aga agt ccc cac tcc gct gcg ggt ggt tgg cta att ctt    48
Val Ala Ser Arg Ser Pro His Ser Ala Ala Gly Gly Trp Leu Ile Leu
 1               5                  10                  15 ggc ggc tcc ctt ctt gtg gtc ggc gtg gcg cat ccg gta gga ctc gcc    96
Gly Gly Ser Leu Leu Val Val Gly Val Ala His Pro Val Gly Leu Ala
            20                  25                  30 gga ggt gac gac gat gct ggc gtg gtg cag cag ccg atc gag gat gct   144
Gly Gly Asp Asp Asp Ala Gly Val Val Gln Gln Pro Ile Glu Asp Ala
        35                  40                  45 ggc ggc ggt ggt gtg ctc ggg cag gaa tcg ccc cca ttg ttc gaa ggg   192
Gly Gly Gly Gly Val Leu Gly Gln Glu Ser Pro Pro Leu Phe Glu Gly
    50                  55                  60 cca atg cga ggc gat ggc cag gga gcg gcg ctc gta gcc ggc agc cac   240
Pro Met Arg Gly Asp Gly Gln Gly Ala Ala Leu Val Ala Gly Ser His
 65                  70                  75                  80 gag ccg gaa caa cag ttg agt ccc ggt gtc gtc gag cgg ggc gaa gcc   288
Glu Pro Glu Gln Gln Leu Ser Pro Gly Val Val Glu Arg Gly Glu Ala
                 85                  90                  95 gat ctc gtc caa gat gac cag atc cgc gcg gag cag ggt gtc gat gat   336
Asp Leu Val Gln Asp Asp Gln Ile Arg Ala Glu Gln Gly Val Asp Asp
            100                 105                 110 ctt gcc gac ggt gtt gtc ggc cag gcc gcg gta gag gac ctc gat cag   384
Leu Ala Asp Gly Val Val Gly Gln Ala Ala Val Glu Asp Leu Asp Gln
        115                 120                 125 gtc ggc ggc ggt gaa gta gcg gac ttt gaa tcc ggc gtg gac ggc agc   432
Val Gly Gly Gly Glu Val Ala Asp Phe Glu Ser Gly Val Asp Gly Ser
    130                 135                 140 gtg ccc gca gcc gat gag cag gtg act ttt gcc cgt acc agg tgg gcc   480
Val Pro Ala Ala Asp Glu Gln Val Thr Phe Ala Arg Thr Arg Trp Ala
145                 150                 155                 160 aat gac cgc cag gtt ctg ttg tgc ccg aat cca ttc cag gct cga cag   528
Asn Asp Arg Gln Val Leu Leu Cys Pro Asn Pro Phe Gln Ala Arg Gln
                165                 170                 175 gta gtc gaa cgt ggc tgc ggt gat cga cga tcc ggt gac gtc gaa ccc   576
Val Val Glu Arg Gly Cys Gly Asp Arg Arg Ser Gly Asp Val Glu Pro
            180                 185                 190 gtc gag ggt ctt ggt gac cgg gaa ggc tgc ggc ctt gag acg gtt ggc   624
Val Glu Gly Leu Gly Asp Arg Glu Gly Cys Gly Leu Glu Thr Val Gly
```

-continued

```
                        195                 200                 205
ggt gtt gga ggc atc gcg ggc agc gat ctc ggc ctc aac caa cgt ccg         672
Gly Val Gly Gly Ile Ala Gly Ser Asp Leu Gly Leu Asn Gln Arg Pro
    210                 215                 220 cag gat ctc ctc cgg tgt cca gcg ttg cgt ctt ggc gac ttg caa cac         720
Gln Asp Leu Leu Arg Cys Pro Ala Leu Arg Leu Gly Asp Leu Gln His
225                 230                 235                 240 ctc ggc ggc gtt gcg gcg cac cgt ggc cag ctt caa ccg ccg cag cgc         768
Leu Gly Gly Val Ala Ala His Arg Gly Gln Leu Gln Pro Pro Gln Arg
                245                 250                 255 cgc gtc aag gtc agc agc cag cgg tgc cgc cga gga cgg tgc cac cgg         816
Arg Val Lys Val Ser Ser Gln Arg Cys Arg Arg Gly Arg Cys His Arg
            260                 265                 270 ctt ggc agc ggt ggt cat gag gcc gtc ccg tcg gtg gtg ttg atc ttg         864
Leu Gly Ser Gly Gly His Glu Ala Val Pro Ser Val Val Leu Ile Leu
        275                 280                 285 tag                                                                     867
```

<210> SEQ ID NO 26
<211> LENGTH: 288
<212> TYPE: PRT
<213> ORGANISM: Mycobacterium

<400> SEQUENCE: 26

```
Val Ala Ser Arg Ser Pro His Ser Ala Ala Gly Gly Trp Leu Ile Leu
  1               5                  10                  15

Gly Gly Ser Leu Leu Val Val Gly Val Ala His Pro Val Gly Leu Ala
             20                  25                  30

Gly Gly Asp Asp Asp Ala Gly Val Val Gln Gln Pro Ile Glu Asp Ala
         35                  40                  45

Gly Gly Gly Gly Val Leu Gly Gln Glu Ser Pro Pro Leu Phe Glu Gly
     50                  55                  60

Pro Met Arg Gly Asp Gly Gln Gly Ala Ala Leu Val Ala Gly Ser His
 65                  70                  75                  80

Glu Pro Glu Gln Gln Leu Ser Pro Gly Val Val Glu Arg Gly Glu Ala
                 85                  90                  95

Asp Leu Val Gln Asp Gln Ile Arg Ala Glu Gln Gly Val Asp Asp
            100                 105                 110

Leu Ala Asp Gly Val Val Gly Gln Ala Ala Val Glu Asp Leu Asp Gln
        115                 120                 125

Val Gly Gly Gly Glu Val Ala Asp Phe Glu Ser Gly Val Asp Gly Ser
    130                 135                 140

Val Pro Ala Ala Asp Glu Gln Val Thr Phe Ala Arg Thr Arg Trp Ala
145                 150                 155                 160

Asn Asp Arg Gln Val Leu Leu Cys Pro Asn Pro Phe Gln Ala Arg Gln
                165                 170                 175

Val Val Glu Arg Gly Cys Gly Asp Arg Ser Gly Asp Val Glu Pro
            180                 185                 190

Val Glu Gly Leu Gly Asp Arg Glu Gly Cys Gly Leu Glu Thr Val Gly
        195                 200                 205

Gly Val Gly Gly Ile Ala Gly Ser Asp Leu Gly Leu Asn Gln Arg Pro
    210                 215                 220

Gln Asp Leu Leu Arg Cys Pro Ala Leu Arg Leu Gly Asp Leu Gln His
225                 230                 235                 240

Leu Gly Gly Val Ala Ala His Arg Gly Gln Leu Gln Pro Pro Gln Arg
                245                 250                 255
```

```
Arg Val Lys Val Ser Ser Gln Arg Cys Arg Gly Arg Cys His Arg
            260                 265                 270

Leu Gly Ser Gly Gly His Glu Ala Val Pro Ser Val Val Leu Ile Leu
        275                 280                 285
```

<210> SEQ ID NO 27
<211> LENGTH: 1739
<212> TYPE: DNA
<213> ORGANISM: Mycobacterium
<220> FEATURE:
<221> NAME/KEY: CDS
<222> LOCATION: (1)..(945)

<400> SEQUENCE: 27

```
atg ggc tgc ctc aaa ggt ggt gtc gtc gcc aat gtt gtt gtt cca aca       48
Met Gly Cys Leu Lys Gly Gly Val Val Ala Asn Val Val Val Pro Thr
  1               5                  10                  15 ccg gat tat gtg cga ttc gcg tcc cac tat ggc ttc gtt ccg gac ttc       96
Pro Asp Tyr Val Arg Phe Ala Ser His Tyr Gly Phe Val Pro Asp Phe
             20                  25                  30 tgc cac ggt gcg gat ccg caa tcg aag ggc atc gtg gag aac ctc tgt      144
Cys His Gly Ala Asp Pro Gln Ser Lys Gly Ile Val Glu Asn Leu Cys
         35                  40                  45 ggc tac gct cag gac gac ctt gcg gtg ccg ctg ctg acc gaa gct gcg      192
Gly Tyr Ala Gln Asp Asp Leu Ala Val Pro Leu Leu Thr Glu Ala Ala
     50                  55                  60 tta gcc ggt gag cag gtc gac cta cgt gcc ctc aac gcc cag gcg caa      240
Leu Ala Gly Glu Gln Val Asp Leu Arg Ala Leu Asn Ala Gln Ala Gln
 65                  70                  75                  80 cta tgg tgc gcc gag gtc aat gcc acg gtc cac tcg gag atc tgc gcc      288
Leu Trp Cys Ala Glu Val Asn Ala Thr Val His Ser Glu Ile Cys Ala
                 85                  90                  95 gtg ccc aac gat cgc ttg gtt gac gag cgc acc gtc ttg agg gag ctg      336
Val Pro Asn Asp Arg Leu Val Asp Glu Arg Thr Val Leu Arg Glu Leu
            100                 105                 110 ccc tcg ctg cgg ccg acg atc ggc tcg ggg tcg gtg cgc cgt aag gtc      384
Pro Ser Leu Arg Pro Thr Ile Gly Ser Gly Ser Val Arg Arg Lys Val
        115                 120                 125 gac ggc ctc tcg tgc atc cgt tac ggc tca gct cgt tac tcg gtg cct      432
Asp Gly Leu Ser Cys Ile Arg Tyr Gly Ser Ala Arg Tyr Ser Val Pro
    130                 135                 140 cag cgg ctc gtc ggt gcc acc gtg gcg gtg gtg gtc gat cat ggc gcc      480
Gln Arg Leu Val Gly Ala Thr Val Ala Val Val Asp His Gly Ala
145                 150                 155                 160 ctg atc ctg ttg gaa cct gcg acc ggt gtg atc gtg gcc gag cac gag      528
Leu Ile Leu Leu Glu Pro Ala Thr Gly Val Ile Val Ala Glu His Glu
                165                 170                 175 ctc gtc agc cca ggt gag gtg tcc atc ctc gat gaa cac tac gac gga      576
Leu Val Ser Pro Gly Glu Val Ser Ile Leu Asp Glu His Tyr Asp Gly
            180                 185                 190 ccc aga ccc gca ccc tcg cgt ggt cct cgc ccg aaa acc caa gca gag      624
Pro Arg Pro Ala Pro Ser Arg Gly Pro Arg Pro Lys Thr Gln Ala Glu
        195                 200                 205 aaa cga ttc tgc gca ttg gga acc gaa gcg cag cag ttc ctc gtc ggt      672
Lys Arg Phe Cys Ala Leu Gly Thr Glu Ala Gln Gln Phe Leu Val Gly
    210                 215                 220 gct gcg gcg atc ggc aac acc cga ctg aaa tcc gaa ctc gac att ctg      720
Ala Ala Ala Ile Gly Asn Thr Arg Leu Lys Ser Glu Leu Asp Ile Leu
225                 230                 235                 240 ctc ggc ctt ggc gcc gcc cac ggc gaa cag gct ttg att gac gcg ctg      768
Leu Gly Leu Gly Ala Ala His Gly Glu Gln Ala Leu Ile Asp Ala Leu
```

```
Leu Gly Leu Gly Ala Ala His Gly Glu Gln Ala Leu Ile Asp Ala Leu
                245                 250                 255 cgc cgg gcg gtt gcg ttt cgc cgg ttc cgc gct gcc gac gtg cgc tcg      816
Arg Arg Ala Val Ala Phe Arg Arg Phe Arg Ala Ala Asp Val Arg Ser
            260                 265                 270 atc ctg gcc gcc ggc gcc ggc acc cca caa ccc cgc ccc gcc ggc gac      864
Ile Leu Ala Ala Gly Ala Gly Thr Pro Gln Pro Arg Pro Ala Gly Asp
        275                 280                 285 gca ctc gtg ctc gat ctg ccc acc gtc gag acc cgc tcg ttg gag gcc      912
Ala Leu Val Leu Asp Leu Pro Thr Val Glu Thr Arg Ser Leu Glu Ala
    290                 295                 300 tac aag atc aac acc acc gac ggg acg gcc tca tgaccaccgc tgccaagccg    965
Tyr Lys Ile Asn Thr Thr Asp Gly Thr Ala Ser
305                 310                 315 gtggcaccgt cctcggcggc accgctggct gctgaccttg acgcggcgct gcggcggttg   1025
aagctggcca cggtgcgccg caacgccgcc gaggtgttgc aagtcgccaa gacgcaacgc   1085
tggacaccgg aggagatcct gcggacgttg gttgaggccg agatcgctgc cgcgatgcc   1145 tccaacaccg ccaaccgtct caaggccgca gccttcccgg tcaccaagac cctcgacggg   1205
ttcgacgtca ccggatcgtc gatcaccgca gccacgttcg actacctgtc gagcctggaa   1265
tggattcggg cacaacagaa cctggcggtc attggcccac tggtacggg caaaagtcac    1325 ctgctcatcg gctgcgggca cgctgccgtc cacgccggat tcaaagtccg ctacttcacc   1385
gccgccgacc tgatcgaggt cctctaccgc ggcctggccg acaacaccgt cggcaagatc   1445
atcgacaccc tgctccgcgc ggatctggtc atcttggacg agatcggctt cgccccgctc   1505
gacgacaccg gactcaact gttgttccgg ctcgtggctg ccggctacga gcgccgctcc    1565
ctggccatcc cctcgcattg gcccttcgaa caatgggggc gattcctgcc cgagcacacc   1625
accgccgcca gcatcctcga tcggctgctg caccacgcca gcatcgtcgt cacctccggc   1685
gagtcctacc ggatgcgcca cgccgaccac aagaagggag ccgccaagaa ttag         1739

<210> SEQ ID NO 28
<211> LENGTH: 315
<212> TYPE: PRT
<213> ORGANISM: Mycobacterium

<400> SEQUENCE: 28

Met Gly Cys Leu Lys Gly Gly Val Val Ala Asn Val Val Pro Thr
1               5                   10                  15

Pro Asp Tyr Val Arg Phe Ala Ser His Tyr Gly Phe Val Pro Asp Phe
            20                  25                  30

Cys His Gly Ala Asp Pro Gln Ser Lys Gly Ile Val Glu Asn Leu Cys
        35                  40                  45

Gly Tyr Ala Gln Asp Asp Leu Ala Val Pro Leu Leu Thr Glu Ala Ala
    50                  55                  60

Leu Ala Gly Glu Gln Val Asp Leu Arg Ala Leu Asn Ala Gln Ala Gln
65                  70                  75                  80

Leu Trp Cys Ala Glu Val Asn Ala Thr Val His Ser Glu Ile Cys Ala
                85                  90                  95

Val Pro Asn Asp Arg Leu Val Asp Glu Arg Thr Val Leu Arg Glu Leu
            100                 105                 110

Pro Ser Leu Arg Pro Thr Ile Gly Ser Gly Ser Val Arg Arg Lys Val
        115                 120                 125

Asp Gly Leu Ser Cys Ile Arg Tyr Gly Ser Ala Arg Tyr Ser Val Pro
    130                 135                 140
```

```
Gln Arg Leu Val Gly Ala Thr Val Ala Val Val Asp His Gly Ala
145                 150                 155                 160

Leu Ile Leu Leu Glu Pro Ala Thr Gly Val Ile Val Ala Glu His Glu
                165                 170                 175

Leu Val Ser Pro Gly Glu Val Ser Ile Leu Asp Glu His Tyr Asp Gly
            180                 185                 190

Pro Arg Pro Ala Pro Ser Arg Gly Pro Arg Pro Lys Thr Gln Ala Glu
                195                 200                 205

Lys Arg Phe Cys Ala Leu Gly Thr Glu Ala Gln Gln Phe Leu Val Gly
210                 215                 220

Ala Ala Ala Ile Gly Asn Thr Arg Leu Lys Ser Glu Leu Asp Ile Leu
225                 230                 235                 240

Leu Gly Leu Gly Ala Ala His Gly Glu Gln Ala Leu Ile Asp Ala Leu
                245                 250                 255

Arg Arg Ala Val Ala Phe Arg Arg Phe Arg Ala Ala Asp Val Arg Ser
                260                 265                 270

Ile Leu Ala Ala Gly Ala Gly Thr Pro Gln Pro Arg Pro Ala Gly Asp
                275                 280                 285

Ala Leu Val Leu Asp Leu Pro Thr Val Glu Thr Arg Ser Leu Glu Ala
                290                 295                 300

Tyr Lys Ile Asn Thr Thr Asp Gly Thr Ala Ser
305                 310                 315

<210> SEQ ID NO 29
<211> LENGTH: 264
<212> TYPE: PRT
<213> ORGANISM: Mycobacteria
<220> FEATURE:
<221> NAME/KEY: DOMAIN
<222> LOCATION: (1)..(264)
<223> OTHER INFORMATION: amino acid sequence is encoded by nucleotides
      945-1736 of SEQ ID NO:27

<400> SEQUENCE: 29

Met Thr Thr Ala Ala Lys Pro Val Ala Pro Ser Ser Ala Ala Pro Leu
1               5                   10                  15

Ala Ala Asp Leu Asp Ala Ala Leu Arg Arg Leu Lys Leu Ala Thr Val
            20                  25                  30

Arg Arg Asn Ala Ala Glu Val Leu Gln Val Ala Lys Thr Gln Arg Trp
        35                  40                  45

Thr Pro Glu Glu Ile Leu Arg Thr Leu Val Glu Ala Glu Ile Ala Ala
    50                  55                  60

Arg Asp Ala Ser Asn Thr Ala Asn Arg Leu Lys Ala Ala Ala Phe Pro
65                  70                  75                  80

Val Thr Lys Thr Leu Asp Gly Phe Asp Val Thr Gly Ser Ser Ile Thr
                85                  90                  95

Ala Ala Thr Phe Asp Tyr Leu Ser Ser Leu Glu Trp Ile Arg Ala Gln
            100                 105                 110

Gln Asn Leu Ala Val Ile Gly Pro Pro Gly Thr Gly Lys Ser His Leu
        115                 120                 125

Leu Ile Gly Cys Gly His Ala Ala Val His Ala Gly Phe Lys Val Arg
    130                 135                 140

Tyr Phe Thr Ala Ala Asp Leu Ile Glu Val Leu Tyr Arg Gly Leu Ala
145                 150                 155                 160

Asp Asn Thr Val Gly Lys Ile Ile Asp Thr Leu Leu Arg Ala Asp Leu
                165                 170                 175
```

-continued

```
Val Ile Leu Asp Glu Ile Gly Phe Ala Pro Leu Asp Asp Thr Gly Thr
            180                 185                 190

Gln Leu Leu Phe Arg Leu Val Ala Ala Gly Tyr Glu Arg Arg Ser Leu
        195                 200                 205

Ala Ile Ala Ser His Trp Pro Phe Glu Gln Trp Gly Arg Phe Leu Pro
    210                 215                 220

Glu His Thr Thr Ala Ala Ser Ile Leu Asp Arg Leu His His Ala
225                 230                 235                 240

Ser Ile Val Val Thr Ser Gly Glu Ser Tyr Arg Met Arg His Ala Asp
                245                 250                 255

His Lys Lys Gly Ala Ala Lys Asn
            260
```

<210> SEQ ID NO 30
<211> LENGTH: 789
<212> TYPE: DNA
<213> ORGANISM: Mycobacterium
<220> FEATURE:
<221> NAME/KEY: CDS
<222> LOCATION: (1)..(786)

<400> SEQUENCE: 30

```
gtg acg tct gct ccg acc gtc tcg gtg ata acg atc tcg ttc aac gac      48
Met Thr Ser Ala Pro Thr Val Ser Val Ile Thr Ile Ser Phe Asn Asp
  1               5                  10                  15 ctc gac ggg ttg cag cgc acg gtg aaa agt gtg cgg gcg caa cgc tac      96
Leu Asp Gly Leu Gln Arg Thr Val Lys Ser Val Arg Ala Gln Arg Tyr
             20                  25                  30 cgg gga cgc atc gag cac atc gta atc gac ggt ggc agc ggc gac gac     144
Arg Gly Arg Ile Glu His Ile Val Ile Asp Gly Gly Ser Gly Asp Asp
         35                  40                  45 gtg gtg gca tac ctg tcc ggg tgt gaa cca ggc ttc gcg tat tgg cag     192
Val Val Ala Tyr Leu Ser Gly Cys Glu Pro Gly Phe Ala Tyr Trp Gln
     50                  55                  60 tcc gag ccc gac ggc ggg cgg tac gac gcg atg aac cag ggc atc gcg     240
Ser Glu Pro Asp Gly Gly Arg Tyr Asp Ala Met Asn Gln Gly Ile Ala
 65                  70                  75                  80 cac gca tcg ggt gat ctg ttg tgg ttc ttg cac tcc gcc gat cgt ttt     288
His Ala Ser Gly Asp Leu Leu Trp Phe Leu His Ser Ala Asp Arg Phe
                 85                  90                  95 tcc ggg ccc gac gtg gta gcc cag gcc gtg gag gcg cta tcc ggc aag     336
Ser Gly Pro Asp Val Val Ala Gln Ala Val Glu Ala Leu Ser Gly Lys
            100                 105                 110 gga ccg gtg tcc gaa ttg tgg ggc ttc ggg atg gat cgt ctc gtc ggg     384
Gly Pro Val Ser Glu Leu Trp Gly Phe Gly Met Asp Arg Leu Val Gly
        115                 120                 125 ctc gat cgg gtg cgc ggc ccg ata cct ttc agc ctg cgc aaa ttc ctg     432
Leu Asp Arg Val Arg Gly Pro Ile Pro Phe Ser Leu Arg Lys Phe Leu
    130                 135                 140 gcc ggc aag cag gtt gtt ccg cat caa gca tcg ttc ttc gga tca tcg     480
Ala Gly Lys Gln Val Val Pro His Gln Ala Ser Phe Phe Gly Ser Ser
145                 150                 155                 160 ctg gtg gcc aag atc ggt ggc tac gac ctt gat ttc ggg atc gcc gcc     528
Leu Val Ala Lys Ile Gly Gly Tyr Asp Leu Asp Phe Gly Ile Ala Ala
                165                 170                 175 gac cag gaa ttc ata ttg cgg gcc gcg ctg gta tgc gag ccg gtc acg     576
Asp Gln Glu Phe Ile Leu Arg Ala Ala Leu Val Cys Glu Pro Val Thr
            180                 185                 190 att cgg tgt gtg ctg tgc gag ttc gac acc acg ggc gtc ggc tcg cac     624
```

```
Ile Arg Cys Val Leu Cys Glu Phe Asp Thr Thr Gly Val Gly Ser His
        195                 200                 205 cgg gaa cca agc gcg gtc ttc ggt gat ctg cgc cgc atg ggc gac ctt     672
Arg Glu Pro Ser Ala Val Phe Gly Asp Leu Arg Arg Met Gly Asp Leu
    210                 215                 220 cat cgc cgc tac ccg ttc ggg gga agg cga ata tca cat gcc tac cta     720
His Arg Arg Tyr Pro Phe Gly Gly Arg Arg Ile Ser His Ala Tyr Leu
225                 230                 235                 240 cgc ggc cgg gag ttc tac gcc tac aac agt cga ttc tgg gaa aac gtc     768
Arg Gly Arg Glu Phe Tyr Ala Tyr Asn Ser Arg Phe Trp Glu Asn Val
                245                 250                 255 ttc acg cga atg tcg aaa tag                                         789
Phe Thr Arg Met Ser Lys
                260

<210> SEQ ID NO 31
<211> LENGTH: 262
<212> TYPE: PRT
<213> ORGANISM: Mycobacterium

<400> SEQUENCE: 31

Met Thr Ser Ala Pro Thr Val Ser Val Ile Thr Ile Ser Phe Asn Asp
  1               5                  10                  15

Leu Asp Gly Leu Gln Arg Thr Val Lys Ser Val Arg Ala Gln Arg Tyr
             20                  25                  30

Arg Gly Arg Ile Glu His Ile Val Ile Asp Gly Gly Ser Gly Asp Asp
         35                  40                  45

Val Val Ala Tyr Leu Ser Gly Cys Glu Pro Gly Phe Ala Tyr Trp Gln
     50                  55                  60

Ser Glu Pro Asp Gly Gly Arg Tyr Asp Ala Met Asn Gln Gly Ile Ala
 65                  70                  75                  80

His Ala Ser Gly Asp Leu Leu Trp Phe Leu His Ser Ala Asp Arg Phe
                 85                  90                  95

Ser Gly Pro Asp Val Val Ala Gln Ala Val Glu Ala Leu Ser Gly Lys
            100                 105                 110

Gly Pro Val Ser Glu Leu Trp Gly Phe Gly Met Asp Arg Leu Val Gly
        115                 120                 125

Leu Asp Arg Val Arg Gly Pro Ile Pro Phe Ser Leu Arg Lys Phe Leu
    130                 135                 140

Ala Gly Lys Gln Val Val Pro His Gln Ala Ser Phe Phe Gly Ser Ser
145                 150                 155                 160

Leu Val Ala Lys Ile Gly Gly Tyr Asp Leu Asp Phe Gly Ile Ala Ala
                165                 170                 175

Asp Gln Glu Phe Ile Leu Arg Ala Ala Leu Val Cys Glu Pro Val Thr
            180                 185                 190

Ile Arg Cys Val Leu Cys Glu Phe Asp Thr Thr Gly Val Gly Ser His
        195                 200                 205

Arg Glu Pro Ser Ala Val Phe Gly Asp Leu Arg Arg Met Gly Asp Leu
    210                 215                 220

His Arg Arg Tyr Pro Phe Gly Gly Arg Arg Ile Ser His Ala Tyr Leu
225                 230                 235                 240

Arg Gly Arg Glu Phe Tyr Ala Tyr Asn Ser Arg Phe Trp Glu Asn Val
                245                 250                 255

Phe Thr Arg Met Ser Lys
            260
```

```
<210> SEQ ID NO 32
<211> LENGTH: 1023
<212> TYPE: DNA
<213> ORGANISM: Mycobacterium
<220> FEATURE:
<221> NAME/KEY: CDS
<222> LOCATION: (1)..(1020)

<400> SEQUENCE: 32 gtg aag cga gcg ctc atc acc gga atc acc ggc cag gac ggc tcg tat        48
Met Lys Arg Ala Leu Ile Thr Gly Ile Thr Gly Gln Asp Gly Ser Tyr
 1               5                  10                  15 ctc gcc gaa ctg ctg ctg gcc aag ggg tat gag gtt cac ggg ctc atc        96
Leu Ala Glu Leu Leu Leu Ala Lys Gly Tyr Glu Val His Gly Leu Ile
             20                  25                  30 cgg cgc gct tcg acg ttc aac acc tcg cgg atc gat cac ctc tac gtc       144
Arg Arg Ala Ser Thr Phe Asn Thr Ser Arg Ile Asp His Leu Tyr Val
         35                  40                  45 gac ccg cac caa ccg ggc gcg cgg ctg ttt ctg cac tat ggt gac ctg       192
Asp Pro His Gln Pro Gly Ala Arg Leu Phe Leu His Tyr Gly Asp Leu
     50                  55                  60 atc gac gga acc cgg ttg gtg acc ctg ctg agc acc atc gaa ccc gac       240
Ile Asp Gly Thr Arg Leu Val Thr Leu Leu Ser Thr Ile Glu Pro Asp
 65                  70                  75                  80 gag gtg tac aac ctg gcg gcg cag tca cac gtg cgg gtg agc ttc gac       288
Glu Val Tyr Asn Leu Ala Ala Gln Ser His Val Arg Val Ser Phe Asp
                 85                  90                  95 gaa ccc gtg cac acc ggt gac acc acc ggc atg gga tcc atg cga ctg       336
Glu Pro Val His Thr Gly Asp Thr Thr Gly Met Gly Ser Met Arg Leu
            100                 105                 110 ctg gaa gcc gtt cgg ctc tct cgg gtg cac tgc cgc ttc tat cag gcg       384
Leu Glu Ala Val Arg Leu Ser Arg Val His Cys Arg Phe Tyr Gln Ala
        115                 120                 125 tcc tcg tcg gag atg ttc ggc gcc tcg ccg cca ccg cag aac gag ctg       432
Ser Ser Ser Glu Met Phe Gly Ala Ser Pro Pro Pro Gln Asn Glu Leu
    130                 135                 140 acg ccg ttc tac ccg cgg tca ccg tat ggc gcc gcc aag gtc tat tcg       480
Thr Pro Phe Tyr Pro Arg Ser Pro Tyr Gly Ala Ala Lys Val Tyr Ser
145                 150                 155                 160 tac tgg gcg acc cgc aat tat cgc gaa gcg tac gga ttg ttc gcc gtt       528
Tyr Trp Ala Thr Arg Asn Tyr Arg Glu Ala Tyr Gly Leu Phe Ala Val
                165                 170                 175 aac ggc atc ttg ttc aat cac gaa tca ccg cgg cgc ggt gag acg ttc       576
Asn Gly Ile Leu Phe Asn His Glu Ser Pro Arg Arg Gly Glu Thr Phe
            180                 185                 190 gtg acc cga aag atc acc agg gcc gtg gca cgc atc aag gcc ggt atc       624
Val Thr Arg Lys Ile Thr Arg Ala Val Ala Arg Ile Lys Ala Gly Ile
        195                 200                 205 cag tcc gag gtc tat atg ggc aat ctg gat gcg gtc cgc gac tgg ggg       672
Gln Ser Glu Val Tyr Met Gly Asn Leu Asp Ala Val Arg Asp Trp Gly
    210                 215                 220 tac gcg ccc gaa tac gtc gaa ggc atg tgg cgg atg ctg cag acc gac       720
Tyr Ala Pro Glu Tyr Val Glu Gly Met Trp Arg Met Leu Gln Thr Asp
225                 230                 235                 240 gag ccc gac gac ttc gtt ttg gcg acc ggg cgc ggt ttc acc gtg cgt       768
Glu Pro Asp Asp Phe Val Leu Ala Thr Gly Arg Gly Phe Thr Val Arg
                245                 250                 255 gag ttc gcg cgg gcc gcg ttc gag cat gcc ggt ttg gac tgg cag cag       816
Glu Phe Ala Arg Ala Ala Phe Glu His Ala Gly Leu Asp Trp Gln Gln
            260                 265                 270 tac gtg aaa ttc gac caa cgc tat ctg cgg ccc acc gag gtg gat tcg       864
```

```
Tyr Val Lys Phe Asp Gln Arg Tyr Leu Arg Pro Thr Glu Val Asp Ser
            275                 280                 285 ctg atc ggc gac gcg acc aag gct gcc gaa ttg ctg ggc tgg agg gct        912
Leu Ile Gly Asp Ala Thr Lys Ala Ala Glu Leu Leu Gly Trp Arg Ala
        290                 295                 300 tcg gtg cac act gac gag ttg gct cgg atc atg gtc gac gcg gac atg        960
Ser Val His Thr Asp Glu Leu Ala Arg Ile Met Val Asp Ala Asp Met
305                 310                 315                 320 gcg gcg ctg gag tgc gaa ggc aag ccg tgg atc gac aag ccg atg atc       1008
Ala Ala Leu Glu Cys Glu Gly Lys Pro Trp Ile Asp Lys Pro Met Ile
                325                 330                 335 gcc ggc cgg aca tga                                                   1023
Ala Gly Arg Thr
        340

<210> SEQ ID NO 33
<211> LENGTH: 340
<212> TYPE: PRT
<213> ORGANISM: Mycobacterium

<400> SEQUENCE: 33

Met Lys Arg Ala Leu Ile Thr Gly Ile Thr Gly Gln Asp Gly Ser Tyr
 1               5                  10                  15

Leu Ala Glu Leu Leu Ala Lys Gly Tyr Glu Val His Gly Leu Ile
            20                  25                  30

Arg Arg Ala Ser Thr Phe Asn Thr Ser Arg Ile Asp His Leu Tyr Val
        35                  40                  45

Asp Pro His Gln Pro Gly Ala Arg Leu Phe Leu His Tyr Gly Asp Leu
    50                  55                  60

Ile Asp Gly Thr Arg Leu Val Thr Leu Leu Ser Thr Ile Glu Pro Asp
65                  70                  75                  80

Glu Val Tyr Asn Leu Ala Ala Gln Ser His Val Arg Val Ser Phe Asp
                85                  90                  95

Glu Pro Val His Thr Gly Asp Thr Thr Gly Met Gly Ser Met Arg Leu
            100                 105                 110

Leu Glu Ala Val Arg Leu Ser Arg Val His Cys Arg Phe Tyr Gln Ala
        115                 120                 125

Ser Ser Ser Glu Met Phe Gly Ala Ser Pro Pro Gln Asn Glu Leu
    130                 135                 140

Thr Pro Phe Tyr Pro Arg Ser Pro Tyr Gly Ala Ala Lys Val Tyr Ser
145                 150                 155                 160

Tyr Trp Ala Thr Arg Asn Tyr Arg Glu Ala Tyr Gly Leu Phe Ala Val
                165                 170                 175

Asn Gly Ile Leu Phe Asn His Glu Ser Pro Arg Gly Glu Thr Phe
            180                 185                 190

Val Thr Arg Lys Ile Thr Arg Ala Val Ala Arg Ile Lys Ala Gly Ile
        195                 200                 205

Gln Ser Glu Val Tyr Met Gly Asn Leu Asp Ala Val Arg Asp Trp Gly
    210                 215                 220

Tyr Ala Pro Glu Tyr Val Glu Gly Met Trp Arg Met Leu Gln Thr Asp
225                 230                 235                 240

Glu Pro Asp Asp Phe Val Leu Ala Thr Gly Arg Gly Phe Thr Val Arg
                245                 250                 255

Glu Phe Ala Arg Ala Ala Phe Glu His Ala Gly Leu Asp Trp Gln Gln
            260                 265                 270

Tyr Val Lys Phe Asp Gln Arg Tyr Leu Arg Pro Thr Glu Val Asp Ser
```

```
                275                 280                 285
Leu Ile Gly Asp Ala Thr Lys Ala Ala Glu Leu Leu Gly Trp Arg Ala
    290                 295                 300

Ser Val His Thr Asp Glu Leu Ala Arg Ile Met Val Asp Ala Asp Met
305                 310                 315                 320

Ala Ala Leu Glu Cys Glu Gly Lys Pro Trp Ile Asp Lys Pro Met Ile
                325                 330                 335

Ala Gly Arg Thr
            340

<210> SEQ ID NO 34
<211> LENGTH: 732
<212> TYPE: DNA
<213> ORGANISM: Mycobacterium
<220> FEATURE:
<221> NAME/KEY: CDS
<222> LOCATION: (1)..(729)

<400> SEQUENCE: 34 atg agg ctg gcc cgt cgc gct cgg aac atc ttg cgt cgc aac ggc atc      48
Met Arg Leu Ala Arg Arg Ala Arg Asn Ile Leu Arg Arg Asn Gly Ile
1               5                   10                  15 gag gtg tcg cgc tac ttt gcc gaa ctg gac tgg gaa cgc aat ttc ttg      96
Glu Val Ser Arg Tyr Phe Ala Glu Leu Asp Trp Glu Arg Asn Phe Leu
                20                  25                  30 cgc caa ctg caa tcg cat cgg gtc agt gcc gtg ctc gat gtc ggg gcc     144
Arg Gln Leu Gln Ser His Arg Val Ser Ala Val Leu Asp Val Gly Ala
            35                  40                  45 aat tcg ggg cag tac gcc agg ggt ctg cgc ggc gcg ggc ttc gcg ggc     192
Asn Ser Gly Gln Tyr Ala Arg Gly Leu Arg Gly Ala Gly Phe Ala Gly
        50                  55                  60 cgc atc gtc tcg ttc gag ccg ctg ccc ggg ccc ttt gcc gtc ttg cag     240
Arg Ile Val Ser Phe Glu Pro Leu Pro Gly Pro Phe Ala Val Leu Gln
65                  70                  75                  80 cgc agc gcc tcc acg gac ccg ttg tgg gaa tgc cgg cgc tgt gcg ctg     288
Arg Ser Ala Ser Thr Asp Pro Leu Trp Glu Cys Arg Arg Cys Ala Leu
                85                  90                  95 ggc gat gtc gat gga acc atc tcg atc aac gtc gcc ggc aac gag ggc     336
Gly Asp Val Asp Gly Thr Ile Ser Ile Asn Val Ala Gly Asn Glu Gly
            100                 105                 110 gcc agc agt tcc gtc ttg ccg atg ttg aaa cga cat cag gac gcc ttt     384
Ala Ser Ser Ser Val Leu Pro Met Leu Lys Arg His Gln Asp Ala Phe
        115                 120                 125 cca cca gcc aac tac gtg ggc gcc caa cgg gtg ccg ata cat cga ctc     432
Pro Pro Ala Asn Tyr Val Gly Ala Gln Arg Val Pro Ile His Arg Leu
    130                 135                 140 gat tcc gtg gct gca gac gtt ctg cgg ccc aac gat att gcg ttc ttg     480
Asp Ser Val Ala Ala Asp Val Leu Arg Pro Asn Asp Ile Ala Phe Leu
145                 150                 155                 160 aag atc gac gtt caa gga ttc gag aag cag gtg atc gcg ggt ggc gat     528
Lys Ile Asp Val Gln Gly Phe Glu Lys Gln Val Ile Ala Gly Gly Asp
                165                 170                 175 tca acg gtg cac gac cga tgc gtc ggc atg cag ctc gag ctg tct ttc     576
Ser Thr Val His Asp Arg Cys Val Gly Met Gln Leu Glu Leu Ser Phe
            180                 185                 190 cag ccg ttg tac gag ggt ggc atg ctc atc cgc gag gcg ctc gat ctc     624
Gln Pro Leu Tyr Glu Gly Gly Met Leu Ile Arg Glu Ala Leu Asp Leu
        195                 200                 205 gtg gat tcg ttg ggc ttt acg ctc tcg gga ttg caa ccc ggt ttc acc     672
Val Asp Ser Leu Gly Phe Thr Leu Ser Gly Leu Gln Pro Gly Phe Thr
```

```
                  210                 215                 220
gac ccc cgc aac ggt cga atg ctg cag gcc gat ggc atc ttc ttc cgg       720
Asp Pro Arg Asn Gly Arg Met Leu Gln Ala Asp Gly Ile Phe Phe Arg
225                 230                 235                 240 ggc agc gat tga                                                       732
Gly Ser Asp <210> SEQ ID NO 35
<211> LENGTH: 243
<212> TYPE: PRT
<213> ORGANISM: Mycobacterium

<400> SEQUENCE: 35

Met Arg Leu Ala Arg Ala Arg Asn Ile Leu Arg Arg Asn Gly Ile
 1               5                  10                  15

Glu Val Ser Arg Tyr Phe Ala Glu Leu Asp Trp Glu Arg Asn Phe Leu
                20                  25                  30

Arg Gln Leu Gln Ser His Arg Val Ser Ala Val Leu Asp Val Gly Ala
            35                  40                  45

Asn Ser Gly Gln Tyr Ala Arg Gly Leu Arg Gly Ala Gly Phe Ala Gly
        50                  55                  60

Arg Ile Val Ser Phe Glu Pro Leu Pro Gly Pro Phe Ala Val Leu Gln
65                  70                  75                  80

Arg Ser Ala Ser Thr Asp Pro Leu Trp Glu Cys Arg Arg Cys Ala Leu
                85                  90                  95

Gly Asp Val Asp Gly Thr Ile Ser Ile Asn Val Ala Gly Asn Glu Gly
            100                 105                 110

Ala Ser Ser Ser Val Leu Pro Met Leu Lys Arg His Gln Asp Ala Phe
        115                 120                 125

Pro Pro Ala Asn Tyr Val Gly Ala Gln Arg Val Pro Ile His Arg Leu
    130                 135                 140

Asp Ser Val Ala Ala Asp Val Leu Arg Pro Asn Asp Ile Ala Phe Leu
145                 150                 155                 160

Lys Ile Asp Val Gln Gly Phe Glu Lys Gln Val Ile Ala Gly Gly Asp
                165                 170                 175

Ser Thr Val His Asp Arg Cys Val Gly Met Gln Leu Glu Leu Ser Phe
            180                 185                 190

Gln Pro Leu Tyr Glu Gly Gly Met Leu Ile Arg Glu Ala Leu Asp Leu
        195                 200                 205

Val Asp Ser Leu Gly Phe Thr Leu Ser Gly Leu Gln Pro Gly Phe Thr
    210                 215                 220

Asp Pro Arg Asn Gly Arg Met Leu Gln Ala Asp Gly Ile Phe Phe Arg
225                 230                 235                 240

Gly Ser Asp

<210> SEQ ID NO 36
<211> LENGTH: 732
<212> TYPE: DNA
<213> ORGANISM: Mycobacterium
<220> FEATURE:
<221> NAME/KEY: CDS
<222> LOCATION: (1)..(729)

<400> SEQUENCE: 36 gtg aaa tcg ttg aaa ctc gct cgt ttc atc gcg cgt agc gcc gcc ttc       48
Met Lys Ser Leu Lys Leu Ala Arg Phe Ile Ala Arg Ser Ala Ala Phe
 1               5                  10                  15
```

```
gag gtt tcg cgc cgc tat tct gag cga gac ctg aag cac cag ttt gtg      96
Glu Val Ser Arg Arg Tyr Ser Glu Arg Asp Leu Lys His Gln Phe Val
            20                  25                  30 aag caa ctc aaa tcg cgt cgg gta gat gtc gtt ttc gat gtc ggc gcc     144
Lys Gln Leu Lys Ser Arg Arg Val Asp Val Val Phe Asp Val Gly Ala
        35                  40                  45 aac tca gga caa tac gcc gcc ggc ctc cgc cga gca gca tat aag ggc     192
Asn Ser Gly Gln Tyr Ala Ala Gly Leu Arg Arg Ala Ala Tyr Lys Gly
    50                  55                  60 cgc att gtc tcg ttc gaa ccg cta tcc gga ccg ttt acg atc ttg gaa     240
Arg Ile Val Ser Phe Glu Pro Leu Ser Gly Pro Phe Thr Ile Leu Glu
65                  70                  75                  80 agc aaa gcg tca acg gat cca ctt tgg gat tgc cgg cag cat gcg ttg     288
Ser Lys Ala Ser Thr Asp Pro Leu Trp Asp Cys Arg Gln His Ala Leu
                85                  90                  95 ggc gat tct gat gga acg gtt acg atc aat atc gca gga aac gcc ggt     336
Gly Asp Ser Asp Gly Thr Val Thr Ile Asn Ile Ala Gly Asn Ala Gly
            100                 105                 110 cag agc agt tcc gtc ttg ccc atg ctg aaa agt cat cag aac gct ttt     384
Gln Ser Ser Ser Val Leu Pro Met Leu Lys Ser His Gln Asn Ala Phe
        115                 120                 125 ccc ccg gca aac tat gtc ggt acc caa gag gcg tcc ata cat cga ctt     432
Pro Pro Ala Asn Tyr Val Gly Thr Gln Glu Ala Ser Ile His Arg Leu
    130                 135                 140 gat tcc gtg gcg cca gaa ttt cta ggc atg aac ggt gtc gct ttt ctc     480
Asp Ser Val Ala Pro Glu Phe Leu Gly Met Asn Gly Val Ala Phe Leu
145                 150                 155                 160 aag gtc gac gtt caa ggc ttt gaa aag cag gtg ctc gcc ggg ggc aaa     528
Lys Val Asp Val Gln Gly Phe Glu Lys Gln Val Leu Ala Gly Gly Lys
                165                 170                 175 tca acc ata gat gac cat tgc gtc ggc atg caa ctc gaa ctg tcc ttc     576
Ser Thr Ile Asp Asp His Cys Val Gly Met Gln Leu Glu Leu Ser Phe
            180                 185                 190 ctg ccg ttg tac gaa ggt ggc atg ctc att cct gaa gcc ctc gat ctc     624
Leu Pro Leu Tyr Glu Gly Gly Met Leu Ile Pro Glu Ala Leu Asp Leu
        195                 200                 205 gtg tat tcc ttg ggc ttc acg ttg acg gga ttg ctg cct tgt ttc att     672
Val Tyr Ser Leu Gly Phe Thr Leu Thr Gly Leu Leu Pro Cys Phe Ile
    210                 215                 220 gat gca aat aat ggt cga atg ttg cag gcc gac ggc atc ttt ttc cgc     720
Asp Ala Asn Asn Gly Arg Met Leu Gln Ala Asp Gly Ile Phe Phe Arg
225                 230                 235                 240 gag gac gat tga                                                     732
Glu Asp Asp <210> SEQ ID NO 37
<211> LENGTH: 243
<212> TYPE: PRT
<213> ORGANISM: Mycobacterium

<400> SEQUENCE: 37

Met Lys Ser Leu Lys Leu Ala Arg Phe Ile Ala Arg Ser Ala Ala Phe
 1               5                   10                  15

Glu Val Ser Arg Arg Tyr Ser Glu Arg Asp Leu Lys His Gln Phe Val
            20                  25                  30

Lys Gln Leu Lys Ser Arg Arg Val Asp Val Val Phe Asp Val Gly Ala
        35                  40                  45

Asn Ser Gly Gln Tyr Ala Ala Gly Leu Arg Arg Ala Ala Tyr Lys Gly
    50                  55                  60
```

```
Arg Ile Val Ser Phe Glu Pro Leu Ser Gly Pro Phe Thr Ile Leu Glu
 65                  70                  75                  80

Ser Lys Ala Ser Thr Asp Pro Leu Trp Asp Cys Arg Gln His Ala Leu
                 85                  90                  95

Gly Asp Ser Asp Gly Thr Val Thr Ile Asn Ile Ala Gly Asn Ala Gly
            100                 105                 110

Gln Ser Ser Ser Val Leu Pro Met Leu Lys Ser His Gln Asn Ala Phe
        115                 120                 125

Pro Pro Ala Asn Tyr Val Gly Thr Gln Glu Ala Ser Ile His Arg Leu
    130                 135                 140

Asp Ser Val Ala Pro Glu Phe Leu Gly Met Asn Gly Val Ala Phe Leu
145                 150                 155                 160

Lys Val Asp Val Gln Gly Phe Glu Lys Gln Val Leu Ala Gly Gly Lys
                165                 170                 175

Ser Thr Ile Asp Asp His Cys Val Gly Met Gln Leu Glu Leu Ser Phe
            180                 185                 190

Leu Pro Leu Tyr Glu Gly Gly Met Leu Ile Pro Glu Ala Leu Asp Leu
        195                 200                 205

Val Tyr Ser Leu Gly Phe Thr Leu Thr Gly Leu Leu Pro Cys Phe Ile
    210                 215                 220

Asp Ala Asn Asn Gly Arg Met Leu Gln Ala Asp Gly Ile Phe Phe Arg
225                 230                 235                 240

Glu Asp Asp
```

<210> SEQ ID NO 38
<211> LENGTH: 828
<212> TYPE: DNA
<213> ORGANISM: Mycobacterium
<220> FEATURE:
<221> NAME/KEY: CDS
<222> LOCATION: (1)..(825)

<400> SEQUENCE: 38

```
atg gtg cag acg aaa cga tac gcc ggc ttg acc gca gct aac aca aag      48
Met Val Gln Thr Lys Arg Tyr Ala Gly Leu Thr Ala Ala Asn Thr Lys
 1               5                  10                  15 aaa gtc gcc atg gcc gca cca atg ttt tcg atc atc atc ccc acc ttg      96
Lys Val Ala Met Ala Ala Pro Met Phe Ser Ile Ile Ile Pro Thr Leu
             20                  25                  30 aac gtg gct gcg gta ttg cct gcc tgc ctc gac agc atc gcc cgt cag     144
Asn Val Ala Ala Val Leu Pro Ala Cys Leu Asp Ser Ile Ala Arg Gln
         35                  40                  45 acc tgc ggt gac ttc gag ctg gta ctg gtc gac ggc ggc tcg acg gac     192
Thr Cys Gly Asp Phe Glu Leu Val Leu Val Asp Gly Gly Ser Thr Asp
     50                  55                  60 gaa acc ctc gac atc gcc aac att ttc gcc ccc aac ctc ggc gag cgg     240
Glu Thr Leu Asp Ile Ala Asn Ile Phe Ala Pro Asn Leu Gly Glu Arg
 65                  70                  75                  80 ttg atc att cat cgc gac acc gac cag ggc gtc tac gac gcc atg aac     288
Leu Ile Ile His Arg Asp Thr Asp Gln Gly Val Tyr Asp Ala Met Asn
                 85                  90                  95 cgc ggc gtg gac ctg gcc acc gga acg tgg ttg ctc ttt ctg ggc gcg     336
Arg Gly Val Asp Leu Ala Thr Gly Thr Trp Leu Leu Phe Leu Gly Ala
            100                 105                 110 gac gac agc ctg tac gag gct gac acc ctg gcg cgg gtg gcc gcc ttc     384
Asp Asp Ser Leu Tyr Glu Ala Asp Thr Leu Ala Arg Val Ala Ala Phe
        115                 120                 125 att ggc gaa cac gag ccc agc gat ctg gta tat ggc gac gtg atc atg     432
```

-continued

```
Ile Gly Glu His Glu Pro Ser Asp Leu Val Tyr Gly Asp Val Ile Met
            130                 135                 140 cgc tca acc aat ttc cgc tgg ggt ggc gcc ttc gac ctc gac cgt ctg      480
Arg Ser Thr Asn Phe Arg Trp Gly Gly Ala Phe Asp Leu Asp Arg Leu
145                 150                 155                 160 ttg ttc aag cgc aac atc tgc cat cag gcg atc ttc tac cgc cgc gga      528
Leu Phe Lys Arg Asn Ile Cys His Gln Ala Ile Phe Tyr Arg Arg Gly
                165                 170                 175 ctc ttc ggc acc atc ggt ccc tac aac ctc cgc tac cgg gtc ctg gcc      576
Leu Phe Gly Thr Ile Gly Pro Tyr Asn Leu Arg Tyr Arg Val Leu Ala
            180                 185                 190 gac tgg gac ttc aat att cgc tgc ttt tcc aac cca gcg ctc gtc acc      624
Asp Trp Asp Phe Asn Ile Arg Cys Phe Ser Asn Pro Ala Leu Val Thr
        195                 200                 205 cgc tac atg cac gtg gtc gtt gca agc tac aac gaa ttc ggc ggg ctc      672
Arg Tyr Met His Val Val Val Ala Ser Tyr Asn Glu Phe Gly Gly Leu
    210                 215                 220 agc aat acg atc gtc gac aag gag ttt ttg aag cgg ctg ccg atg tcc      720
Ser Asn Thr Ile Val Asp Lys Glu Phe Leu Lys Arg Leu Pro Met Ser
225                 230                 235                 240 acg aga ctc ggc ata agg ctg gtc ata gtt ctg gtg cgc agg tgg cca      768
Thr Arg Leu Gly Ile Arg Leu Val Ile Val Leu Val Arg Arg Trp Pro
                245                 250                 255 aag gtg atc agc agg gcc atg gta atg cgc acc gtc att tct tgg cgg      816
Lys Val Ile Ser Arg Ala Met Val Met Arg Thr Val Ile Ser Trp Arg
            260                 265                 270 cgc cga cgt tag                                                      828
Arg Arg Arg
        275

<210> SEQ ID NO 39
<211> LENGTH: 275
<212> TYPE: PRT
<213> ORGANISM: Mycobacterium

<400> SEQUENCE: 39

Met Val Gln Thr Lys Arg Tyr Ala Gly Leu Thr Ala Ala Asn Thr Lys
  1               5                  10                  15

Lys Val Ala Met Ala Ala Pro Met Phe Ser Ile Ile Pro Thr Leu
            20                  25                  30

Asn Val Ala Ala Val Leu Pro Ala Cys Leu Asp Ser Ile Ala Arg Gln
            35                  40                  45

Thr Cys Gly Asp Phe Glu Leu Val Leu Val Asp Gly Gly Ser Thr Asp
        50                  55                  60

Glu Thr Leu Asp Ile Ala Asn Ile Phe Ala Pro Asn Leu Gly Glu Arg
 65                  70                  75                  80

Leu Ile Ile His Arg Asp Thr Asp Gln Gly Val Tyr Asp Ala Met Asn
                85                  90                  95

Arg Gly Val Asp Leu Ala Thr Gly Thr Trp Leu Leu Phe Leu Gly Ala
            100                 105                 110

Asp Asp Ser Leu Tyr Glu Ala Asp Thr Leu Ala Arg Val Ala Ala Phe
        115                 120                 125

Ile Gly Glu His Glu Pro Ser Asp Leu Val Tyr Gly Asp Val Ile Met
    130                 135                 140

Arg Ser Thr Asn Phe Arg Trp Gly Gly Ala Phe Asp Leu Asp Arg Leu
145                 150                 155                 160

Leu Phe Lys Arg Asn Ile Cys His Gln Ala Ile Phe Tyr Arg Arg Gly
                165                 170                 175
```

```
-continued

Leu Phe Gly Thr Ile Gly Pro Tyr Asn Leu Arg Tyr Arg Val Leu Ala
            180                 185                 190

Asp Trp Asp Phe Asn Ile Arg Cys Phe Ser Asn Pro Ala Leu Val Thr
        195                 200                 205

Arg Tyr Met His Val Val Ala Ser Tyr Asn Glu Phe Gly Gly Leu
    210                 215                 220

Ser Asn Thr Ile Val Asp Lys Glu Phe Leu Lys Arg Leu Pro Met Ser
225                 230                 235                 240

Thr Arg Leu Gly Ile Arg Leu Val Ile Val Leu Val Arg Arg Trp Pro
                245                 250                 255

Lys Val Ile Ser Arg Ala Met Val Met Arg Thr Val Ile Ser Trp Arg
            260                 265                 270

Arg Arg Arg
        275

<210> SEQ ID NO 40
<211> LENGTH: 24
<212> TYPE: DNA
<213> ORGANISM: Mycobacterium

<400> SEQUENCE: 40
gatgccgtga ggaggtaaag ctgc                                          24

<210> SEQ ID NO 41
<211> LENGTH: 24
<212> TYPE: DNA
<213> ORGANISM: Mycobacterium

<400> SEQUENCE: 41
gatacggctc ttgaatcctg cacg                                          24
```

VECTOR CARRYING A POLYNUCLEOTIDE WHICH ENCODES A GSD POLYPEPTIDE FROM MYCOBACTERIUM PARATUBERCULOSIS

The present application is continuation of U.S. application Ser. No. 10/805,311 (abandoned), filed Mar. 22, 2004, which is a divisional of U.S. application Ser. No. 09/705,911, filed Nov. 6, 2000 (abandoned), which is a divisional of U.S. Pat. No. 09/091,538, filed Sep. 16, 1998 (now U.S. Pat. No. 6,156, 322), which is a 371 U.S. National Phase of PCT/GB96/03221, filed Dec. 23, 1996, which claims benefit of GB 09526178.0 filed Dec. 21, 1995, the entire contents of each of which is incorporated herein by reference.

This invention relates to the novel polynucleocide sequence we have designated "GS" which we have identified in pathogenic mycobacteria. GS is a pathogenicity island within 8 kb of DNA comprising a core region of 5.75 kb and an adjacent transmissable element within 2.25 kb. GS is contained within *Mycobacterium paratuberculosis, Mycobacterium avium* subsp. *silvaticum* and some pathogenic isolates of *M. avium*. Functional portions of the core region of GS are also represented by regions with a high degree of homology that we have identified in cosmids containing genomic DNA from *Mycobacterium tuberculosis*.

BACKGROUND TO THE INVENTION

*Mycobacterium tuberculosis* (Mtb) is a major cause of global diseases of humans as well as animals. Although conventional methods of diagnosis including microscopy, culture and skin testing exist for the recognition of these diseases, improved methods particularly new immunodiagnostics and DNA-based detection systems are needed. Drugs used to treat tuberculosis are increasingly encountering the problem of resistant organisms. New drugs targeted at specific pathogenicity determinants as well as new vaccines for the prevention and treatment of tuberculosis are required. The importance of Mtb as a global pathogen is reflected in the commitment being made to sequencing the entire genome of this organism. This has generated a large amount of DNA sequence data of genomic DNA within cosmid and other libraries. Although the DNA sequence is known in the art, the functions of the vast majority of these sequences, the proteins they encode, the biological significance of these proteins, and the overall relevance and use of these genes and their products as diagnostics, vaccines and targets for chemotherapy for tuberculous disease, remains entirely unknown.

*Mycobacterium avium* subsp. *silvaticum* (Mavs) is a pathogenic mycobacterium causing diseases of animals and birds, but it can also affect humans. *Mycobacterium paratuberculosis* (Mptb) causes chronic inflammation of the intestine in many species of animals including primates and can also cause Crohn's disease in humans. Mptb is associated with other chronic inflammatory diseases of humans such as sarcoidosis. Subclinical Mptb infection is widespread in domestic livestock and is present in milk from infected animals. The organism is more resistant to pasteurisation than Mtb and can be conveyed to humans in retail milk supplies. Mptb is also present in water supplies, particularly those contaminated with run-off from heavily grazed pastures. Mptb and Mavs contain the insertion elements IS900 and IS902 respectively, and these are linked to pathogenicity in these organisms. IS900 and IS902 provide convenient highly specific multi-copy DNA targets for the sensitive detection of these organisms using DNA-based methods and for the diagnosis of infections in animals and humans. Much improvement is however required in the immunodiagnosis of Mptb and Mavs infections in animals and humans. Mptb and Mavs are in general, resistant in vivo to standard anti-tuberculous drugs. Although substantial clinical improvements in infections caused by Mptb, such as Crohn's disease, may result from treatment of patients with combinations of existing drugs such as Rifabutin, Clarithromycin or Azithromycin, additional effective drug treatments are required. Furthermore, there is an urgent need for effective vaccines for the prevention and treatment of Mptb and Mavs infections in animals and humans based upon the recognition of specific pathogenicity determinants.

Pathogenicity islands are, in general, 7-9 kb regions of DNA comprising a core domain with multiple ORFs and an adjacent transmissable element. The transmissable element also encodes proteins which may be linked to pathogenicity, such as by providing receptors for cellular recognition. Pathogenicity islands are envisaged as mobile packages of DNA which, when they enter an organism, assist in bringing about its convertion from a non-disease-causing to a disease-causing strain.

DESCRIPTION OF THE DRAWINGS

FIGS. 1(a) and (b) shows a linear map of the pathogenicity island GS in Mavs (FIG. 1a) and in Mptb (FIG. 1b). The main open reading frames are illustrated as ORFs A to H. ORFs A to F are found within the core region of GS. ORFs G and H are encoded by the adjacent transmissable element portion of GS.

DISCLOSURE OF THE INVENTION

Using a DNA-based differential analysis technology we have discovered and characterised a novel polynucleotide in Mptb (isolates 0022 from a Guernsey cow and 0021 from a red deer). This polynucleotide comprises the gene region we have designated GS. GS is found in Mptb using the identifier DNA sequences Seq. ID. No 1 and 2 where the Seq. ID No2 is the complementary sequence of Seq. ID No 1. GS is also identified in Mavs. The complete DNA sequence incorporating the positive strand of GS from an isolate of Mavs comprising 7995 nucleotides, including the core region of GS and adjacent transssmissable element, is given in Seq. ID No. 3. DNA sequence comprising 4435 bp of the positive strand of GS obtained from an isolate of Mptb including the core region of GS (nucleotides 1614 to 6047 of GS in Mavs) is given in Seq. ID No 4. The DNA sequence of GS from Mptb is highly (99.4%) homologous to GS in Mavs. The remaining portion of the DNA sequence of GS in Mptb, is readily obtainable by a person skilled in the art using standard laboratory procedures. The entire functional DNA sequence including core region and transmisable element of GS in Mptb and Mavs as described above, comprise the polynucleotide sequences of the invention.

There are 8 open reading frames (ORFs) in GS. Six of these designated GSA, GSB, GSC, GSD, GSE and GSF are encoded by the core DNA region of GS which, characteristically for a pathogenicity island, has a different GC content than the rest of the microbial genome. Two ORFs designated GSG and GSH are encoded by the transmissable element of GS whose GC content resembles that of the rest of the mycobacterial genome. The ORF GSH comprises two sub-ORFs $H_1$ $H_2$ on the complementary DNA strand linked by a programmed frameshifting site so that a single polypeptide is translated from the ORF GSH. The nucleotide sequences of the 8 ORFs in GS and their translations are shown in Seq. ID No 5 to Seq. ID No 29 as follows:

ORF A: Seq. ID No 5 Nucleotides 50 to 427 of GS from Mavs
  Seq. ID No 6 Amino acid sequence encoded by Seq. ID No 5.
ORF B: Seq. ID No 7 Nucleotides 772 to 1605 of GS from Mavs Seq. ID No 8 Amino acid sequence encoded by Seq. ID No 7.
ORF C: Seq. ID No 9 Nucleotides 1814 to 2845 of GS from Mavs Seq. ID No 10 Amino acid sequence encoded by Seq. ID No 9.
  Seq. ID No 11 Nucleotides 201 to 1232 of GS from Mptb Seq. ID No 12 Amino acid sequence encoded by Seq. ID No 11
ORF D: Seq. ID No 13 Nucleotides 2785 to 3804 of GS from Mavs Seq. ID No 14 Amino acid sequence encoded by Seq. ID No 13.
  Seq. ID No 15 Nucleotides 1172 to 2191 of GS from Mptb Seq. ID No 16 Amino acid sequence encoded by Seq. ID No 15.
ORF E: Seq. ID No 17 Nucleotides 4080 to 4802 of GS from Mavs Seq. ID No 18 Amino acid sequence encoded by Seq. ID No 17.
  Seq. ID No 19 Nucleotides 2467 to 3189 of GS from Mptb Seq. ID No 20 Amino acid sequence encoded by Seq. ID No 19.
ORF F: Seq. ID No 21 Nucleotides 4947 to 5747 of GS from Mavs Seq. ID No 22 Amino acid sequence encoded by Seq. ID No 21.
  Seq. ID No 23 Nucleotides 3335 to 4135 of GS from Mptb Seq. ID No 24 Amino acid sequence encoded by Seq. ID No 23.
ORF G: Seq. ID No 25 Nucleotides 6176 to 7042 of GS from Mavs Seq. ID No 26 Amino acid sequence encoded by Seq. ID No 25.
ORF H: Seq. ID No 27 Nucleotides 7953 to 6215 from Mavs.
ORF $H_1$: Seq. ID No 28 Amino acid sequence encoded by nucleotides 7953 to 7006 of Seq. ID No 27
ORF $H_2$: Seq. ID No 29 Amino acid sequence encoded by nucleotides 7009 to 6215 of Seq. ID No 27
  The polynucleotides in Mtb with homology to the ORFs B, C, E and F of GS in Mptb and Mavs, and the polypeptides they are now known to encode as a result of our invention, are as follows:
ORF B: Seq. ID No 30 Cosmid MTCY277 nucleotides 35493 to 34705
  Seq. ID No 31 Amino acid sequence encoded by Seq. ID No30.
ORF C: Seq. ID No 32 Cosmid MTCY277 nucleotides 31972 to 32994 Seq. ID No 33 Amino acid sequence encoded by Seq. ID No32.

ORF E: Seq. ID No 34 Cosmid MTCY277 nucleotides 34687 to 33956 Seq. ID No 35 Amino acid sequence encoded by Seq. ID No34.

ORF E: Seq. ID No 36 Cosmid MT024 nucleotides 15934 to 15203 Seq. ID No 37 Amino acid sequence encoded by Seq. ID No36.

ORF F: Seq. ID No 38 Cosmid MT024 nucleotides 15133 to 14306 Seq. ID No 39 Amino acid sequence encoded by Seq. ID No38.

The proteins and peptides encoded by the ORFs A to H in Mptb and Mavs and the amino acid sequences from homologous genes we have discovered in Mtb given in Seq. ID Nos 31, 33, 35, 37 and 39, as described above and fragments thereof, comprise the polypeptides of the invention. The polypeptides of the invention are believed to be associated with specific immunoreactivity and with the pathogenicity of the host micro-organisms from which they were obtained.

The present invention thus provides a polynucleotide in substantially isolated form which is capable of selectively hybridising to sequence ID Nos 3 or 4 or a fragment thereof. The polynucleotide fragment may alternatively comprise a sequence selected from the group of Seq. ID. No: 5, 7, 9, 11, 13, 15, 17, 19, 21, 23, 25 and 27. The invention further provides a polynucleotide in substantially isolated form whose sequence consists essentially of a sequence selected from the group Seq ID Nos. 30, 32, 34, 36 and 38, or a corresponding sequence selectively hybridizable thereto, or a fragment of said sequence or corresponding sequence.

The invention further provides diagnostic probes such as a probe which comprises a fragment of at least 15 nucleotides of a polynucleotide of the invention, or a peptide nucleic acid or similar synthetic sequence specific ligand, optionally carrying a revealing label. The invention also provides a vector carrying a polynucleotide as defined above, particularly an expression vector.

The invention further provides a polypeptide in substantially isolated form which comprises any one of the sequences selected from the group consisting Seq. ID. No: 6, 8, 10, 12, 14, 16, 18, 20, 22, 24, 26, 28, 29, 31, 33, 35, 37 and 39, or a polypeptide substantially homologous thereto. The invention additionally provides a polypeptide fragment which comprises a fragment of a polypeptide defined above, said fragment comprising at least 10 amino acids and an epitope. The invention also provides polynucleotides in substantially isolated form which encode polypeptides of the invention, and vectors which comprise such polynucleotides, as well as antibodies capable of binding such polypeptides. In an additional aspect, the invention provides kits comprising polynucleotides, polypeptides, antibodies or synthetic ligands of the invention and methods of using such kits in diagnosing the presence or absence of mycobacteria in a sample. The invention also provides pharmaceutical compositions comprising polynucleotides of the invention, polypeptides of the invention or antisense probes and the use of such compositions in the treatment or prevention of diseases caused by mycobacteria. The invention also provides polynucleotihe prevention and treatment of infections due to GS-containing pathogenic mycobacteria in animals and humans and as a means of enhacing in vivo susceptibility of said mycobacteria to antimicrobial drugs. The invention also provides bacteria or viruses transformed with polynucleotides of the invention for use as vaccines. The invention further provides Mptb or Mavs in which all or part or the polynucleotides of the invention have been deleted or disabled to provide mutated organisms of lower pathogenicity for use as vaccines in animals and humans. The invention further provides Mtb in which all or part of the polynucleotides encoding polypeptides of the invention have been deleted or disabled to provided mutated organisms or lower pathogenicity for use as vaccines in animals and humans.

A further aspect of the invention is our discovery of homologies between the ORFs B, C and E in GS on the one hand, and Mtb cosmid MTCY277 on the other (data from Genbank database using the computer programmes BLAST and BLIXEM). The homologous ORFs in MTCY277 are adjacent to one another consistent with the form of another pathogenicity island in Mtb. A further aspect of the invention is our discovery of homologies between ORFs E and F in GS, and Mtb cosmid MTO24 (also Genbank, as above) with the homologous ORFs close to one another. The use of polynucleotides and polypeptides from Mtb (Seq. ID Nos 30, 31, 32, 33, 34, 35, 36, 37, 38 and 39) in substantially isolated form as diagnostics, vaccines and targets for chemotherapy, for the management and prevention of Mtb infections in humans and animals, and the processes involved in the preparation and use of these diagnostics, vaccines and new chemotherapeutic agents, comprise further aspects of the invention.

DETAILED DESCRIPTION OF THE INVENTION

A. Polynucleotides

Polynucleotides of the invention as defined herein may comprise DNA or RNA. They may also be polynucleotides which include within them synthetic or modified nucleotides or peptide nucleic acids. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to couple the said polynucleotide to a solid phase or to enhance the recognition, the in vivo activity, or the lifespan of polynucleotides of the invention.

A number of different types of polynucleotides of the invention are envisaged. In the broadest aspect, polynucleotides and fragments thereof capable of hybridizing to SEQ ID NO:3 or 4 form a first aspect of the invention. This includes the polynucleotide of SEQ ID NO: 3 or 4. Within this class of polynucleotides various sub-classes of polynucleotides are of particular interest.

One sub-class of polynucleotides which is of interest is the class of polynucleotides encoding the open reading frames A, B, C, D, E, F, G and H, including SEQ ID NOs:5, 7, 9, 11, 13, 15, 17, 19, 21, 23, 25 and 27. As discussed below, polynucleotides encoding ORF H include the polynucleotide sequences 7953 to 7006 and 7009 to 6215 within SEQ ID NO: 27, as well as modified sequences in which the frame-shift has been modified so that the two sub-reading frames are placed in a single reading frame. This may be desirable where the polypeptide is to be produced in recombinant expression systems.

The invention thus provides a polynucleotide in substantially isolated form which encodes any one of these ORFs or combinations thereof. Combinations thereof includes combinations of 2, 3, 4, 5 or all of the ORFS. Polynucleotides may be provided which comprise an individual ORF carried in a recombinant vector including the vectors described herein. Thus in one preferred aspect the invention provides a polynucleotide in substantially isolated form capable of selectively hybridizing to the nucleic acid comprising ORFs A to F of the core region of the Mptb and Mavs pathogenicity islands of the invention. Fragments thereof corresponding to ORFs A to E, B to F, A to D, B to E, A to C, B to D or any two adjacent ORFs are also included in the invention.

Polynucleotides of the invention will be capable of selectively hybridizing to the corresponding portion of the GS region, or to the corresponding ORFs of Mtb described herein. The term "selectively hybridizing" indicates that the polynucleotides will hybridize, under conditions of medium to high stringency (for example 0.03 M sodium chloride and 0.03 M sodium citrate at from about 50° C. to about 60° C.) to the corresponding portion of SEQ ID NO:3 or 4 or the complementary strands thereof but not to genomic DNA from mycobacteria which are usually non-pathogenic including non-pathogenic species of *M. avium*. Such polynucleotides will generally be generally at least 68%, e.g. at least 70%, preferably at least 80 or 90% and more preferably at least 95% homologous to the corresponding DNA of GS. The corresponding portion will be of over a region of at least 20, preferably at least 30, for instance at least 40, 60 or 100 or more contiguous nucleotides.

By "corresponding portion" it is meant a sequence from the GS region of the same or substantially similar size which has been determined, for example by computer alignment, to have the greatest degree of homology to the polynucleotide.

Any combination of the above mentioned degrees of homology and minimum sizes may be used to define polynucleotides of the invention, with the more stringent combinations (i.e. higher homology over longer lengths) being preferred. Thus for example a polynucleotide which is at least 80% homologous over 25, preferably 30 nucleotides forms one aspect of the invention, as does a polynucleotide which is at least 90% homologous over 40 nucleotides.

A further class of polynucleotides of the invention is the class of polynucleotides encoding polypeptides of the invention, the polypeptides of the invention being defined in section B below. Due to the redundancy of the genetic code as such, polynucleotides may be of a lower degree of homology than required for selective hybridization to the GS region. However, when such polynucleotides encode polypeptides of the invention these polynucleotides form a further aspect. It may for example be desirable where polypeptides of the invention are produced recombinantly to increase the GC content of such polynucleotides. This increase in GC content may result in higher levels of expression via codon usage more appropriate to the host cell in which recombinant expression is taking place.

An additional class of polynucleotides of the invention are those obtainable from cosmids MTCY277 and MT024 (containing Mtb genomic sequences), which polynucleotides consist essentially of the fragment of the cosmid containing an open reading frame encoding any one of the homologous ORFs B, C, E or F respectively. Such polynucleotides are referred to below as Mtb polynucleotides. However, where reference is made to polynucleotides in general such reference includes Mtb polynucleotides unless the context is explicitly to the contrary. In addition, the invention provides polynucleotides which encode the same polypeptide as the abovementioned ORFs of Mtb but which, due to the redundancy of the genetic code, have different nucleotide sequences. These form further Mtb polynucleotides of the invention. Fragments of Mtb polynucleotides suitable for use as probes or primers also form a further aspect of the invention.

The invention further provides polynucleotides in substantially isolated form capable of selectively hybridizing (where selectively hybridizing is as defined above) to the Mtb polynucleotides of the invention.

The invention further provides the Mtb polynucleotides of the invention linked, at either the 5' and/or 3' end to polynucleotide sequences to which they are not naturally contiguous. Such sequences will typically be sequences found in cloning or expression vectors, such as promoters, 5' untranslated sequence, 3' untranslated sequence or termination sequences. The sequences may also include further coding sequences such as signal sequences used in recombinant production of proteins.

Further polynucleotides of the invention are illustrated in the accompanying examples.

Polynucleotides of the invention may be used to produce a primer, e.g. a PCR primer, a primer for an alternative amplification reaction, a probe e.g. labelled with a revealing label by conventional means using radioactive or non-radioactive labels or a probe linked covalently to a solid phase, or the polynucleotides may be cloned into vectors. Such primers, probes and other fragments will be at least 15, preferably at least 20, for example at least 25, 30 or 40 or more nucleotides in length, and are also encompassed by the term polynucleotides of the invention as used herein.

Primers of the invention which are preferred include primers directed to any part of the ORFs defined herein. The ORFs from other isolates of pathogenic mycobacteria which contain a GS region may be determined and conserved regions within each individual ORF may be identified. Primers directed to such conserved regions form a further preferred aspect of the invention. In addition, the primers and other polynucleotides of the invention may be used to identify, obtain and isolate ORFs capable of selectively hybridizing to the polynucleotides of the invention which are present in pathogenic mycobacteria but which are not part of a pathogenicity island in that particular species of bacteria. Thus in addition to the ORFs B, C, E and F which have been identified in Mtb, similar ORFs may be identified in other pathogens and ORFs corresponding to the GS ORFs C, D, E, F and H, may also be identified.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a step-wise manufacture of the desired nucleic acid sequence one nucleotide at a time. Techniques for accomplishing this using automated techniques are readily available in the art. Longer polynucleotides will generally be produced using recombinant means, for example using a PCR (polymerase chain reaction) cloning techniques. This will involve making a pair or primers (e.g. of about 15-30 nucleotides) to a region of GS, which it is desired to clone, bringing the primers into contact with genomic DNA from a mycobacterium or a vector carrying the GS sequence, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the GS or ORF sequences described herein, as well as further genomic clones containing full open reading frames. Although in general such techniques are well known in the art, reference may be made in particular to Sambrook J., Fritsch E F., Maniatis T (1989). Molecular cloning: a Laboratory Manual, 2nd edn. Cold Spring Harbor, N.Y., Cold Spring Harbor Laboratory.

Polynucleotides which are not 100% homologous to the sequences of the present invention but fall within the scope of the invention can be obtained in a number of ways.

Other isolates or strains of pathogenic mycobacteria will be expected to contain allelic variants of the GS sequences described herein, and these may be obtained for example by probing genomic DNA libraries made from such isolates or strains of bacteria using GS or ORF sequences as probes under conditions of medium to high stringency (for example 0.03M sodium chloride and 0.03M sodium citrate at from about 50° C. to about 60° C.).

A particularly preferred group of pathogenic mycobacteria are isolates of *M. paratuberculosis*. Plynucleotides based on GS regions from such bacteria are particularly preferred. Preferred fragments of such regions include fragments encoding individual open reading frames including the preferred groups and combinations of open reading frames discussed above.

Alternatively, such polynucleotides may be obtained by site directed mutagenesis of the GS or ORF sequences or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides of the invention. Such altered property or function will include the addition of amino acid sequences of consensus signal peptides known in the art to effect transport and secretion of the modified polypeptide of the invention. Another altered property will include metagenesis of a catalytic residue or generation of fusion proteins with another polypeptide. Such fusion proteins may be with an enzyme, with an antibody or with a cytokine or other ligand for a receptor, to target a polypeptide of the invention to a specific cell type in vitro or in vivo.

The invention further provides double stranded polynucleotides comprising a polynucleotide of the invention and its complement.

Polynucleotides or primers of the invention may carry a revealing label. Suitable labels include radioisotopes such as $^{32}P$ or $^{35}S$, enzyme labels, other protein labels or smaller labels such as biotin or fluorophores. Such labels may be added to polynucleotides or primers of the invention and may be detected using by techniques known per se.

Polynucleotides or primers of the invention or fragments thereof labelled or unlabelled may be used by a person skilled in the art in nucleic acid-based tests for the presence or absence of Mptb, Mavs, other GS-containing pathogenic mycobacteria, or Mtb applied to samples of body fluids, tissues, or excreta from animals and humans, as well as to food and environmental samples such as river or ground water and domestic water supplies.

Human and animal body fluids include sputum, blood, serum, plasma, saliva, milk, urine, csf, semen, faeces and infected discharges. Tissues include intestine, mouth ulcers, skin, lymph nodes, spleen, lung and liver obtained surgically or by a biopsy technique. Animals particularly include commercial livestock such as cattle, sheep, goats, deer, rabbits but wild animals and animals in zoos may also be tested.

Such tests comprise bringing a human or animal body fluid or tissue extract, or an extract of an environmental or food sample, into contact with a probe comprising a polynucleotide or primer of the invention under hybridising conditions and detecting any duplex formed between the probe and nucleic acid in the sample. Such detection may be achieved using techniques such as PCR or by immobilising the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected. Suitable assay methods of this any other formats can be found in for example WO89/03891 and WO90/13667.

Polynucleotides of the invention or fragments thereof labelled or unlabelled may also be used to identify and characterise different strains of Mptb, Mavs, other GS-containing pathogenic mycobacteria, or Mtb, and properties such as drug resistance or susceptibility.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridising the probe to nucleic acid in the sample, control reagents, instructions, and the like.

The use of polynucleotides of the invention in the diagnosis of inflammatory diseases such as Crohn's disease or sarcoidosis in humans or Johne's disease in animals form a preferred aspect of the invention. The polynucleotides may also be used in the prognosis of these diseases. For example, the response of a human or animal subject in response to antibiotic, vaccination or other therapies may be monitored by utilizing the diagnostic methods of the invention over the course of a period of treatment and following such treatment.

The use of Mtb polynucleotides (particularly in the form of probes and primers) of the invention in the above-described methods form a further aspect of the invention, particularly for the detection, diagnosis or prognosis of Mtb infections.

B. Polypeptides.

Polypeptides of the invention include polypeptides in substantially isolated form encoded by GS. This includes the full length polypeptides encoded by the positive and complementary negative strands of GS. Each of the full length polypeptides will contain one of the amino acid sequences set out in Seq ID NOs:6, 8, 10, 12, 14, 16, 18, 20, 22, 24, 26, 28 and 29. Polypeptides of the invention further include variants of such sequences, including naturally occurring allelic variants and synthetic variants which are substantially homologous to said polypeptides. In this context, substantial homology is regarded as a sequence which has at least 70%, e.g. 80%, 90%, 95% or 98% amino acid homology (identity) over 30 or more, e.g 40, 50 or 100 amino acids. For example, one group of substantially homolgous polypeptides are those which have at least 95% amino acid identity to a polypeptide of any one of Seq ID NOs:6, 8, 10, 12, 14, 16, 18, 20, 22, 24, 26, 28 and 29 over their entire length. Even more preferably, this homology is 98%.

Polypeptides of the invention further include the polypeptide sequences of the homologous ORFs of Mtb, namely Seq ID Nos. 31, 33, 35, 37 and 39. Unless explicitly specified to the contrary, reference to polypeptides of the invention and their fragments include these Mtb polypeptides and fragments, and variants thereof (substanially homologous to said sequences) as defined herein.

Polypeptides of the invention may be obtained by the standard techniques mentioned above. Polypeptides of the invention also include fragments of the above mentioned full length polypeptides and variants thereof, including fragments of the sequences set out in SEQ ID NOs:6, 8, 10, 12, 14, 16, 18, 20, 22, 24, 26, 28, 29, 31, 33, 35, 37 and 39. Such fragments for example of 8, 10, 12, 15 or up to 30 or 40 amino acids may also be obtained synthetically using standard techniques known in the art.

Preferred fragments include those which include an epitope, especially an epitope which is specific to the pathogenicity of the mycobacterial cell from which the polypeptide is derived. Suitable fragments will be at least about 5, e.g. 8, 10, 12, 15 or 20 amino acids in size, or larger. Epitopes may be determined either by techniques such as peptide scanning techniques as described by Geysen et al, Mol. Immunol., 23; 709-715 (1986), as well as other techniques known in the art.

The term "an epitope which is specific to the pathogenicity of the mycobacterial cell" means that the epitope is encoded by a portion of the GS region, or by the corresponding ORF sequences of Mtb which can be used to distinguish mycobacteria which are pathogenic by from related non-pathogenic mycobacteria including non-pathogenic species of *M. avium*. This may be determined using routine methodology. A candidate epitope from an ORF may be prepared and used to immunise an animal such as a rat or rabbit in order to generate antibodies. The antibodies may then be used to detect the presence of the epitope in pathogenic mycobacteria and to confirm that non-pathogenic mycobacteria do not contain any proteins which react with the epitope. Epitopes may be linear or conformational.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Polypeptides of the invention may be modified to confer a desired property or function for example by the addition of Histidine residues to assist their purification or by the addition of a signal sequence to promote their secretion from a cell.

Thus, polypeptides of the invention include fusion proteins which comprise a polypeptide encoding all or part of one or more of an ORF of the invention fused at the N- or C-terminus to a second sequence to provide the desired property or function. Sequences which promote secretion from a cell include, for example the yeast α-factor signal sequence.

A polypeptide of the invention may be labelled with a revealing label. The revealing label may be any suitable label which allows the polypeptide to be detected. Suitable labels include radioisotopes, e.g. $^{125}I$, $^{35}S$ enzymes, antibodies, polynucleotides and ligands such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well, microparticle, dipstick or biosensor. Such labelled and/or immobilized polypeptides may be packaged into kits in a suitable container along with suitable reagents, controls, instructions and the like.

Such polypeptides and kits may be used in methods of detection of antibodies or cell mediated immunoreactivity, to the mycobacterial proteins and peptides encoded by the ORFs of the invention and their allelic variants and fragments, using immunoassay. Such host antibodies or cell mediated immune reactivity will occur in humans or animals with an immune system which detects and reacts against polypeptides of the invention. The antibodies may be present in a biological sample from such humans or animals, where the biological sample may be a sample as defined above particularly blood, milk or saliva.

Immunoassay methods are well known in the art and will generally comprise:

(a) providing a polypeptide of the invention comprising an epitope bindable by an antibody against said mycobacterial polypeptide;

(b) incubating a biological sample with said polypeptide under conditions which allow for the formation of an antibody-antigen complex; and (c) determining whether antibody-antigen complex comprising said polypeptide is formed.

Immunoassay methods for cell mediated immune reactivity in animals and humans are also well known in the art (e.g. as described by Weir et al 1994, J. Immunol Methods 176; 93-101) and will generally comprise (a) providing a polypeptide of the invention comprising an epitope bindable by a lymphocyte or macrophage or other cell receptor;

(b) incubating a cell sample with said polypeptide under conditions which allow for a cellular immune response such as release of cytokines or other mediator to occur; and (c) detecting the presence of said cytokine or mediator in the incubate.

Polypeptides of the invention may be made by standard synthetic means well known in the art or recombinantly, as described below.

Polypeptides of the invention or fragments thereof labelled or unlabelled may also be used to identify and characterise different strains of Mptb, Mavs, other GS-containing pathogenic mycobacteria, or Mtb, and properties such as drug resistance or susceptibility.

The polypeptides of the invention may conveniently be packaged in the form of a test kit in a suitable container. In such kits the polypeptide may be bound to a solid support where the assay format for which the kit is designed requires such binding. The kit may also contain suitable reagents for treating the sample to be examined, control reagents, instructions, and the like.

The use of polypeptides of the invention in the diagnosis of inflammatory diseases such as Crohn's disease or sarcoidosis in humans or Johne's disease in animals form a preferred aspect of the invention. The polypeptides may also be used in the prognosis of these diseases. For example, the response of a human or animal subject in response to antibiotic or other therapies may be monitored by utilizing the diagnostic methods of the invention over the course of a period of treatment and following such treatment.

The use of Mtb polypeptides of the invention in the above-described methods form a further aspect of the invention, particularly for the detection, diagnosis or prognosis of Mtb infections.

Polypeptides of the invention may also be used in assay methods for identifying candidate chemical compounds which will be useful in inhibiting, binding to or disrupting the function of said polypeptides required for pathogenicity. In general, such assays involve bringing the polypeptide into contact with a candidate inhibitor compound and observing the ability of the compound to disrupt, bind to or interfer with the polypeptide.

There are a number of ways in which the assay may be formatted. For example, those polypeptides which have an enzymatic function may be assayed using labelled substrates for the enzyme, and the amount of, or rate of, conversion of the substrate into a product measured, e.g by chromatograpy such as HPLC or by a colourimetric assay. Suitable labels include $^{35}S$, $^{125}I$, biotin or enzymes such as horse radish peroxidase.

For example, the gene product of ORF C is believed to have GDP-mannose dehydratase activty. Thus an assay for inhbitors of the gene product may utilise for example labelled GDP-mannose, GDP or mannose and the activity of the gene product followed. ORF D encodes a gene related to the synthesis and regulation of capuslar polysaccharides, which are often associated with invasiveness and pathogenicity. Labelled polysaccharide substrates may be used in assays of the ORF D gene product. The gene product of ORF F encodes a protein with putative glucosyl transferase activity and thus labelled amino sugars such as β-1-3-N-acetylglucosamine may be used as substrates in assays.

Candidate chemical compounds which may be used may be natural or synthetic chemical compounds used in drug screening programmes. Extracts of plants which contain several characterised or uncharacterised components may also be used.

Alternatively, the a polypeptide of the invention may be screened against a panel of peptides, nucleic acids or other chemical functionalities which are generated by combinatorial chemistry. This will allow the definition of chemical entities which bind to polypeptides of the invention. Typically, the polypeptide of the invention will be brought into contact with a panel of compounds from a combinantorial library, with either the panel or the polypeptide being immobilized on a solid phase, under conditions suitable for the polypeptide to bind to the panel. The solid phase will then be washed under conditions in which only specific interactions between the polypeptide and individual members of the panel are retained, and those specific members may be utilized in further assays or used to design further panels of candidate compounds.

For example, a number of assay methods to define peptide interaction with peptides are known. For example, WO86/00991 describes a method for determining mimotopes which comprises making panels of catamer preparations, for example octamers of amino acids, at which one or more of the positions is defined and the remaining positions are randomly made up of other amino acids, determining which catamer binds to a protein of interest and re-screening the protein of interest against a further panel based on the most reactive catamer in which one or more additional designated positions are systematically varied. This may be repeated throughout a number of cycles and used to build up a sequence of a binding candidate compound of interest.

WO89/03430 describes screening methods which permit the preparation of specific mimotopes which mimic the immunological activity of a desired analyte. These mimotopes are identified by reacting a panel of individual peptides wherein said peptides are of systematically varying hydrophobicity, amphipathic characteristics and charge patterns, using an antibody against an antigen of interest. Thus in the present case antibodies against the a polypeptide of the inventoin may be employed and mimotope peptides from such panels may be identified.

C. Vectors.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

D. Expression Vectors.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above, under conditions to provide for expression by the vector of a coding sequence encoding the polypeptides, and recovering the expressed polypeptides.

A further embodiment of the invention provides vectors for the replication and expression of polynucleotides of the invention, or fragments thereof. The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of naked DNA vaccination or gene therapy. A further embodiment of the invention provides host cells transformed or transfected with the vectors for the replication and expression of polynucleotides of the invention, including the DNA of GS, the open reading frames thereof and other corresponding ORFs particularly ORFs B, C, E and F from Mtb. The cells will be chosen to be compatible with the said vector and may for example be bacterial, yeast, insect or mammalian.

Expression vectors are widely available in the art and can be obtained commercially. Mammalian expression vectors may comprise a mammalian or viral promoter. Mammalian promoters include the metallothionien promoter. Viral promoters include promoters from adenovirus, the SV40 large T promoter and retroviral LTR promoters. Promoters compatible with insect cells include the polyhedrin promoter. Yeast promoters include the alcohol dehydrogenase promoter. Bacterial promoters include the β-galactosidase promoter.

The expression vectors may also comprise enhancers, and in the case of eukaryotic vectors polyadenylation signal sequence downstream of the coding sequence being expressed.

Polypeptides of the invention may be expressed in suitable host cells, for example bacterial, yeast, plant, insect and mammalian cells, and recovered using standard purification techniques including, for example affinity chromatography, HPLC or other chromatographic separation techniques.

Polynucleotides according to the invention may also be inserted into the vectors described above in an antisense orientation in order to provide for the production of antisense RNA. Antisense RNA or other antisense polynucleotides or ligands may also be produced by synthetic means. Such antisense polynucleotides may be used in a method of controlling the levels of the proteins encoded by the ORFs of the invention in a mycobacterial cell.

Polynucleotides of the invention may also be carried by vectors suitable for gene therapy methods. Such gene therapy methods include those designed to provide vaccination against diseases caused by pathogenic mycobacteria or to boost the immune response of a human or animal infected with a pathogenic mycobacteria.

For example, Ziegner et al, AIDS, 1995, 9;43-50 describes the use of a replication defective recombinant amphotropic retrovirus to boost the immune response in patients with HIV infection. Such a retrovirus may be modified to carry a polynucleotide encoding a polypeptide or fragment thereof of the invention and the retrovirus delivered to the cells of a human or animal subject in order to provide an immune response against said polypeptide. The retrovirus may be delivered directly to the patient or may be used to infecte cells ex-vivo, e.g. fibroblast cells, which are then introduced into the patient, optionally after being inactivated. The cells are desirably autologous or HLA-matched cells from the human or animal subject.

Gene therapy methods including methods for boosting an immune response to a particluar pathogen are disclosed generally in for example WO95/14091, the disclosure of which is incoporated herein by reference. Recombinant viral vectors include retroviral vectors, adenoviral vectors, adeno-associated viral vectors, vaccinia virus vectors, herpes virus vectors and alphavirus vectors. Alpha virus vectors are described in, for example, WO95/07994, the disclosure of which is incorporated herein by reference.

Where direct administration of the recombinant viral vector is contemplated, either in the form of naked nucleic acid or in the form of packaged particles carrying the nucleic acid this may be done by any suitable means, for example oral administration or intravenous injection. From $10^5$ to $10^8$ c.f.u of virus represents a typical dose, which may be repeated for example weekly over a period of a few months. Administration of autologous or HLA-matched cells infected with the virus may be more convenient in some cases. This will generally be achieved by administering doses, for example from $10^5$ to $10^8$ cells per dose which may be repeated as described above.

The recombinant viral vector may further comprise nucleic acid capable of expressing an accessory molecule of the immune system designed to increase the immune response. Such a moleclue may be for example and interferon, particularly interferon gamma, an interleukin, for example IL-1α, IL-1β or IL-2, or an HLA class I or II moleclue. This may be particularly desirable where the vector is intended for use in the treatment of humans or animals already infected with a mycobacteria and it is desired to boost the immune response.

E. Antibodies.

The invention also provides monoclonal or polyclonal antibodies to polypeptides of the invention or fragments thereof. The invention further provides a process for the production of monoclonal or polyclonal antibodies to polypeptides of the invention. Monoclonal antibodies may be prepared by conventional hybridoma technology using the polypeptides of the invention or peptide fragments thereof, as immunogens. Polyclonal antibodies may also be prepared by conventional means which comprise inoculating a host animal, for example a rat or a rabbit, with a polypeptide of the invention or peptide fragment thereof and recovering immune serum.

In order that such antibodies may be made, the invention also provides polypeptides of the invention or fragments thereof haptenised to another polypeptide for use as immunogens in animals or humans.

For the purposes of this invention, the term "antibody", unless specified to the contrary, includes fragments of whole antibodies which retain their binding activity for a polypeptide of the invention. Such fragments include Fv, F(ab') and F(ab')$_2$ fragments, as well as single chain antibodies. Furthermore, the antibodies and fragments thereof may be humanised antibodies, e.g. as described in EP-A-239400.

Antibodies may be used in methods of detecting polypeptides of the invention present in biological samples (where such samples include the human or animal body samples, and environmental samples, mentioned above) by a method which comprises:

(a) providing an antibody of the invention;
(b) incubating a biological sample with said antibody under conditions which allow for the formation of an antibody-antigen complex; and
(c) determining whether antibody-antigen complex comprising said antibody is formed.

Antibodies of the invention may be bound to a solid support for example an immunoassay well, microparticle, dipstick or biosensor and/or packaged into kits in a suitable container along with suitable reagents, controls, instructions and the like.

Antibodies of the invention may be used in the detection, diagnosis and prognosis of diseases as descirbed above in relation to polypeptides of the invention.

F. Compositions.

The present invention also provides compositions comprising a polynucleotide or polypeptide of the invention together with a carrier or diluent. Compositions of the invention also include compositions comprising a nucleic acid, particularly and expression vector, of the invention. Compositions further include those carrying a recombinant virus of the invention. Such compositions include pharmaceutical compositions in which case the carrier or diluent will be pharmaceutically acceptable.

Pharmaceutically acceptable carriers or diluents include those used in formulations suitable for inhalation as well as oral, parenteral (e.g. intramuscular or intravenous or transcutaneous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents, and liposomes or other microparticulate systems which are designed to target the polynucleotide or the polypeptide of the invention to blood components or one or more organs, or to target cells such as M cells of the intestine after oral administration.

G. Vaccines.

In another aspect, the invention provides novel vaccines for the prevention and treatment of infections caused by Mptb, Mavs, other GS-containing pathogenic mycobacteria and Mtb in animals and humans. The term "vaccine" as used herein means an agent used to stimulate the immune system of a vertebrate, particularly a warm blooded vertebrate including humans, so as to provide protection against future harm by an organism to which the vaccine is directed or to assist in the eradication of an organism in the treatment of established infection. The immune system will be stimulated by the production of cellular immunity antibodies, desirably neutralizing antibodies, directed to epitopes found on or in a pathogenic mycobacterium which expresses any one of the ORFs of the invention. The antibody so produced may be any of the immunological classes, such as the immunoglobulins A, D, E, G or M. Vaccines which stimulate the production of IgA are interest since this is the principle immunoglobulin produced by the secretory system of warm-blooded animals, and the production of such antibodies will help prevent infection or colonization of the intestinal tract. However an IgM and IgG response will also be desirable for systemic infections such as Crohn's disease or tuberculosis.

Vaccines of the invention include polynucleotides of the invention or fragments thereof in suitable vectors and administered by injection of naked DNA using standard protocols. Polynucleotides of the invention or fragments thereof in suitable vectors for the expression of the polypeptides of the invention may be given by injection, inhalation or by mouth. Suitable vectors include *M. bovis* BCG, *M. smegmatis* or other mycobacteria, *Corynebacteria, Salmonella* or other agents according to established protocols.

Polypeptides of the invention or fragments thereof in substantially isolated form may be used as vaccines by injection, inhalation, oral administration or by transcutaneous application according to standard protocols. Adjuvants (such as Iscoms or polylactide-coglycolide encapsulation), cytokines such as IL-12 and other immunomodulators may be used for the selective enhancement of the cell mediated or humoral immunological responses. Vaccination with polynucleotides and/or polypeptides of the invention may be undertaken to increase the susceptibility of pathogenic mycobacteria to antimicrobial agents in vivo.

In instances wherein the polypeptide is correctly configured so as to provide the correct epitope, but is too small to be immunogenic, the polypeptide may be linked to a suitable carrier.

A number of techniques for obtaining such linkage are known in the art, including the formation of disulfide linkages using N-succinimidyl-3-(2-pyridylthio) propionate (SPDP) and succinimidyl 4-(N-maleimido-methyl)cyclohexane-1-carboxylate (SMCC) obtained from Pierce Company, Rockford, Ill., (if the peptide lacks a sulfhydryl group, this can be provided by addition of a cysteine residue). These reagents create a disulfide linkage between themselves and peptide cysteine residues on one protein and an amide linkage through the epsilon-amino on a lysine, or other free amino group in the other. A variety of such disulfide/amide-forming agents are known. See, for example, *Immun Rev* (1982) 62:185. Other bifunctional coupling agents form a thioether rather than a disulfide linkage. Many of these thioether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl group can be activated by combining them with succinimide or 1-hydroxyl-2-nitro-4-sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized Sepharose®, agarose, cellulose, cellulose beads and the like; polymeric amino acids, such as polyglutamic acid, polylysine, polylactide-coglycolide and the like; amino acid copolymers; and inactive virus particles. Especially useful protein substrates are serum albumins, keyhole limpet hemocyanin, immunoglobulin molecules, thyroglobulin, ovalbumin, tetanus toxoid, and other proteins well known to those skilled in the art.

The immunogenicity of the epitopes may also be enhanced by preparing them in mammalian or yeast systems fused with or assembled with particle-forming proteins such as, for example, that associated with hepatitis B surface antigen. See, e.g., U.S. Pat. No. 4,722,840. Constructs wherein the epitope is linked directly to the particle-forming protein coding sequences produce hybrids which are immunogenic with respect to the epitope. In addition, all of the vectors prepared include epitopes specific to HBV, having various degrees of immunogenicity, such as, for example, the pre-S peptide.

In addition, portions of the particle-forming protein coding sequence may be replaced with codons encoding an epitope of the invention. In this replacement, regions which are not required to mediate the aggregation of the units to form immunogenic particles in yeast or mammals can be deleted, thus eliminating additional HBV antigenic sites from competition with the epitope of the invention.

Vaccines may be prepared from one or more immunogenic polypeptides of the invention. These polypeptides may be expressed in various host cells (e.g., bacteria, yeast, insect, or mammalian cells), or alternatively may be isolated from viral preparations or made synthetically.

In addition to the above, it is also possible to prepare live vaccines of attenuated microorganisms which express one or more recombinant polypeptides of the invention. Suitable attenuated microorganisms are known in the art and include, for example, viruses (e.g., vaccinia virus), as well as bacteria.

The preparation of vaccines which contain an immunogenic polypeptide(s) as active ingredients, is known to one skilled in the art. Typically, such vaccines are prepared as injectables, or as suitably encapsulated oral preparations and either liquid solutions or suspensions; solid forms suitable for solution in, or suspension in, liquid prior to injestion or injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 (polyoxyethylene sorbitan monooleate) emulsion. The effectiveness of an adjuvant may be determined by measuring the amount of antibodies directed against an immunogenic polypeptide containing an antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories, oral formulations or as enemas. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 µg to 250 µg, of antigen per dose, depends on the subject to be treated, capacity of the subject's immune system to synthesize antibodies, mode of administration and the degree of protection desired. Precise amounts of active ingredient required to be administered may depend on the judgement of the practitioner and may be peculiar to each subject.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reenforce the immune response, for example, at 1-4 months for a second dose, and if needed, a subsequent dose(s) after several months. The dosage regimen will also, at least in part, be determined by the need of the individual and be dependent upon the judgement of the practitioner.

In a further aspect of the invention, there is provided an attenuated vaccine comprising a normally pathogenic mycobacteria which harbours an attenuating mutation in any one of the genes encoding a polypeptide of the invention. The gene is selected from the group of ORFs A, B, C, D, E, F, G and H, including the homologous ORFs B, C, E and F in Mtb.

The mycobacteria may be used in the form of killed bacteria or as a live attenuated vaccine. There are advantages to a live attenuated vaccine. The whole live organism is used, rather than dead cells or selected cell components which may exhibit modified or denatured antigens. Protein antigens in the outer membrane will maintain their tertiary and quaternary structures. Therefore the potential to elicit a good protective long term immunity should be higher.

The term "mutation" and the like refers to a genetic lesion in a gene which renders the gene non-functional. This may be at either the level of transcription or translation. The term thus envisages deletion of the entire gene or substantial portions thereof, and also point mutations in the coding sequence which result in truncated gene products unable to carry out the normal function of the gene.

A mutation introduced into a bacterium of the invention will generally be a non-reverting attenuating mutation. Non-reverting means that for practical purposes the probability of the mutated gene being restored to its normal function is small, for example less than 1 in $10^6$ such as less than 1 in $10^9$ or even less than 1 in $10^{12}$.

An attenuated mycobacteria of the invention may be in isolated form. This is usually desirable when the bacterium is to be used for the purposes of vaccination. The term "isolated" means that the bacterium is in a form in which it can be cultured, processed or otherwise used in a form in which it can be readily identified and in which it is substantially uncontaminated by other bacterial strains, for example non-attenuated parent strains or unrelated bacterial strains. The term "isolated bacterium" thus encompasses cultures of a bacterial mutant of the invention, for example in the form of colonies on a solid medium or in the form of a liquid culture, as well as frozen or dried preparations of the strains.

In a preferred aspect, the attenuated mycobacterium further comprises at least one additional mutation. This may be a mutation in a gene responsible for the production of products essential to bacterial growth which are absent in a human or animal host. For example, mutations to the gene for aspartate semi-aldehyde dehydrogenase (asd) have been proposed for the production of attenuated strains of Salmonella. The asd gene is described further in Gene (1993) 129; 123-128. A lesion in the asd gene, encoding the enzyme aspartate β-semi-aldehyde dehydrogenase would render the organism auxotrophic for the essential nutrient diaminopelic acid (DAP), which can be provided exogenously during bulk culture of the vaccine strain. Since this compound is an essential constituent of the cell wall for gram-negative and some gram-positive organisms and is absent from mammalian or other vertebrate tissues, mutants would undergo lysis after about three rounds of division in such tissues. Analogous mutations may be made to the attenuated mycobacteria of the invention.

In addition or in the alternative, the attenuated mycobacteria may carry a recA mutation. The recA mutation knocks out homologous recombination—the process which is exploited for the construction of the mutations. Once the recA mutation has been incorporated the strain will be unable to repair the constructed deletion mutations. Such a mutation will provide attenuated strains in which the possibility of homologous recombination to with DNA from wild-type strains has been minimized. RecA genes have been widely studied in the art and their sequences are available. Further modifications may be made for additional safety.

The invention further provides a process for preparing a vaccine composition comprising an attenuated bacterium according to the invention process comprises (a) inoculating a culture vessel containing a nutrient medium suitable for growth of said bacterium; (b) culturing said bacterium; (c) recovering said bacteria and (d) mixing said bacteria with a pharmaceutically acceptable diluent or carrier.

Attenuated bacterial strains according to the invention may be constructed using recombinant DNA methodology which is known per se. In general, bacterial genes may be mutated by a process of targeted homologous recombination in which a DNA construct containing a mutated form of the gene is introduced into a host bacterium which it is desired to attenuate. The construct will recombine with the wild-type gene carried by the host and thus the mutated gene may be incorporated into the host genome to provide a bacterium of the present invention which may then be isolated.

The mutated gene may be obtained by introducing deletions into the gene, e.g by digesting with a restriction enzyme which cuts the coding sequence twice to excise a portion of the gene and then religating under conditions in which the excised portion is not reintroduced into the cut gene. Alternatively frame shift mutations may be introduced by cutting with a restriction enzyme which leaves overhanging 5' and 3' termini, filling in and/or trimming back the overhangs, and religating. Similar mutations may be made by site directed mutagenesis. These are only examples of the types of techniques which will readily be at the disposal of those of skill in the art.

Various assays are available to detect successful recombination. In the case of attenuations which mutate a target gene necessary for the production of an essential metabolite or catabolite compound, selection may be carried out by screening for bacteria unable to grow in the absence of such a compound. Bacteria may also be screened with antibodies or nucleic acids of the invention to determine the absence of production of a mutated gene product of the invention or to confirm that the genetic lesion introduced—e.g. a deletion—has been incorporated into the genome of the attenuated strain.

The concentration of the attenuated strain in the vaccine will be formulated to allow convenient unit dosage forms to be prepared. Concentrations of from about $10^4$ to $10^9$ bacteria per ml will generally be suitable, e.g. from about $10^5$ to $10^8$ such as about $10^6$ per ml. Live attenuated organisms may be administered subcutaneously or intramuscularly at up to $10^8$ organisms in one or more doses, e.g from around $10^5$ to $10^8$, e.g about $10^6$ or $10^7$ organisms in a single dose.

The vaccines of the invention may be administered to recipients to treat established disease or in order to protect them against diseases caused by the corresponding wild type mycobacteria, such as inflammatory diseases such as Crohn's disease or sarcoidosis in humans or Johne's disease in animals. The vaccine may be administered by any suitable route. In general, subcutaneous or intramuscular injection is most convenient, but oral, intranasal and colorectal administration may also be used.

The following Examples illustrates aspects of the invention.

EXAMPLE 1

Tests for the presence of the GS identifier sequence were performed on 5 µl bacterial DNA extracts (25 µg/ml to 500 µg/ml) using polymerase chain reaction based on the oligonucleotide primers 5'-GATGCCGTGAGGAGG-TAAAGCTGC-3' (Seq ID No. 40) and 5'-GATACGGCTCT-TGAATCCTGCACG-3' (Seq ID No. 41) from within the identifier DNA sequences (Seq. ID Nos 1 and 2). PCR was performed for 40 cycles in the presence of 1.5 mM magnesium and an annealing temperature of 58° C. The presence or absence of the correct amplification product indicated the presence or absence of GS identifier sequence in the corresponding bacterium. GS identifier sequence is shown to be present in all the laboratory and field strains of Mptb and Mavs tested. This includes Mptb isolates 0025 (bovine CVL Weybridge), 0021 (caprine, Moredun), 0022 (bovine, Moredun), 0139 (human, Chiodini 1984), 0209, 0208, 0211, 0210, 0212, 0207, 0204, 0206 (bovine, Whipple 1990). All Mptb strains were IS900 positive. The Mavs strains include 0010 and 0012 (woodpigeon, Thorel) 0018 (armadillo, Portaels) and 0034, 0037, 0038, 0040 (AIDS, Hoffner). All Mavs strains were IS902 positive. One pathogenic M. avium strain 0033 (AIDS, Hoffner) also contained GS identifier sequence. GS identifier sequence is absent from other mycobacteria including other M. avium, M. malmoense, M. szulgai, M.

gordonae, M. chelonei, M. fortuitun, M. phlei, as well as E. coli, S. areus, Nocardia sp, Streptococcus sp. Shigella sp. Pseudomonas sp.

EXAMPLE 2

To obtain the full sequence of GS in Mavs and Mptb we generated a genomic library of Mavs using the restriction endonuclease EcoRI and cloning into the vector pUC18. This achieved a representative library which was screened with $^{32}$P-labelled identifier sequence yielding a positive clone containing a 17 kbp insert. We constructed a restriction map of this insert and identified GS as fragments unique to Mavs and Mptb and not occurring in laboratory strains of M. avium*. These fragments were sub-cloned into pUC18 and pGEM4Z. We identified GS contained within an 8 kb region. The full nucleotide sequence was determined for GS on both DNA strands using primer walking and automated DNA sequencing. DNA sequence for GS in Mptb was obtained using overlapping PCR products generated using PwoDNA polymerase, a proofreading thermostable enzyme. The final DNA sequences were derived using the University of Wisconsin GCG gel assembly software package.

EXAMPLE 3

The DNA sequence of GS in Mavs and Mptb was found to be more than 99% homologous. The ORFs encoded in GS were identified using GeneRunner and DNAStar computer programmes. Eight ORFs were identified and designated GSA, GSB, GSC, GSD, GSE, GSF, GSG and GSH. Database comparisons were carried out against the GenEMBL Database release version 48.0 (9/96), using the BLAST and BLIXEM programmes. GSA and GSB encoded proteins of 13.5 kDa and 30.7 kDa respectively, both of unknown functions. GSC encoded a protein of 38.4 kDa with a 65% homology to the amino acid sequence of rfbD of *V. cholerae*, a 62% amino acid sequence homology to gmd of *E. coli* and a 58% homology to gca of *Ps. aeruginosa* which are all GDP-D-mannose dehydratases. Equivalent gene products in *H. influenzae, S. dysenteriae, Y. enterocolitica, N. gonorrhoea, K. pneumoniae* and rfbD in *Salmonella enterica* are all involved in 'O'-antigen processing known to be linked to pathogenicity. GSD encoded a protein of 37.1 kDa which showed 58% homology at the DNA level to wcaG from *E. coli*, a gene involved in the synthesis and regulation of capsular polysaccharides, also related to pathogenicity. GSE was found to have a >30% amino acid homology to rfbT of *V. cholerae*, involved in the transport of specific LPS components across the cell membrane. In *V. cholerae* the gene product causes a seroconversion from the Inaba to the Ogawa 'epidemic' strain. GSF encoded a protein of 30.2 kDa which was homologous in the range 25-40% at the amino acid level to several glucosyl transferases such as rfpA of *K. pneumoniae*, rfbB of *K. pneumoniae*, lgtD of *H. influenzae*, lsi of *N. gonorrhoae*. In *E. coli* an equivalent gene galE adds β-1-3 N-acetylglucosamine to galactose, the latter only found in 'O' and 'M' antigens which are also related to pathogenicity. GSH comprising the ORFs $GSH_1$ and $GSH_2$ encodes a protein totalling about 60 kDa which is a putative transposase with a 40-43% homology at the amino acid level to the equivalent gene product of IS21 in *E. coli*. This family of insertion sequences is broadly distributed amongst gram negative bacteria and is responsible for mobility and transposition of genetic elements. An IS21— like element in *B. fragilis* is split either side of the β-lactamase gene controlling its activation and expression. We programmed an *E. coli* S30 cell-free extract with plasmid DNA containing the ORF GSH under the control of a lac promoter in the presence of a $^{35}S$-methionine, and demonstrated the translation of an abundant 60 kDa protein. The proteins homologous to GS encoded in other organisms are in general highly antigenic. Thus the proteins encoded by the ORFs in GS may be used in immunoassays of antibody or cell mediated immuno-reactivity for diagnosing infections caused by mycobacteria, particularly Mptb, Mavs and Mtb. Enhancement of host immune recognition of GS encoded proteins by vaccination using naked specific DNA or recombinant GS proteins, may be used in the prevention and treatment of infections caused by Mptb, Mavs and Mtb in humans and animals. Mutation or deletion of all or some of the ORFs A to H in GS may be used to generate attenuated strains of Mptb, Mavs or Mtb with lower pathogenicity for use as living or killed vaccines in humans and animals. Such vaccines are particularly relevant to Johne's disease in animals, to diseases caused by Mptb in humans such as Crohn's disease, and to the management of tuberculosis especially where the disease is caused by multiple drug-resistant organisms.

The invention claimed is:

1. A vector carrying a polynucleotide comprising:
   (a) a polynucleotide encoding the polypeptide of SEQ ID NO:24; or
   (b) a polynucleotide that encodes a polypeptide having at least 90% sequence identity to the polypeptide of SEQ ID NO:24.

2. A vector according to claim 1 wherein said polynucleotide comprises the polynucleotide of SEQ ID NO:23.

3. A vector according to claim 1, which is an expression vector.

4. A vector according to claim 3, wherein said polynucleotide is operably linked to a control sequence which is capable of providing for the expression of the coding sequence of the polynucleotide.

5. A vector according to claim 1 which comprises one or more components selected from the group consisting of an origin of replication, a promoter for expression of the polypeptide encoded by said polynucleotide, a regulator of a promoter for expression of the polypeptide encoded by said polypeptide, an enhancer and a selectable marker gene.

6. A vector according to claim 5, wherein said promoter is a mammalian, viral, yeast or bacterial promoter.

7. A vector according to claim 6, wherein said promoter is selected from the group consisting of: a metallothionine promoter, an adenovirus promoter, the SV40 large T promoter, a retroviral LTR promoter, the polyhedrin promoter, an alcohol dehydrogenase promoter and a β-galactosidase promoter.

8. A vector according to claim 1, which is a plasmid, virus or phage vector.

9. A vector according to claim 8, wherein said viral vector is selected from the group consisting of retroviral vectors, adenoviral vectors, adeno-associated viral vectors, vaccinia virus vectors, herpes virus vector and alpha virus vectors.

10. An isolated host cell comprising, transformed with, or transfected by a vector according to claim 1.

11. An isolated host cell according to claim 10, which is a bacterial, yeast, insect or mammalian cell.

12. A host cell according to claim 11 which is selected from the group consisting of Mycobacterium bovis BCG, Mycobacterium smegmatis, a mycobacterium, a Corynebacteria and A Salmonella.

13. A pharmaceutical composition comprising:
   (a) a polynucleotide encoding the polypeptide of SEQ ID NO:24;
   (b) a polynucleotide that encodes a polypeptide having at least 90% sequence identity to the polypeptide of SEQ ID NO:24;
   (c) a vector according to claim 1; or
   (d) a host cell containing said vector; and a pharmaceutically acceptable carrier or diluent.

14. A composition according to claim 13 wherein said polynucleotide comprises the polynucleotide of SEQ ID NO:23.

* * * * *